United States Patent
Kleinschnitz et al.

(10) Patent No.: US 12,065,481 B2
(45) Date of Patent: Aug. 20, 2024

(54) THERAPY USING A FACTOR XII INHIBITOR IN A NEUROTRAUMATIC DISORDER

(71) Applicant: CSL BEHRING GMBH, Marburg (DE)

(72) Inventors: Christoph Kleinschnitz, Heiligenhaus-Isenbuegel (DE); Marc Nolte, Marburg (DE); Anna-Leena Sirén, Wuerzburg (DE); Christiane Albert-Weissenberger, Bergtheim (DE); Sarah Hopp-Kraemer, Wuerzburg (DE)

(73) Assignee: CSL BEHRING GMBH, Marburg (DE)

( * ) Notice: Subject to any disclaimer, the term of this patent is extended or adjusted under 35 U.S.C. 154(b) by 476 days.

(21) Appl. No.: 16/666,886

(22) Filed: Oct. 29, 2019

(65) Prior Publication Data
US 2020/0131248 A1 Apr. 30, 2020

Related U.S. Application Data

(63) Continuation of application No. 15/318,550, filed as application No. PCT/EP2015/063760 on Jun. 18, 2015, now abandoned.

(30) Foreign Application Priority Data

Jun. 18, 2014 (EP) .................................. 14172910

(51) Int. Cl.
| | | |
|---|---|---|
| C07K 16/36 | (2006.01) |
| A61K 9/00 | (2006.01) |
| A61K 31/573 | (2006.01) |
| A61K 38/55 | (2006.01) |
| A61K 38/57 | (2006.01) |
| A61K 39/395 | (2006.01) |
| A61K 47/50 | (2017.01) |
| C07K 14/76 | (2006.01) |
| C07K 14/81 | (2006.01) |
| A61K 39/00 | (2006.01) |

(52) U.S. Cl.
CPC .......... *C07K 14/811* (2013.01); *A61K 9/0019* (2013.01); *A61K 31/573* (2013.01); *A61K 38/55* (2013.01); *A61K 38/57* (2013.01); *A61K 39/3955* (2013.01); *A61K 47/50* (2017.08); *C07K 14/76* (2013.01); *C07K 14/8135* (2013.01); *C07K 16/36* (2013.01); *A61K 2039/505* (2013.01); *C07K 2317/76* (2013.01); *C07K 2319/31* (2013.01)

(58) Field of Classification Search
None
See application file for complete search history.

(56) References Cited

U.S. PATENT DOCUMENTS

| | | |
|---|---|---|
| 5,252,714 A | 10/1993 | Harris et al. |
| 6,403,077 B1 | 6/2002 | Strom et al. |
| 8,283,319 B2 | 10/2012 | Schulte et al. |
| 9,352,016 B2 | 5/2016 | Zeitler et al. |
| 9,518,127 B2 | 12/2016 | Panousis et al. |
| 9,624,307 B2 | 4/2017 | Nahrendorf et al. |
| 9,856,325 B2 | 1/2018 | Panousis et al. |
| 9,856,326 B2 | 1/2018 | Panousis et al. |
| 9,952,016 B2 | 4/2018 | Sullivan et al. |
| 9,957,329 B2 | 5/2018 | Meuth et al. |
| 9,987,328 B2 | 6/2018 | Zeitler et al. |
| 10,286,047 B2 | 5/2019 | Spirig et al. |
| 10,471,142 B2 | 11/2019 | Basta et al. |
| 2004/0087778 A1 | 5/2004 | Feige et al. |
| 2014/0072572 A1 | 3/2014 | Nahrendorf et al. |
| 2014/0234293 A1 | 8/2014 | Basta et al. |
| 2014/0378653 A1 | 12/2014 | Meuth et al. |
| 2016/0008442 A1 | 1/2016 | Spirig et al. |
| 2016/0166660 A1 | 6/2016 | Nolte et al. |
| 2016/0279195 A1 | 9/2016 | Zeitler et al. |
| 2017/0114119 A1 | 4/2017 | Kleinschnitz et al. |
| 2019/0269766 A1 | 9/2019 | Spirig et al. |
| 2019/0309089 A1 | 10/2019 | Panousis et al. |
| 2020/0129600 A1 | 4/2020 | Nolte et al. |

FOREIGN PATENT DOCUMENTS

| | | |
|---|---|---|
| EP | 0 154 316 B1 | 9/1989 |
| EP | 0 401 384 A1 | 12/1990 |
| EP | 2 497 489 A1 | 9/2012 |
| EP | 2 623 110 A1 | 8/2013 |
| WO | WO 89/11865 | 12/1989 |
| WO | WO 90/08835 | 8/1990 |
| WO | WO 91/17258 | 11/1991 |
| WO | WO 92/16221 | 10/1992 |
| WO | WO 95/34326 | 12/1995 |

(Continued)

OTHER PUBLICATIONS

Albrecht et al., JAMA Intern Med. Aug. 2014;174(8):1244-51. doi: 10.1001/jamainternmed.2014.2534.*
Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Janeway et al., Immunobiology, 3rd edition, Garland Publishing Inc., 1997, pp. 3:1-3:11.*
Rudikoff et al., Proc Natl Acad Sci USA. Mar. 1982;79(6):1979-83.*
Grandin, T., Journal American Veterinary Medical Association, 1994 vol. 204, pp. 1354-1360.*
Terasawa, Hidetoshi, et al., "Recent trend of human blood coagulation factor XII," 2014, pp. 411-422 2014_Kessen-Shikestu-Shi_JpnJThrombHemost_25_3_411-22.

(Continued)

*Primary Examiner* — Michael Szperka
(74) *Attorney, Agent, or Firm* — Finnegan, Henderson, Farabow, Garrett and Dunner LLP

(57) ABSTRACT

The present invention relates to the use of a direct Factor XII (FXII) inhibitor in the treatment of a neurotraumatic disorder resulting from a traumatic injury of the brain (traumatic brain injury, TBI) or the spinal cord (spinal cord injury, SCI).

18 Claims, 26 Drawing Sheets

Specification includes a Sequence Listing.

(56) References Cited

FOREIGN PATENT DOCUMENTS

| WO | WO 01/79271 A1 | 10/2001 | | |
|---|---|---|---|---|
| WO | WO 03/076567 A2 | 9/2003 | | |
| WO | WO 2004/101740 A2 | 11/2004 | | |
| WO | WO 2005/000892 A2 | 1/2005 | | |
| WO | WO 2005/000892 A3 | 1/2005 | | |
| WO | WO 2005/001025 A2 | 1/2005 | | |
| WO | WO 2005/001025 A3 | 1/2005 | | |
| WO | WO 2005/024044 A2 | 3/2005 | | |
| WO | WO 2005/024044 A3 | 3/2005 | | |
| WO | WO 2005/063808 A1 | 7/2005 | | |
| WO | WO 2006/066878 A1 | 6/2006 | | |
| WO | WO 2008/098720 A1 | 8/2008 | | |
| WO | WO 2011/069090 A1 | 6/2011 | | |
| WO | WO 2012 083024 A1 | 6/2012 | | |
| WO | WO 2013/014092 A1 | 1/2013 | | |
| WO | WO-2013014092 A1 | * | 1/2013 | ......... A61K 39/3955 |
| WO | WO 2014/135694 A1 | 9/2014 | | |
| WO | WO 2014/207199 A1 | 12/2014 | | |
| WO | WO-2014207199 A1 | * | 12/2014 | ......... A61K 31/4365 |

OTHER PUBLICATIONS

Mao, Gordon, "Traumatic Brain Injury (TBI)," MSD Manual Professional Version, Jun. 2021, 15 pages.
C1S complement C1s [ Homo sapiens (human), NCBI, Gene ID: 716, updated on Jan. 25, 2022, (https://www.ncbi.nlm.nih.gov/gene/716).
Akita et al., "Structure and function of antithrombin", (Jap. J. Thrombosis and Hemostasis (in Japanese), 2014, vol. 25, No. 1, pp. 23-32.
Kennedy et al., "Effects of Protease Inhibitors on Radiation Transformation in Vitro" Cancer Research, 1981, vol. 41, pp. 2103-2108.
Bramlett, M. H., et al., "Pathophysiology of cerebral ischemia and brain trauma: Similarities and differences," *Journal of Cerebral Blood Flow & Metabolism*, 2004; 24: 133-150.
Burke, F. J. et al., "Traumatic brain injury may be an independent risk factor for stroke," *American Academy of Neurology*, 2013, 91: 33-39.
Cunningham, S. A. et al., "Physiological thresholds for irreversible tissue damage in contusional regions following traumatic brain injury," *Brain*, 2005; 128: 1931-1942.
Dewitt, S. D. et al., "Traumatic cerebral vascular injury: The effects of concussive brain injury on the cerebral vasculature," *Journal of Neurotrauma*, 2003; 20(9): 795-825.
Lee, Y. et al., "Increased risk of ischemic stroke in patients with mild traumatic brain injury: a nationwide cohort study," *Scandinavian Journal of Trauma, Resuscitation and Emergency Medicine* 2014, 22:66 (7 pages).
Núñez, T. M.et al., "Iron toxicity in neurodegeneration," *Biometals*, 2012; 25:761-776.
Rodríguez-Baeza, A. et al., "Morphological features in human cortical brain microvessels after head injury: A Three-Dimensional and Immunocytochemical Study," *The Anatomical Record Part A*, 2003; 273A: 583-593.
Urrutia, J. P. et al., "The interplay between iron accumulation, mitochondrial dysfunction, and inflammation during the execution step of neurodegenerative disorders," *Frontiers in Pharmacology*, 2004; 5(28): 1-12.
Albert-Weissenberger, C., et al., "An experimental protocol for mimicking pathomechanisms of traumatic brain injury in mice," Experimental & Translational Stroke Medicine, 2012; 4:1-5.
Albert-Weissenberger, C., et al., "Blocking of bradykinin receptor B1 protects from focal closed head injury in mice by reducing axonal damage and astroglia activation," Journal of Cerebral Blood Flow & Metabolism, 2012; 32:1747-1756.
Albert-Weissenberger, C., et al., "C1-Inhibitor protects from focal brain trauma in a cortical cryolesion mice model by reducing thrombo-inflammation," Frontiers in Cellular Neuroscience, 2014: 8: Article 269 (10 pages).
Albert-Weißenberger, C. et al., "Ischemic stroke and traumatic injury: The role of the kallikrein-kinin system," Progress in Neurobiology, 101-102 (2013) 65-82.
Albrecht, J., et al., "Benefits and Risks of Anticoagulation Resumption Following Traumatic Brain Injury," JAMA Intern Med. 2014; 174(8):1244-1251.
Austinat, M, et al., "Blockade of Bradykinin Receptor B1 but Not Bradykinin Receptor B2 Provides Protection From Cerebral Infarction and Brain Edema," Stroke, 2009; 40:285-293.
Beattie, W., et al., "Structure and evolution of human α-fetoprotein deduced from partial sequence of cloned cDNA," Gene, 1982; 20:415-422.
Campos, I, et al., "Identification and characterization of a novel factor XIIa inhibitor in the hematophagous insect, *Triatoma infestans* (Hemiptera: Reduviidae)," FEBS Letters, 2004; 577:512-516.
Campos, I.T.N., et al., "Infestin, a Thrombin Inhibitor presents in *Triatoma infestans* midgut, a Chagas' disease vector: gene cloning, expression and characterization of the inhibitor," Insect Biochemistry and Molecular Biology, 2002; 32:991-997.
Choudhri, T., et al., "Use of a Spectropotometric Hemoglobin Assay to Objectively Quantify Intracerebral Hemorrhage in Mice," Stroke, 1997; 28(11):2296-2302.
Cooke, N., et al., "Serum Vitamin D-binding Protein is a Third Member of the Albumin and Alpha Fetoprotein Gene Family," J. Clin. Invest., 1985; 76:2420-2424.
Devereaux, J., et al., "A comprehensive set of sequence analysis programs for the VAX," Nucleic Acids Research, 1984; 12(1): 387-395.
Donkin, J., et al., "Mechanisms of Cerebral edema in traumatic brain injury: therapeutic developments," Curr Opin Neurol, 2010; 23:293-299.
Doppenberg, E, et al., "Clinical Trials in Traumatic Brain Injury: Lessons for the Future," J Neurosurg Anesthesiol, 2004; 16(1):87-94.
Dudley, R., et al., "Early Venous Thromboembolic Event Prophylaxis in Traumatic Brain Injury with Low-Molecular-Weight Heparin: Risks and Benefits," Journal of Neurotrauma, 2010; 27:2165-2172.
Edwards et al., "The remarkable flexibility of the human antibody repertoire; isolation of over one thousand different antibodies to a single protein, BLyS," J. Mol Biol. Nov. 14, 2003;334(1): 103-18.
EU Directive on the protection of animals used for scientific purposes, Official Journal of the European Union, 2010; L 276:33-79.
European Search Report, European Patent Application No. 14172910.3, dated Dec. 5, 2014 (9 pages).
Faul, M., et al., "Using a Cost-Benefit Analysis to Estimate Outcomes of a Clinical Treatment Guideline: Testing the Brain Trauma Foundation Guidelines for the Treatment of Severe Traumatic Brain Injury," The Journal of TRAUMA® Injury, Infection, and Critical Care, 2007; 63(6):1271-1278.
Francis, G., "Protein modification and fusion proteins," Focus on Growth Factors, 1992;3(2): 4-10.
Gailani, D., et al., "A murine model of factor XI deficiency," Blood Coagulation and Fibrinolysis, 1997; 8:134-144.
Goel et al., "Plasticity within the antigen-combining site may manifest as molecular mimicry in the humoral immune response," J Immunol. Dec. 15, 2004; 173(12): 7358-67.
Grandin, T. et al., "Euthanasia and slaughter of livestock," Journal American Veterinary Medical Association, 1994 vol. 204, pp. 1354-1360.
Hagedorn, I., et al., "Factor XIIa Inhibitor Recombinant Human Albumin Infestin-4 Abolishes Occlusive Arterial Thrombus Formation Without Affecting Bleeding," Circulation, 2010, 121:1510-1517.
Harhangi, B.S., et al., "Coagulation disorders after traumatic brain injury," Acta Neurochir (Wein), 2008; 150:165-175.
International Search Report and Written Opinion, International Patent Application No. PCT/EP2015/063760, mailed Oct. 6, 2015 (13 pages).
Kabadi, S., et al., "Neuroprotective Strategies for Traumatic Brain Injury: Improving Clinical Translation," Int. J. Mol. Sci., 2014; 15:1216-1236.

(56) References Cited

OTHER PUBLICATIONS

Kilkenny, C., et al., "Improving bioscience research reporting: the ARRIVE guidelines for reporting animal research," Osteoarthritis and Cartilage, 2012; 20:256-260.

Kim, L., et al., "Early initiation of prophylactic heparin in severe traumatic brain injury is associated with accelerated improvement on brain imaging," Journal of Emergencies, Trauma, and Shock, 2014; 17(3):141-148.

Kleinschnitz, C., et al., "Targeting coagulation factor XII provides protection from pathological thrombosis in cerebral ischemia without interfering with hemostasis," JEM, 2006; 203(3):513-518.

Langhauser, F., et al., "Kininogen deficiency protects from ischemic neurodegeneration in mice by reducing thrombosis, blood-brain barrier damage, and inflammation," Blood, 2012; 120(19):4082-4092.

Laskowski, M., et al., "Protein Inhibitors of Proteinases," Ann. Rev. Biochem., 1980, 49:593-626.

Leeb-Lundberg, L.M., et al., "International Union of Pharmacology. XLV. Classification of the Kinin Receptor Family: from Molecular Mechanisms to Pathophysiological Consequences," Pharmacol Rev, 2005; 57(1):27-77.

Lichenstein, H., et al., "Afamin Is a New Member of the Albumin, α-Fetoprotein, and Vitamin D-binding Protein Gene Family," The Journal of Biological Chemistry, 1994; 269(27):18149-18154.

Llyod et al., "Modelling the human immune response: performance of a $10^{11}$ human antibody repertoire against a broad panel of therapeutically relevant antigens," Protein Eng Des Sel. Mar. 2009;22(3): 159-68. doi: 10.1093/protein/gzn058. Epub Oct. 29, 2008.

Maegele, M., "Coagulopathy after traumatic brain injury; incidence, pathogensis, and treatment options," Transfusion, 2013; 53:28S-37S.

Malik, F., et al., "Polyethylene Glycol (PEG)-modified Granulocyte-Macrophage Colony-stimulating Factor (GM-CSF) with Conserved Biological Activity," Exp. Hematol, 1992; 20:1028-1035.

Menon, D, et al., "Progress, failures and new approaches for TBI research," Nat. Rev. Neurol., 2015; 11:71-72.

Nahrendorf et al., "Activatable Magnetic Resonance Imaging Agent Reports Myeloperoxidase Activity in Healing Infarcts and Noninvasively Detects the Antiinflammatory Effects of Atorvastatin on Ischemia-Reperfusion Injury," Circulation, 2010; 117:1153-60.

Narayan, R, et al., "Clinical Trials in Head Injury," J. Neurotrauma, 2002; 19(5):503-557; PMC Author Manuscript (77 pages).

Nuijens, J., et al., "Activation of the Contact System of Coagulation by a Monoclonal Antibody Directed Against a Neodeterminant in the Heavy Chain Region of Human Coagulation Factor XII (Hageman Factor)," The Journal of Biological Chemistry, 1989; 264(22):12941-12949.

Ongali, B., et al., "Autoradiographic Analysis of Mouse Brain Kinin $B_1$ and $B_2$ Receptors after Closed Head Trauma and Ability of Anatibant Mesylate to Cross the Blood-Brain Barrier," Journal of Neurotrauma, 2006; 23(5):696-707.

Pauer, H, et al., "Targeted deletion of murine coagulation factor XII gene-α model for contact phase activation in vivo," Thromb Haemost, 2004; 92:503-508.

Peck, K., et al., "The impact of preinjury anticoagulants and prescription antiplatelet agents on outcomes in older patients with traumatic brain injury," J Trauma Acute Care Surg, 2014; 76(2):431-436.

Pixley, R., et al., "A Monoclonal Antibody Recognizing an Icosapeptide Sequence in the Heavy Chain of Human Factor XII Inhibits Surface-catalyzed Activation," The Journal of Biological Chemistry, 1987; 262(21):10140-10145.

Raslan, F., et al., "Inhibition of bradykinin receptor B1 protects mice from focal brain injury by reducing blood-brain barrier leakage and inflammation," Journal of Cerebral Blood Flow & Metabolism, 2010; 30:1477-1486.

Ravon, D., et al., "Monoclonal Antibody F1 Binds To the Kringle Domain of Factor XII and Induces Enhanced Susceptibility for Cleavage by Kallikrein," Blood, 1995; 86(11): 4134-4143.

Rosenthal, R., et al., "Plasma Thromboplastin Antecedent (PTA) Deficiency: Clinical, Coagulation, Therapeutic and Hereditary Aspects of a New Hemophilia-like Disease," Blood, 1955; 10(2):120-131.

Rudikoff et al., "Single amino acid substitution altering antigen-binding specificity," Proc Natl Acad Sci USA. Mar. 1982;79(6): 1979-83.

Schwarzmaier, S., et al., "Temporal Profile of Thrombogenesis in the Cerebral Microcirculation after Traumatic Brain Injury in Mice," Journal of Neurotrauma, 2010; 27:121-130.

Shlosberg, D., et al., "Blood-brain barrier breakdown as a therapeutic target in traumatic brain injury," Nat Rev Neurol, 2010; 6(7):393-403; PMC Author Manuscript (23 pages).

Small, E., et al., "A Monoclonal Antibody That Inhibits Activation of Human Hageman Factor (Factor XII)," Blood, 1985; 65(1):202-210.

Stein, S., et al., "Association between Intravascular Microthrombosis and Cerebral Ischemia in Traumatic Brain Injury," Neurosurgery, 2004; 54(3):687-691.

Stein, S., et al., "Intravascular coagulation: a major secondary insult in nonfatal traumatic brain injury." J. Neurosurg., 2002; 97:1373-1377.

Steudel, W.I., et al., "Epidemiology and prevention of fatal head injuries in Germany—trends and the impact of the reunification," Acta Neurochir (Wien), 2005; 147:231-242.

Stutzmann, J., et al., "Neuroprotective Profile of Enoxaparin, a Low Molecular weight Heparin, in In Vivo Models of Cerebral Ischemia or Traumatic Brain Injury in Rats: a Review," CNS Drug Reviews, 2002; 8(1):1-30.

Tagliaferri, F., et al., "A systematic review of brain injury epidemiology in Europe," Acta Neurochir (Wein), 2006; 148:255-268.

Trabold, R., et al., "The role of bradykinin $B_1$ and $B_2$ receptors for secondary brain damage after traumatic brain injury in mice," Journal of Cerebral Blood Flow & Metabolism, 2010; 30:130-139.

U.S. Appl. No. 15/318,550; Requirement for Restriction/Election, mailed Nov. 23, 2018 (8 pages).

U.S. Appl. No. 15/318,550; Non-final Rejection, mailed Apr. 30, 2019 (18 pages).

Wagner, S., et al., "Activation of the tissue kallikrein-kinin system in stroke," Journal of the Neurological Sciences, 2002; 202:75-76.

Werle, M., et al., "Strategies to improve plasma half life time of peptide and protein drugs," Amino Acids, 2006; 30:351-367.

Wright, D., et al., Gender Differences in Neurological Emergencies Part II: A Consensus Summary and Research Agenda on Traumatic Brain Injury, Acad Emerg Med., 2014; 21(12):1414-1420; PMC Author Manuscript (12 pages).

* cited by examiner

A

B

C

A

CD11b+ - staining

A

B

THERAPY USING A FACTOR XII INHIBITOR IN A NEUROTRAUMATIC DISORDER

This application is a continuation of application Ser. No. 15/318,550, having a 35 U.S.C. § 371(c) date of Dec. 13, 2016, which is the national stage entry under 35 U.S.C. § 371 of International Application No. PCT/EP2015/063760, filed Jun. 18, 2015, which claims priority to European Patent Application No. 14172910.3, filed Jun. 18, 2014. The contents of these applications are each incorporated herein by reference in their entirety.

This application relates to the use of a direct Factor XII (FXII) inhibitor in the treatment of a neurotraumatic disorder selected from a spinal cord injury (SCI) and a traumatic brain injury (TBI).

Two converging pathways for coagulation exist that are triggered by either "extrinsic" (vessel wall) or "intrinsic" (blood-borne) components of the vascular system. The "intrinsic" or contact activation pathway is initiated when Factor XII (FXII, Hageman factor) comes into contact with negatively charged surfaces in a reaction involving high molecular weight kininogen and plasma kallikrein. Factor XII is a serine protease and, once activated (FXIIa), it further activates circulating FXII in a positive feedback reaction (directly or via activation of prekallikrein). FXIIa also activates Factor XI and blood coagulation proceeds in a reaction cascade involving the activation of further factors by limited proteolysis culminating in the generation of thrombin, which converts plasma fibrinogen to fibrin and activates platelets.

The kallikrein-kinin system (KKS) is also initiated by blood coagulation factor XII (FXII, Hageman factor) and plays an important role in the regulation of vascular permeability and edema formation (Leeb-Lundberg et al. (2005) *Pharmacol. Rev.;* 571:27-77). The activation of the KKS was recently proven also in stroke patients (Wagner et al. (2002) *J. Neurol. Sci.;* 202:75-76). Kinins (e. g. bradykinin, kallidin) constitute the end products of the KKS. Kinins are highly active proinflammatory peptide hormones which are released by kallikreins from their precursors, kininogens, during various kinds of tissue injury including brain ischemia. The cellular effects of kinins are mediated by two different bradykinin receptors, B1R and B2R. Activation of these receptors triggers inflammatory processes in the target organ such as the release of proinflammatory cytokines or the attraction of immune cells as well as increased vascular permeability.

Traumatic brain injury (TBI) is a devastating neurological condition and can be defined as brain damage resulting from rapid movement of the brain within the skull or direct injury to the brain and/or nerve roots due to a traumatic event causing immediate mechanical disruption of brain tissue/nerve roots and delayed pathogenic events. It is a heterogeneous disorder that can vary in the type of brain injury, distribution of brain damage and mechanisms of damage. The traumatic event is often caused by traffic or sport accidents, and is the leading cause of death and disability in adolescent and young males (Tagliaferri et al., 2006, *Acta Neurochir (Wien)*, 148(3):255-68). TBI constitutes approximately 20% of all traumas, and has a very high disease-associated spending ($60 billion in the TBI United States in 2000). Further, treatment options for TBI are very limited (Faul et al., 2007, *Journal of Trauma—Injury Infection & Critical Care*, 63(6), 1271-8; Steudel et al., 2005, *Acta Neurochir (Wien)*, 147(3):231-42); at present, the only effective method to treat severe TBI is to prevent its occurrence. Although several phase-II clinical trials have shown favorable effects of therapeutic compounds (Narayan et al., 2002, *J Neurotrauma*, 19(5):503-57), unfortunately all the compounds have failed to clearly show efficacy in phase-III trials (Doppenberg et al., 2004, *Neurosurg Anesthesiol.*, 16(1):87-94). Despite numerous clinical trials, attempts to find a safe and effective neuroprotective agent have all failed (Kabadi et al., 2014, *International journal of molecular sciences* 15:1216-1236; Menon et al., 2015, *Nature reviews Neurology* 11:71-72).

The primary brain damage that occurs due to an outside force causes irreversible mechanical disruption of brain tissue. In the sequel, secondary injury processes contribute to the exacerbation of traumatic brain damage. The primary brain tissue damage can be diffuse or focal, whereby the circumstances of injury determine the relative degree to which diffuse and focal trauma develops. While focal trauma is associated with brain tissue contusion, vascular injury, and hemorrhage, accompanied by ischemia, diffuse brain injury is characterized by diffuse axonal injury. Key contributing factors to the brain damage are inflammation, metabolic disturbances and cerebrovascular dysfunction which further propagates injury-induced tissue ischemia and brain edema due to breakdown of the blood-brain-barrier (BBB) (Schlosberg et al. (2010) *Nat Rev Neurol.;* 6:393-403; Donkin and Vink (2010) *Curr. Opinion in Neurol.;* 23:293-299).

Beyond well-characterized injury processes like excitotoxicity, inflammation and blood-brain barrier damage, thrombus formation in the cerebral microcirculation probably contributes to secondary brain damage by causing peri-contusional ischemia and reducing regional cerebral blood flow (Schwarzmaier et al., 2010, *J Neurotrauma* 27:121-130). In clinical TBI, intracerebral vessel occlusion with subsequent ischemia worsens the outcome (Stein et al., 2002, *J Neurosurg* 97:1373-1377; Stein et al., 2004, *Neurosurgery* 54:687-691; Harhangi et al., 2008, *Acta Neurochir (Wien)* 150:165-175; Maegele, 2013, *Transfusion* 53 Suppl 1:28S-37S). However, a potential use of conventional anticoagulants in TBI patients is discussed controversially. Some studies support a net beneficial effect of anticoagulation following TBI by reducing the risk of thromboembolic events (Dudley et al., 2010, *J Neurotrauma* 27:2165-2172; Albrecht et al., 2014, *JAMA internal medicine* 174:1244-1251) and improving outcome parameters (Stutzmann et al., 2002, *CNS Drug Rev* 8:1-30; Kim et al., 2014, *J Emerg Trauma Shock* 7:141-148) while other studies report a detrimental effect of anticoagulation (Peck et al., 2014, *The journal of trauma and acute care surgery* 76:431-436) due to an increased risk of intracranial hemorrhages that also occur frequently after TBI.

The kallikrein-kinin system (KKS) is implicated in multiple pathological states (Leeb-Lundberg et al. (2005) *Pharmacol. Rev.;* 571:27-77), and represents an attractive therapeutic target in TBI. Kinins, liberated by the kallikreins, are proinflammatory peptides that mediate their effects via activation of two G-protein-coupled receptors (GPCR), kinin receptor B1 (B1R) and B2 (B2R) (Leeb-Lundberg et al., 2005, *Pharmacol. Rev.;* 571:27-77; (Albert-Weissenberger et al. (2013) *Progr. Neurobiol.;* 101-102:65-82). Kinins play an important role in regulating vascular permeability, edema formation, transendothelial cell migration, and inflammation in different organs following injury (Leeb-Lundberg et al., 2005, *Pharmacol. Rev.;* 571:27-77). Moreover, the KKS is linked to the plasmatic coagulation cascade via factor XII (FXII, Hageman factor). All constituents of the KKS have been identified in the rodent and human brain (Albert-Weissenberger et al. (2013) *Progr. Neurobiol.;* 101-102:65-

82), and their expression is upregulated following brain injury (Ongali et al. (2006) *J. Neurotrauma* 23, 696-707; Raslan et al., (2010) *J. Cereb. Blood Flow Metab.* 30, 1477-1486; Trabold et al. (2010), *J. Cereb. Blood Flow Metab.* 30, 130-139.). Recently in mice, blockade of B1R, but not B2R, was shown to reduce blood-brain-barrier damage and edema formation in experimental models of focal cerebral ischemia (Austinat et al. (2009) *Stroke;* 40:285-293) and traumatic brain injury (Albert-Weissenberger et al. (2012) *J. Cereb. Blood Flow Metab.;* 32:1747-56; Raslan et al. (2010) *J. Cereb. Blood Flow Metab.;* 30:1477-1486) suggesting functional relevance of the KKS on brain edema formation in the acute phase of ischemic stroke and traumatic brain injury (Albert-Weissenberger et al. (2013) *Progr. Neurobiol.;* 101-102:65-82).

In studies preventing the activation of KKS via inhibition of FXII, which is activated physiologically upon contact with negatively charged surfaces (contact activation), neuropathological outcome following acute experimental stroke was investigated (Hagedorn et al. (2010) *Circulation;* 121: 1510-1517; Kleinschnitz et al. (2006) *JEM;* 203(3):513).

WO 2006/066878 discloses for the first time in general the use of a FXII inhibitor in treating or preventing venous or arterial thrombosis without being associated with abnormal bleeding (hemostasis).

Hagedorn et al. ((2010) *Circulation;* 121:1510-1517) discloses the treatment and prevention of occlusive arterial thrombus formation by recombinant human albumin Infestin-4, a FXII inhibitor, while leaving hemostasis fully intact. Furthermore rHA-Infestin-4 was protective in a murine model of ischemic stroke.

EP 2 623 110 A1 discloses FXII inhibitors for the treatment of neurological inflammatory disorders. Although the term "neurological inflammatory disease" refers to a condition with an inflammation of one or more areas of brain or spinal cord this disorder is not linked to traumatic brain injury or spinal cord injury.

WO 2014/135694 (published on 12 Sep. 2014) discloses a contact activation system selected from C1 esterase inhibitor, a kallikrein inhibitor and a FXII inhibitor, for use in the treatment and/or prevention of remote ischemia-reperfusion injury (IRI). Although such a remote IRI may include disruption of blood brain barrier, the mentioned diseases and effects (cerebral edema, stroke, increased intracranial pressure and inflammation of neuronal tissue) as well as the remote IRI itself are not unambiguously linked to traumatic brain injury or spinal cord injury.

WO 2011/069090 discloses the treatment of a disease or condition associated with FXII activation by administering a phosphatidylserine binding agent, i.e. an inhibitor of an activator of FXII. It is mentioned that inhibition of FXII activation can e.g. be useful in preventing and treating (neurogenic) shock caused by e.g. spinal cord trauma. Although WO 2011/069090 also mentions shortly that a phosphatidylserine binding agent can be combined with an anti-FXII antibody the efficacy of a direct FXII inhibitor (alone or in combination) in spinal cord trauma or in traumatic brain injury is unproven.

In summary there is state of the art disclosing the use of a FXII inhibitor either in particular thrombotic indications or inflammatory diseases or neurological conditions. But none of these documents is related to a disease with the pathomechanism which is relevant in neurotraumatic disorders. Additionally, specific therapeutic interventions for traumatic brain injury are lacking in the state of the art and there is still a pressing demand to identify innovative pathomechanism-based concepts for effective therapies, in particular in view of the controversial discussions of anticoagulant treatment in TBI patients.

Hence, in traumatic brain injury, it is apparent that there still exists a need for an improved medication for the treatment of a traumatic brain injury. Therefore, it is an object of the present invention to satisfy such a need. Thus, the technical problem underlying the present invention was to provide alternative and/or improved means and methods for successfully targeting traumatic brain injury that form the basis or may allow the development of more satisfactory therapeutics for the treatment of traumatic brain injury.

The solution to this technical problem is achieved by providing the embodiments characterized in the claims.

Accordingly, disclosed herein are therapies comprising the use of at least one direct Factor XII inhibitor (FXII inhibitor) in the treatment of a neurotraumatic disorder. The neurotraumatic disorder is resulting from a traumatic injury of the central nervous system and can be selected from spinal cord injury and traumatic brain injury, and therapy can comprise administering an effective amount of at least one FXII inhibitor (e.g., rHA-Infestin-4 or anti-FXII antibody).

In other words, the inventors have discovered that a traumatic brain injury or a spinal cord injury occurring after an initial traumatic injury of the central nervous system, in particular a traumatic edema, could be treated and/or prevented by the administration of a direct FXII inhibitor. Accordingly, in general the present invention relates to a direct FXII inhibitor for use in a method of treating a traumatic injury and/or treating or preventing the formation and/or reducing the size of a primary edema of the central nervous system (CNS) in a subject wherein the subject, preferably a human subject, has or has had at least one disorder selected from the group consisting of traumatic brain injury, and spinal cord injury.

The inventors have found that pharmacological inhibition of FXII with a direct FXII inhibitor minimizes trauma-induced microvascular thrombus formation after traumatic brain injury and improves functional outcome such as better motor function, reduced brain lesion volume, and diminished neurodegeneration without increasing the risk of abnormal intracerebral bleedings.

In some embodiments, the at least one FXII inhibitor can comprise a wild type Infestin-4 polypeptide sequence (SEQ ID NO: 1) or an Infestin-4 sequence harboring 1-5 amino acid mutations outside of N-terminal amino acid positions 2-13 of SEQ ID NO: 1 and/or a homology of at least 70%, 80%, 85%, 90%, 95%, 98%, or 99% to SEQ ID NO: 1 and retaining six conserved cysteine residues from SEQ ID NO: 1. In some embodiments, the at least one FXII inhibitor can comprise a wild-type SPINK-1 polypeptide sequence (SEQ ID NO: 2), or a wild-type SPINK-1 polypeptide sequence in which N-terminal amino acid positions 2-13 have been replaced with the N-terminal amino acids 2-13 of SEQ ID NO: 1; and optionally further modified to contain 1-5 additional amino acid mutations that increase the homology of the polypeptide sequence to the sequence of SEQ ID NO: 1, and/or a homology of at least 70%, 80%, 85%, 90%, 95%, 98%, or 99% to SEQ ID NO: 2 and retaining six conserved cysteine residues from SEQ ID NO: 2. In certain embodiments, the at least one FXII inhibitor can comprise an anti-FXII antibody. In some embodiments, the at least one FXII inhibitor can be linked to a fusion partner (e.g., a half-life enhancing polypeptide) either directly or via a linker. In some embodiments the FXII inhibitor is specific to FXII, FXIIa and/or the activation of FXII.

In various embodiments, the FXII inhibitor is administered immediately after the neurotraumatic injury of a patient or after a patient develops the neurotraumatic disorder, or it is administered prophylactically. The FXII inhibitor can be administered once, or multiple times (e.g., as a repeated prophylactic treatment, or as a repeated treatment during or following the traumatic injury resulting in the neurotraumatic disorder).

In some embodiments, a kit is provided, comprising at least one FXII inhibitor, instructions for using the kit in the treatment of a neurotraumatic disorder, and optionally, at least one further therapeutically active compound or drug, wherein the further therapeutically active compound is not C1 inhibitor.

DETAILED DESCRIPTION OF CERTAIN EMBODIMENTS

Figure 1:
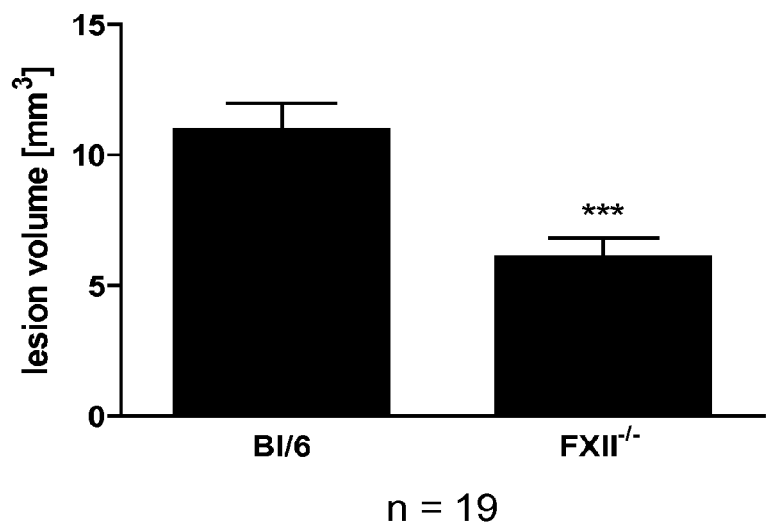
FIG. 1 shows a reduced lesion size in rHA-Infestin-4 treated wild-type (WT) mice or $FXII^{-/-}$ mice compared to NaCl-treated or WT controls, respectively, 24 h after trauma induction. TTC stainings of brain slices gained from male and female mice were analyzed for their lesion volume. FXII deficiency or inhibition reduces lesion sizes 24 h after trauma induction.
Figure 1:
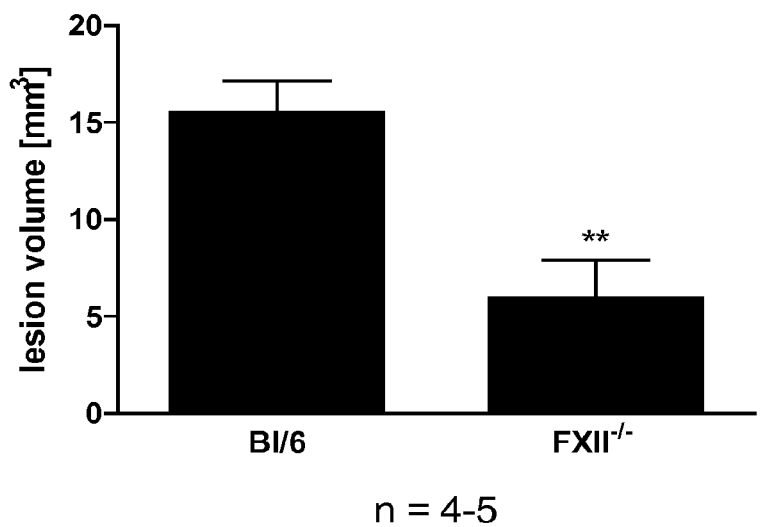
Figure 1:
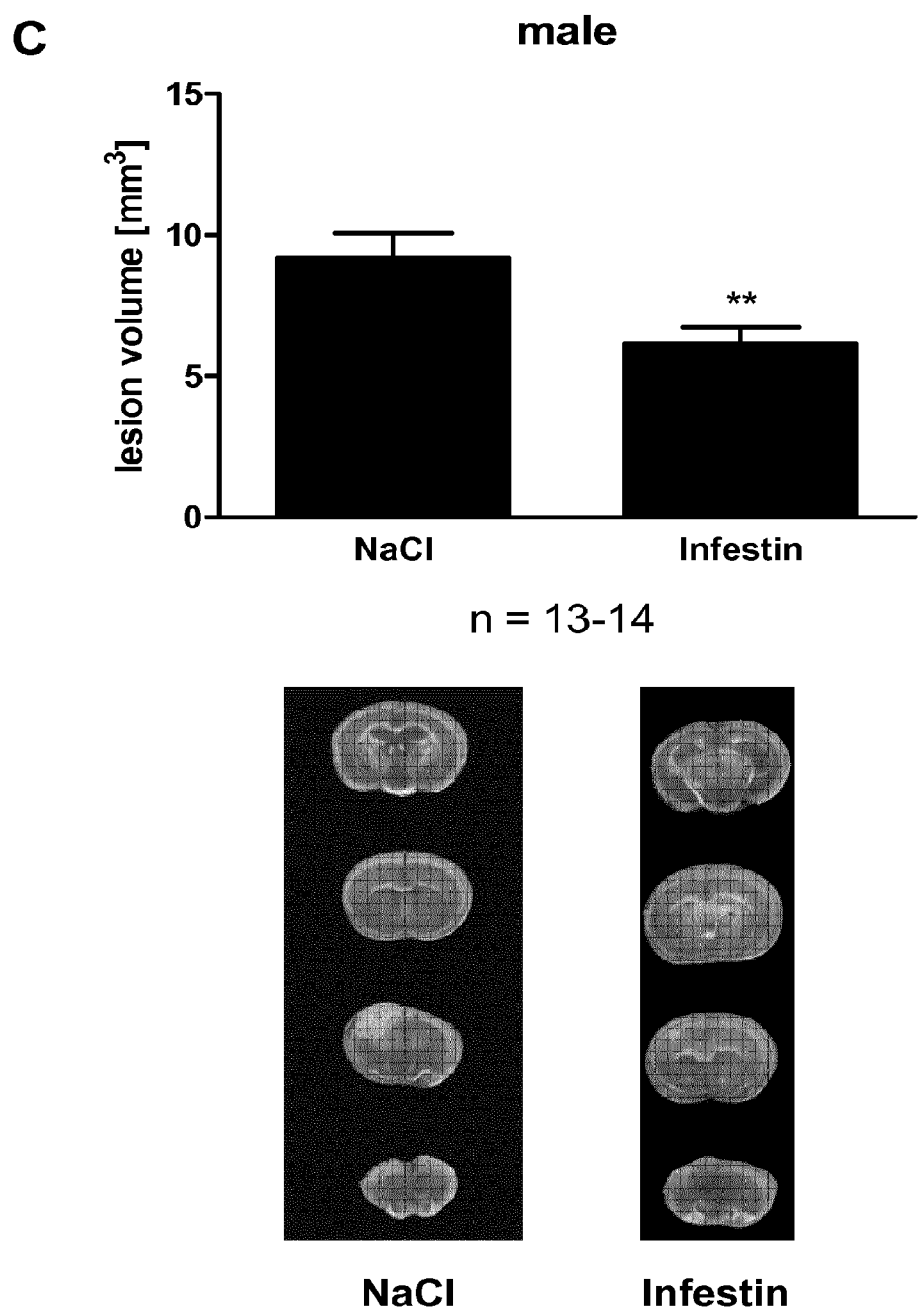

The embodiments of the application pertain to methods comprising administering a direct Factor XII (FXII) inhibitor to a patient to treat a neurotraumatic disorder selected from a spinal cord injury and a traumatic brain injury. In some embodiments, this therapy can interact with multiple pathways underlying the pathophysiology of the treated diseases, e.g. thrombo-inflammation, cytotoxic and vascular brain edema, microvascular perfusion deficit due to vasospasms and microthrombus formation, damage to the microvascular endothelium and components of the blood-brain barrier, potentially providing more effective treatment to a broader range of patient populations compared to the treatment therapies in the prior art.

Definitions

In this application, the use of the singular (such as "a" or "the") includes the plural unless specifically stated otherwise. Also in this application, the use of "or" means "and/or" unless stated otherwise. Furthermore, the use of the term "including", as well as other forms, such as "includes" and "included", are not limiting. Any range described here will be understood to include the endpoints and all values between the endpoints.

The section headings are for organizational purposes only and are not to be construed as limiting the subject matter described. All documents or portions of documents cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

As used herein, a "FXII inhibitor" refers to an inhibitor of either or both of Factor XII (prior to activation, i.e. its zymogen) and activated Factor XII (FXIIa) as well as to the activation of FXII. FXII inhibitors encompass functional variants and fragments of the wild-type inhibitor. A functional variant or fragment is a molecule that retains at least 50% (e.g., 50, 60, 70, 80, 90, 95, 99, or 100%, or any percentage in between) of the ability of the wild-type molecule to inhibit FXII, FXIIa or the activation of FXII.

The term "direct FXII inhibitor", as used herein, refers to an inhibitor that acts via contact (e.g., binding) with FXII (or FXIIa), i.e., the FXII inhibitor binds to FXII and/or FXIIa and inhibits its activity and/or activation. In contrast, an indirect inhibitor may act without contacting FXII (or FXIIa) protein. For example, antisense RNA can be used to decrease expression of the FXII gene, or a small molecule can inhibit the effects of FXIIa via interactions with downstream FXIIa reaction partners like Factor XI; these do not interact directly with the FXII protein. Thus, an indirect inhibitor, in contrast to a direct inhibitor, acts upstream or downstream from the FXII protein. Some examples of direct inhibitors are presented below. In some embodiments, the FXII inhibitors are non-endogenous inhibitors; that is, they are not inhibitors that occur naturally in the human or animal body. In some embodiments, the FXII inhibitors are specific to FXII or FXIIa, in particular specific to human FXII or FXIIa as discussed below.

A "neurotraumatic disorder", as used herein, refers to a traumatic injury of the central nervous system (CNS), selected of a spinal cord injury and a traumatic brain injury.

Preferably the neurotraumatic disorder is a primary traumatic brain edema, which is an edema occurring during the initial insult or shortly or immediately (i.e. within minutes) after the insult. Accordingly, a neurotraumatic disorder or an edema of CNS refers to any direct brain or spinal cord swelling i.e. the swelling occurs immediately after the initial injury. It is initially a vasogenic edema resulting from increased water diffusion over the damaged blood brain barrier but later also a cytotoxic edema resulting from abnormal water uptake by injured brain cells. A neurotraumatic disorder further implies direct neural injury (apoptosis, axonal damage), local brain tissue energy deficit caused by microvascular damage and thrombo-inflammatory processes that occur immediately and last days to months after the insult.

Preferably the neurological disorder according to the invention initially occurs within a few hours after the initial injury (i.e. when the external force injures the CNS) and can persist for weeks. In some embodiments the neurological disorder of CNS appears within 30 minutes or within 1, 2, 3, 4, 5, 6, 12 or 24 h after the initial insult or at any time in between.

Preferably the neurotraumatic disorder according to the invention initially occurs within a few hours after the initial injury (i.e. when the external force injures the CNS) and can persist for weeks. In some embodiments the neurotraumatic disorder of CNS appears within 30 minutes or within 1, 2, 3, 4, 5, 6, 12 or 24 h after the initial insult or at any time in between.

The term "traumatic brain injury" ("TBI") refers to a brain damage resulting from rapid movement of the brain within the skull due to a traumatic event causing immediate mechanical disruption of brain tissue and delayed pathogenic events. It is a heterogeneous disorder that can vary in the type of brain injury, distribution of brain damage and mechanisms of damage. A symptom of the TBI, which appears very often, is a traumatic brain edema. The traumatic event is often caused by traffic or sport accidents.

The term "spinal cord injury" (SCI) as used herein refers to any injury to the spinal cord that is caused by trauma instead of disease. Depending on where the spinal cord and nerve roots are damaged, the symptoms can vary widely, from pain to paralysis to incontinence. Spinal cord injuries are described at various levels of "incomplete", which can vary from having no effect on the patient to a "complete" injury which means a total loss of neurological/organ function. Often the spinal cord injury is associated with a spinal cord edema. Spinal cord injuries have many causes, but are typically associated with major trauma from e.g. motor vehicle accidents, falls, sports injuries, and violence.

The term "traumatic brain edema" or "brain edema" refers to any post-injury swelling of the brain, i.e. the swelling occurs within a short period of time after the initial injury of the CNS. The term "traumatic spinal cord edema" or "spinal cord edema" refers to any post-injury swelling of the spinal cord, i.e. the swelling occurs within a short period of time after the initial injury.

As used here, the terms "treat" and "treating" encompass preventing, inhibiting, eliminating, delaying the onset, slowing, lessening, reducing the severity, or ameliorating at least one sign, symptom, or aspect of a disorder or disease. Treating does not require a complete elimination of symptoms, in that it encompasses but is not equivalent to "cure" or "curing". In some embodiments, a patient can be treated to prevent a disorder, meaning either administering therapy to a subject known to be at risk for developing a neurotraumatic disorder selected from a spinal cord injury and a traumatic brain injury. In some embodiments, "treat" or "treating" can also include ameliorating the effects of a disorder or disease. The terms "ameliorating" and "ameliorating the effects" mean that some aspect of the disorder or disease that produces an impairment of one or more patient function is improved. For example, treating a traumatic brain injury can include preventing a traumatic brain injury, ameliorating the effects of the traumatic brain injury, or reducing the severity of the traumatic brain injury (as measured, e.g., by neurological function or brain imaging).

As used herein, a "patient" is any human or animal that has, has had, or is likely to develop a neurotraumatic disorder selected from a spinal cord injury and a traumatic brain injury and who could benefit from the administration of a FXII inhibitor. The administration of a FXII inhibitor can be by any known method of delivering a pharmaceutical or therapeutic agent to a patient, including, without limitation, parenteral administration (e.g., subdural, subcutaneous, intravenous, intra-arterial, intramuscular, intrathecal, intranasal, intratracheal, inhalative, and/or intraperitoneal injection), oral, and/or rectal administration, as well as administration by instillation, spray application, and/or infusion techniques. In certain embodiments, the administration can be done intravenously, subcutaneously or intrathecally.

As used herein, an "antibody" includes any polypeptide comprising a functional antigen-binding site, including immunoglobulins and antigen-binding parts or fragments thereof. A functional antigen-binding part or fragment is a molecule that retains at least 50% (e.g., 50, 60, 70, 80, 90, 95, 99, or 100%, or any percentage in between) of the ability of the full-length antibody to bind to and inhibit the antigen. The term antibody includes but is not limited to polyclonal, monoclonal, monospecific, polyspecific, non-specific, humanized, fully human, camelized, single-chain, chimeric, synthetic, recombinant, hybrid, mutated, back-mutated, and CDR-grafted antibodies. The term also includes antibody fragments such as Fab, F(ab')2, Fv, scFv, Fd, dAb, VHH (also referred to as nanobodies), and other antibody fragments or variants that retain antigen-binding function, including bi-specific or multi-specific antibodies. An antibody can be of any isotype, including IgA, IgD, IgE, IgG, and IgM. As used herein, an "antigen" is a target molecule that is capable of being bound by an antibody. As used herein, the term "antigen-binding site" refers to the part of an antibody molecule capable binding to or complementary to a part or all of an antigen.

I. Neurotraumatic Disorders

In some embodiments, a FXII inhibitor is disclosed and can be used in methods of treating a neurotraumatic disorder resulting from a traumatic injury of the central nervous system selected from a spinal cord injury and a traumatic brain injury. The methods can comprise administering to a subject in need thereof at least one FXII inhibitor. Accordingly, the invention also provides one or more pharmaceutical compositions comprising at least one FXII inhibitor in pharmaceutically acceptable excipients or carriers for use in treating neurotraumatic disorders resulting from a traumatic injury of the central nervous system and selected from a spinal cord injury and a traumatic brain injury. Similarly, the invention also provides the use of one or more compositions comprising at least one FXII inhibitor in the preparation of a medicament for treating a neurotraumatic disorder selected from a spinal cord injury and a traumatic brain injury. The at least one FXII inhibitor can be used alone or additional therapeutic compounds can also be administered.

A neurotraumatic disorder treated using the methods and compositions disclosed herein can include a spinal cord injury (SCI) or traumatic brain injury (TBI). Preferably the neurotraumatic disorder treated using the methods and compositions disclosed herein is TBI.

A traumatic brain injury (TBI), also known as intracranial injury, according to the present invention occurs when an external force traumatically injures the brain. TBI can be classified based on severity, mechanism (closed or penetrating head injury), or other features (e.g. occurring in a specific location or over a widespread area) and can cause a host of physical, cognitive, social, emotional, and behavioral effects, and outcome can range from complete recovery to permanent disability or death. Traumatic brain injury is defined as damage to the brain resulting from external mechanical force, such as rapid acceleration or deceleration, impact, blast waves, or penetration by a projectile. Brain function is temporarily or permanently impaired and structural damage may or may not be detectable with current technology.

The most common causes of TBI include violence, transportation accidents, construction, and sport accidents. Motor bike accidents are major causes, increasing in significance. In children aged two to four, falls are the most common cause of TBI, while in older children traffic accidents compete with falls for this position. TBI is the third most common injury to result from child abuse. Abuse causes 19% of cases of pediatric brain trauma, and the death rate is higher among these cases.

The type, direction, intensity, and duration of forces all contribute to the characteristics and severity of TBI. Forces that may contribute to TBI include angular, rotational, shear and translational forces. Even in the absence of an impact, significant acceleration or deceleration of the head can cause TBI; however in most cases a combination of impact and acceleration is probably to blame. Forces involving the head striking or being struck by something, termed contact or impact loading, are the cause of most focal injuries, and movement of the brain within the skull, termed noncontact or inertial loading, usually causes diffuse injuries. Damage may occur directly under the site of impact, or it may occur on the side opposite the impact. A TBI according to the invention can be caused by a diffuse injury and/or by a focal injury.

Treatment with at least one FXII inhibitor can be done prophylactically to prevent a neurotraumatic disorder selected from a spinal cord injury and a traumatic brain injury. In most cases the treatment is done after the traumatic injury, i.e. treatment is administered immediately or at some time point after the traumatic injury of the central nervous system occurred resulting in a neurotraumatic disorder selected from a spinal cord injury and a traumatic brain injury. For example, treatment can be administered for the first time directly after the external force injures the central nervous system, or up to about 1 hour, or up to about 2, or even up to 24 hours, or even up to 3 days.

In preferred embodiments, treatment is begun immediately after, or less than about 12 hours after the initial occurrence of the neurotraumatic disorder. In some embodiments, treatment is begun up to about 30 minutes, or up to about 1 hour, up to about 2, or even up to about 24 hours. In some embodiments, treatment is administered immediately after, or about 5, 10, 20, 30, 40, or 50 minutes, or 1, 2, 3, 4, 5, 6, 7, 8, 9, 10, 11, 12, 13, 14, 15, 16, 17, 18, 19, 20, 21, 22, 23 or 24 hours following the occurrence of the external force which traumatically injures the brain or the spinal cord (or at any time point in between). In some embodiments, treatment is administered as soon as possible after the occurrence of the initial injury, and preferably less than 1 hour, less than 6 hours, or less than 24 hours following injury. In some embodiments, treatment occurs no later than about 24 hours following initial injury, or no more than about 6 hours following injury, or no more than about 1 hour following injury.

In some embodiments, administration of at least one FXII inhibitor can be done prophylactically to prevent initial injury in a patient at risk for a neurotraumatic disorder. Prophylactic treatment can be done in a single dose or in repeated doses. Periodic doses can be administered for a set duration of time, for example over the duration of a course of treatment.

In some embodiments, administration of at least one FXII inhibitor can be done repeatedly e.g. to treat a patient at risk for a neurotraumatic disorder or to treat a patient in a more effective manner. Such treatment can be done in multiple doses, for example in two, three, four, five, or more doses in a repeated way, such as a dose every 1 hour, every 2 hours, every 4 hours, every 6 hours, every 12 hours, or any time period in between.

Administration of at least one FXII inhibitor (e.g., to a patient in need of treatment) may occur in a single dose or in repeated administrations, and in any of a variety of physiologically acceptable salt forms, and/or with an acceptable pharmaceutical carrier and/or additive as part of a pharmaceutical composition. Therefore, in certain embodiments, the at least one FXII inhibitor is administered (i)

once, each as a separate injection or infusion, or in a single combined injection or infusion, (ii) in multiple doses, for example in two, three, four, five, or more doses, each as an injection or infusion, or (iii) as an infusion or application. The infusion/application can be administered over a period of time, preferably over a period of 1 minute to 24 hours, or 10 minutes to 12 hours, or 10 minutes to 6 hours, or 10 minutes to 5 hours, or 10 minutes to 4 hours, or 10 minutes to 3 hours, or 10 minutes to 2 hours, or 10 minutes to 1 hour (or any time period in between). The administration can be done in a repeated manner after the insult until the symptoms of the neurotraumatic injury disappear, i.e. administration of at least one FXII inhibitor can occur in repeated administrations for days to months, e.g. for one day, two days, three days, four days, five days, six days, one week, two weeks, four weeks, two months.

The composition comprising at least one FXII inhibitor may be administered to a patient in a therapeutically effective amount. Generally, a therapeutically effective amount may vary with the subject's age, general condition, and gender, as well as the severity of the medical condition in the subject. The dosage may be determined by a physician and adjusted, as necessary, to suit the observed effects of the treatment.

A therapeutically effective dose of the at least one FXII inhibitor may depend on many factors such as, e.g., the exact indication, formulation, or mode of administration, and may be determined in preclinical and clinical trials for each respective indication. For example, in one embodiment, the dose of FXII inhibitor is about 0.01, 0.1, 1, 50, 100, 200, 500, or 1000 mg/kg bodyweight, or any dose in between, or ranging from about 0.01-1000 mg/kg, about 0.1-1000 mg/kg, about 1-1000 mg/kg, about 1-500 mg/kg, about 10-200 mg/kg, about 10-100 mg/kg, about 50-500 mg/kg, about 50-200 mg/kg, or about 100-200 mg/kg, or any dose range in between. In certain embodiments, the FXII inhibitor is rHA-Infestin-4. In some embodiments, when rHA-Infestin-4 is used, the dose may range between about 0.01 and 1000 mg/kg body weight, or between about 1 and 1000 mg/kg, or between about 1 and 500 mg/kg, or between about 50 and 500 mg/kg (or any dose range in between).

In some embodiments, the FXII inhibitor can be an anti-FXII antibody. In those embodiments involving a therapeutically effective dose of an anti-FXII antibody, a therapeutically effective dose is a dose that brings about a positive therapeutic effect in the patient or subject requiring the treatment. A therapeutically effective dose can be in the range of about 0.001 to 100 mg/kg body weight, or from about 0.01 to 100 mg/kg, from about 0.01 to 50 mg/kg, from about 0.1 to 30 mg/kg, from about 0.1 to 10 mg/kg, from about 0.1 to 5 mg/kg, from about 0.1 to 2 mg/kg or from about 0.1 to 1 mg/kg, or any dose range in between. For example, a therapeutically effective dose may be a dose that inhibits FXIIa activity in the subject by at least about 50%, or at least 60%, 70%, 80%, 90%, 95%, 99% or 100% (or any percentage in between).

The exact therapeutically effective dose of the FXII inhibitor may be determined by the person skilled in the art by routine experiments and does not involve any surprising steps.

In certain embodiments the at least one FXII inhibitor is administered at a concentration that produces a reduction in at least one symptom of the neurotraumatic disorder.

The administered pharmaceutical compositions may comprise at least one FXII inhibitor as the sole active compound, or may be delivered in combination with one or more additional compounds, compositions, or biological materials. Examples of additional compounds include steroids, in particular cortisone.

In some embodiments, the effects of treatment with at least one FXII inhibitor on a neurotraumatic disorder can be monitored by measuring the extent of tissue damage and/or edema. Methods for measuring the extent of tissue damage can include, e.g., histology, biochemical, colorimetric and immunological assays (Evans Blue-extravasation, TTC staining, Western Blot, RT-PCR of inflammatory mediators), measurement of neurological function or brain imaging (MRT, CT, PET). In some embodiments, the tissue damage causes loss of neurological function that can be measured using assessment of neurological function (Neuroscore).

In certain embodiments of the disclosed methods, patients should be treated according to the established standards of care for their clinical presentation.

II. Factor XII Inhibitors

As discussed above the terms "Factor XII" and "FXII" each refer to either or both of Factor XII (e.g., the zymogen or precursor form of the peptide) and activated Factor XII (FXIIa). Thus, "FXII inhibitors" can include inhibitors of either or both of FXII and FXIIa (also termed αFXIIa) as well as the activation of FXII, including the FXIIa cleavage products FXIIa alpha and FXIIa beta (also termed FXIIf). Further, anti-FXII antibodies include antibodies that bind to and inhibit either or both of FXII and FXIIa. The term "FXII inhibitor" is also meant to include an inhibitor of FXII that is linked to a half-life extending polypeptide, which in some embodiments includes a linker. Examples of FXII inhibitors that can be used include rHA-Infestin-4, SPINK-1, anti-FXII antibodies, including modified versions/fragments of these proteins that retain the ability to inhibit the activation of FXII. In an embodiment, the FXII inhibitor is SPINK-1 or a modified SPINK-1. In an embodiment, the FXII inhibitor is Infestin-4 or a modified Infestin-4 or an anti-FXII antibody.

The FXII inhibitor is a direct inhibitor of FXII. The term "direct" inhibitor means an inhibitor that acts via contact (e.g., binding) with FXII (or FXIIa), i.e., the FXII inhibitor binds to FXII and/or FXIIa and inhibits its activity and/or activation. In contrast, an indirect inhibitor may act without contacting FXII (or FXIIa) protein. For example, antisense RNA can be used to decrease expression of the FXII gene, or a small molecule can inhibit the effects of FXIIa via interactions with downstream FXIIa reaction partners like Factor XI; these do not interact directly with the FXII protein. Thus, an indirect inhibitor, in contrast to a direct inhibitor, acts upstream or downstream from the FXII protein. Some examples of direct inhibitors are presented below. In some embodiments, the FXII inhibitors are non-endogenous inhibitors; that is, they are not inhibitors that occur naturally (endogenously) in the respective human or animal body. In some embodiments the FXII inhibitor is not a FXII inhibitor like e.g. C1 inhibitor.

In one embodiment the FXII inhibitor is a specific FXII inhibitor, preferably a specific FXIIa inhibitor.

A specific FXII inhibitor refers to an inhibitor which inhibits plasmatic serine proteases or other endogenous proteins other than FXII and/or FXIIa less than or equal to 25% if used in a molar ratio of 1:1. In other words: a specific FXII/FXIIa inhibitor inhibits plasmatic serine proteases other than FXII and/or FXIIa less than or equal to 25% when said inhibitor is used in a molar ratio of 1:1 of the respective plasmatic serine protease to said inhibitor.

Preferably the FXII inhibitor inhibits plasmatic serine proteases other than FXII and/or FXIIa less than or equal to 20%, preferably less than or equal to 15%, preferably less than or equal to 10%, preferably less than or equal to 5%, preferably less than or equal to 1% if used in a molar ratio of 1:1. For example, a specific FXII mAb inhibits the plasmatic serine protease FXIa by only 5%, wherein the molar ratio of FXIa to said mAb is 1:1 whereas the same FXII mAb inhibits FXIIa by at least 80%, preferably at least 90%.

In one embodiment of the invention one other plasmatic serine protease is inhibited by more than 50% if used in a molar ratio of 1:1 of the respective plasmatic serine protease to said inhibitor.

In another embodiment of the invention two other plasmatic serine proteases are inhibited by more than 50% if used in a molar ratio of 1:1 of the respective plasmatic serine protease to said inhibitor.

In yet another embodiment the FXII inhibitor is a human FXII inhibitor, including a humanized monoclonal antibody, preferably a fully human monoclonal antibody.

"Homology" as used herein refers to the percentage number of amino acids that are identical or constitute conservative substitutions. Homology may be determined using sequence comparison programs such as GAP (Deveraux et al., 1984, Nucleic Acids Research 12, 387-395), which is incorporated herein by reference. In this way sequences of a similar or substantially different length to those cited herein could be compared by insertion of gaps into the alignment, such gaps being determined, for example, by the comparison algorithm used by GAP.

In one embodiment the pharmaceutical formulation administered comprises the FXII inhibitor as the only active substance, i.e. the FXII inhibitor is not used in combination with another active agent. Preferably the FXII inhibitor is not used in combination with a phophatidylserine binding agent, e.g. a modified annexin V composition.

A. Infestin-4

In one embodiment, the application provides a FXII inhibitor comprising infestin domain 4 (referred to as "Infestin-4"). Infestins are a class of serine protease inhibitors derived from the midgut of the hematophagous insect, *Triatoma infestans*, a major vector for the parasite *Trypanosoma cruzi*, known to cause Chagas disease (Campos I T N et al. 32 *Insect Biochem. Mol. Bio.* 991-997, 2002; Campos I T N et al. 577 *FEBS Lett.* 512-516, 2004; WO 2008/098720). This insect uses these inhibitors to prevent coagulation of ingested blood. The infestin gene encodes 4 domains that result in proteins that can inhibit different factors in the coagulation pathway. In particular, domain 4 encodes a protein (Infestin-4) that is a strong inhibitor of FXIIa. Infestin-4 has been administered in mice without resulting in bleeding complications (WO 2008/098720; Hagedorn et al., *Circulation* 2010; 121:1510-1 [7]).

In various embodiments, a FXII inhibitor comprises Infestin-4. The term "Infestin-4," as used herein, encompasses variants or fragments of the wild-type peptide that retain the ability to inhibit FXII. In some embodiments, the Infestin-4 is chosen for its ability to inhibit FXIIa. In certain embodiments, the Infestin-4 comprises a variant of Infestin-4, wherein the variant comprises Infestin domain 4, and optionally, Infestin domains 1, 2, and/or 3. In one embodiment, the Infestin-4 is a (His)$_6$-tagged Infestin-4 construct. In another embodiment, the Infestin-4 is a fusion protein comprising a fusion partner, such as a half-life enhancing polypeptide (e.g., albumin, an Fc domain of an IgG, or PEG), bound to infestin-4. In some embodiments, a linker connects the fusion partner to Infestin-4. In various embodiments, the Infestin-4 is the rHA-Infestin-4 protein described in Hagedorn et al. (*Circulation* 2010; 117:1153-60). In one embodiment, a composition comprises albumin bound to the rHA-Infestin-4 protein described in Hagedorn et al. (*Circulation* 2010; 117:1153-60) by a flexible linker. In certain embodiments, other Infestin-4 inhibitors of FXII are used, examples of which are described in WO 2008/098720 and Hagedorn et al. (*Circulation* 2010; 117:1153-60) both of which are incorporated by reference in their entirety.

An example of a wild type Infestin-4 sequence is presented in SEQ ID NO: 1: EVRNPCACFRNYVPV-CGSDGKTYGNPCMLNCAAQTKVPGLKLVHEGRC.

As used here, the term "variant" of Infestin-4 refers to a polypeptide with one or more amino acid mutation, wherein "mutation" is defined as a substitution, a deletion, or an addition, to the wild type Infestin-4 sequence (SEQ ID NO: 1). The term "Infestin-4" encompasses these Infestin-4 variants. The term "variant" of Infestin-4 also includes fragments of the wild type or a mutated Infestin-4 sequence. In various embodiments, the one or more mutations to the wild type Infestin-4 sequence do not substantially alter the functional ability of the polypeptide to inhibit FXII. In some embodiments, the one or more mutations do not completely or substantially remove the ability of the polypeptide to inhibit FXII (e.g., the variant retains at least about 20%, 30%, 40%, 50%, 60%, 70%, 80%, 90%, 95%, 98%, 99%, or more of the inhibitory ability of wild type Infestin-4). Further examples of such variants are provided below.

In one embodiment, an Infestin-4 variant comprises the amino acid sequence VRNPCACFRNYV (SEQ ID NO: 20, which are residues 2-13 of SEQ ID NO: 1) from the amino terminal of the wild type Infestin-4 sequence. In certain embodiments, the variant can comprise residues 2-13 of SEQ ID NO: 1 and also comprises at least one, and optionally up to five, amino acid mutations, as compared to the wild type Infestin-4 sequence, outside residues 2-13 of SEQ ID NO: 1. In some embodiments, the variant retains six conserved cysteine residues from the wild type Infestin-4 sequence, and/or a homology of at least 70%, at least 75%, at least 80%, at least 85%, at least 90%, at least 95%, at least 98%, or at least 99%, to the wild type Infestin-4 sequence. In some embodiments, a variant of Infestin-4 comprises the conserved N-terminal region amino acids 2-13 of the wild type Infestin-4 sequence, and at least one, and optionally up to five, amino acid mutations outside these conserved N-terminal amino acids, resulting in differences from the wild type Infestin-4 sequence. As used here, the term "outside the N-terminal amino acids" of an Infestin variant refers to any amino acid along the polypeptide chain of the variant other than the contiguous stretch of amino acids that comprises the sequence of SEQ ID NO: 20: VRNPCACFRNYV, which are amino acids 2-13 from SEQ ID NO: 1.

In another embodiment, an Infestin-4 variant comprises six conserved cysteine residues and/or has a homology of at least 70%, at least 75%, at least 80%, at least 85%, at least 90%, at least 95%, at least 98%, or at least 99%, to the wild type Infestin-4 sequence. In one embodiment, the six conserved cysteine residues are amino acids at positions 6, 8, 16, 27, 31, and 48 of the wild type Infestin-4 sequence, SEQ ID NO: 1. In one embodiment, the variant comprises the final conserved cysteine at position 48. In other embodiments, the exact positions of the cysteine residues, and relative positions to each other, may change from positions 6, 8, 16, 27, 31, and 48 of the wild type Infestin-4 sequence due to insertions or deletions in the Infestin-4 variant. Nevertheless, in these embodiments, an Infestin-4 variant comprises all six cysteines and/or may share 70%, 75%, 85%, 90%, 91%, 92%, 93%, 94%, 95%, 96%, 97%, 98% or 99%, or any percentage in between homology to the wild type Infestin-4 sequence. In some embodiments, the Infestin-4 variant retains amino acids 2-13 from SEQ ID NO: 1 as well as all six cysteine residues, and may share 70%, 75%, 85%, 90%, 91%, 92%, 93%, 94%, 95%, 96%, 97%, 98% or 99%, or any percentage in between homology to the wild type Infestin-4 sequence.

In some embodiments, the Infestin-4 variant comprises SEQ ID NO: 21: DSLGREVRNPCA. In some embodiments, this sequence is added at or near the N-terminus of a fragment or full length wild type Infestin-4 sequence and derives from the human protein SPINK-1.

In some embodiments, an Infestin-4 variant comprises a fusion construct between wild-type Infestin-4 or a variant Infestin-4 and human albumin (referred to as "HA"). In some embodiments, the HA is a recombinant protein (referred to as "rHA"). In certain embodiments, the Infestin-4 and HA proteins are joined directly, or via a linker polypeptide.

In one embodiment, the FXII inhibitor comprises a variant of the wild type Infestin-4 polypeptide sequence, wherein the variant comprises the N-terminal amino acids 2-13 of SEQ ID NO: 1; at least one, and optionally up to five, amino acid mutations outside the N-terminal amino acids; six conserved cysteine residues; and/or homology of at least 70%, at least 75%, at least 80%, at least 85%, at least 90%, at least 95%, at least 98%, or at least 99%, to the wild type Infestin-4 sequence.

In various embodiments, a variant of Infestin-4 is provided that retains the ability to inhibit FXII. The functional inhibitory activity may be assessed, for example, through in vitro and/or in vivo characterization, including direct assays to test inhibition of FXII enzyme activity, prolonged coagulation time (e.g., activated partial thromboplastin time, aPTT), clinical clotting tests that address the intrinsic pathway of coagulation, or in vivo methods that evaluate coagulation.

Further examples of Infestin-4 variants are SPINK-1 mutants, which are described below.

B. SPINK-1 Mutants

In various embodiments, the at least one FXII inhibitor can comprise a human protein with high similarity to Infestin-4. One example of a human protein with high similarity to Infestin-4 is SPINK-1, a Kazal-type serine protease inhibitor expressed in the pancreas (also known as pancreatic secretory trypsin inhibitor, PSTI). The Kazal-type serine protease inhibitor family is one of numerous families of known serine protease inhibitors. Many similar proteins from different species have been described (Laskowski M and Kato I, 49 *Ann. Rev. Biochem.* 593-626, 1980).

An example of a wild type SPINK-1 sequence is presented in SEQ ID NO: 2 DSLGREAKCYNELNGCTKIYDPVCGTDGNTYPNECVLCFENRKRQTSILIQKSGPC.

In various embodiments a wild-type SPINK-1 sequence (e.g., SEQ ID NO: 2) is used as the FXII inhibitor. The term "SPINK-1" also encompasses functional variants and fragments of SPINK-1 that substantially retain the ability to inhibit FXII, and in some embodiments, these SPINK-1 variants are used as the FXII inhibitors. For example, different variants of the wild-type sequence may be generated in order to increase the homology of the SPINK-1 sequence to Infestin-4. In one embodiment, SPINK-1 is mutated to comprise N-terminal amino acids 2-13 of SEQ ID NO: 1.

In one embodiment, a variant SPINK-1 comprises an N-terminal portion of a wild type Infestin-4 sequence (e.g., amino acids 2-13 of SEQ ID NO: 1), and optionally, at least one, two, three, four, or five additional amino acid mutations outside the N-terminal amino acids that increase the homology of the variant to the wild type Infestin-4 sequence. In another embodiment, a variant SPINK-1 comprises six conserved cysteine residues and has a homology of at least 70%, at least 75%, at least 80%, at least 85%, at least 90%, at least 95%, at least 98%, or at least 99%, to the wild type SPINK-1 sequence and, optionally, has been mutated to increase the homology of the variant to the wild type Infestin-4 sequence.

In some embodiments, the SPINK-1 variant also comprises an N-terminal portion of a wild type Infestin-4 sequence (e.g., amino acids 2-13 of SEQ ID NO: 1). A mutation may comprise a substitution, a deletion, and/or an addition. A mutation that is "outside the N-terminal amino acids" refers to one or more mutations in any amino acids along the polypeptide chain of the variant other than the contiguous stretch of amino acids that comprises the sequence VRNPCACFRNYV (SEQ ID NO: 20), i.e., amino acids 2-13 of SEQ ID NO: 1. The term "variant" includes fragments of a SPINK-1 or mutated SPINK-1 sequence.

In some embodiments, the six conserved cysteine residues of SPINK-1 may be the amino acids at positions 9, 16, 24, 35, 38, and 56 of the wild type SPINK-1 sequence (e.g., SEQ ID NO: 2). In one embodiment, the variant comprises the final cysteine of the wild type SPINK-1 sequence (i.e., the cysteine at position 56 of SEQ ID NO: 2). In some embodiments, the six cysteines are not mutated but the exact positions of the cysteines, and relative positions to each other, may change from positions 9, 16, 24, 35, 38, and 56 of the wild type SPINK-1 sequence due to insertions and/or deletions elsewhere in the SPINK-1 variant. Nevertheless, in these embodiments, a SPINK-1 variant comprises all six cysteines.

In some embodiments, the six cysteines of SPINK-1 are not mutated, but SPINK-1 is mutated to comprise an N-terminal portion of a wild type Infestin-4 sequence (e.g., amino acids 2-13 of SEQ ID NO: 1), and/or to have a homology of at least 70%, at least 75%, at least 80%, at least 85%, at least 90%, at least 95%, at least 98%, or at least 99%, to the wild type SPINK-1 sequence, and/or to include one, two, three, four, or five mutations in the SPINK-1 sequence outside the N-terminal amino acids. For example, a SPINK-1 variant may comprises the N-terminal amino acids 2-13 of SEQ ID NO: 1; at least one, and up to five, amino acid mutations outside the N-terminal amino acids that increase the homology of the variant to the wild type Infestin-4 sequence; six conserved cysteine residues from a wild-type SPINK-1 sequence; and/or a homology of at least 70%, at least 75%, at least 80%, at least 85%, at least 90%, at least 95%, at least 98%, or at least 99%, to the wild type SPINK-1 sequence.

In some embodiments, variants of SPINK-1 substantially retain their ability to inhibit FXII (e.g., the variants retain at least about 20%, 30%, 40%, 50%, 60%, 70%, 80%, 90%, 95%, 98%, 99%, or more of the inhibitory activity of wild type SPINK-1).

Examples of SPINK-1 variants that can be used in the methods disclosed herein include:

K1: DSLGREVRNPCACFRNYVPVCGTDGNTYPNECVLCFENRKRQTSILIQKSGPC;
K2: DSLGREVRNPCACFRNYVPVCGTDGNTYGNECMLCAENRKRQTSILIQKEGPC; and
K3: DSLGREVRNPCACFRNYVPVCGTDGNTYGNECMLNCAENRKRQTSILIQKEGPC
(SEQ ID NOS: 3, 4, and 5, respectively).

In some embodiments, further amino acid substitutions can be made outside of the N-terminus relative to K1 in order to increase homology to Infestin-4. In the case of the SPINK-1 variant K3, five amino acid substitutions increase homology to Infestin-4. In certain embodiments, a SPINK-1 variant may share 70%, 75%, 80%, 85%, 90%, 91%, 92%, 93%, 94%, 95%, 96%, 97%, 98% or 99% (or any percentage in between) homology with the wild type SPINK-1 sequence.

C. FXII Antibodies

In various embodiments, the FXII inhibitor is an anti-FXII antibody that binds to FXII and/or to FXIIa and inhibits or reduces FXII activation and/or activity. The term "anti-factor XII antibody" encompasses full length antibodies and functional fragments thereof (e.g., antigen binding fragments such as Fab, F(ab)$_2$, Fv, and scFv). The term also encompasses polyclonal and monoclonal antibodies and antibodies of any of the isotypes such as IgM, IgD, IgA, IgG, and IgE, and any subclass thereof, such as IgG$_1$, The antibody may be from a mammalian species such as human, mouse, rat, rabbit, goat, hamster, or monkey. In some embodiments, the antibody may be humanized or CDR-grafted. In some embodiments, the antibody may be mutated or modified to alter immunogenicity, half-life, and/or to impart other advantageous properties associated with a therapeutic antibody. In one embodiment, the antibody is an anti-FXII antibody that binds to an epitope on the heavy chain or light chain of FXII, such as a neutralizing epitope.

In some embodiments, the antibody may be conjugated to a polypeptide, nucleic acid, or small molecule. An "anti-FXII antibody" also includes antibodies that bind to and/or inhibit either or both of the zymogen of FXII and the activated protein (FXIIa), including the FXIIa alpha and FXIIa beta cleavage fragments. In some embodiments, the antibody binds specifically to FXIIa or the alpha or beta chain fragments of FXIIa.

In some embodiments, the anti-FXII antibody can bind to and inhibit FXIIa activation and/or activity. Anti-FXII antibodies have been described, for example, in WO 2006/066878, and in Rayon et al., *Blood* 86: 4134-43 (1995), the disclosures of which are hereby incorporated by reference in their entirety. Other monoclonal antibodies (mAbs) to human Factor XII include the B7C9 mAb described by Pixley et al. (*J Biol Chem* 1987; 262, 10140-45); a mAb described by Small et al. (*Blood* 1985; 65:202-10); the monoclonal antibodies F1 and F3 described by Nuijens et al. (*J. Biol. Chem.* 1989; 264:12941-49); the B6F5, C6B7, and D2E10 monoclonal antibodies against the light chain of FXII described in WO89/11865; a monoclonal antibody that selectively binds FXIIa-β over FXII described in WO90/08835; and the anti-FXII antibody OT-2 described in WO91/17258, the disclosures of which are hereby incorporated by reference in their entirety.

Additional anti-Factor XII monoclonal antibodies are described in WO 2013/014092, which is incorporated herein by reference in its entirety. In some embodiments, the antibodies may have a more than 2 fold higher binding affinity to human Factor XIIa-beta than to inactivated human FXII and may be capable of inhibiting the amidolytic activity of human Factor XIIa.

TABLE 1

| Region | Amino acid sequence |
|---|---|
| VH | EVQLLESGGGLVQPGGSLRLSCAASGFTFSKYIMQWVRQAPGK GLEWVSGIRPSGGTTVYADSVKGRFTISRDNSKNTLYLQMNSLR AEDTAVYYCARALPRSGYLISPHYYYYALDVWGQGTTVTVSS (SEQ ID NO: 6) |
| VL | QSELTQPPSASGTPGQRVTISCSGSSSNIGRNYVYWYQQVPGTA PKLLIYSNNQRPSGVPDRFSGSKSGTSASLVISGLRSEDEADYYC AAWDASLRGVFGGGTKLTVLG (SEQ ID NO: 7) |
| HCDR 1 (Kabat 31-35) | KYIMQ (SEQ ID NO: 8) |
| HCDR 2 (Kabat 50-65) | GIRPSGGTTVYADSVKG (SEQ ID NO: 9) |
| HCDR 3 (Kabat 95-102) | ALPRSGYLISPHYYYYALDV (SEQ ID NO: 11) |
| LCDR 1 (Kabat 24-34) | SGSSSNIGRNYVY (SEQ ID NO: 13) |
| LCDR 2 (Kabat 50-56) | SNNQRPS (SEQ ID NO: 14) |
| LCDR 3 (Kabat 89-97) | AAWDASLRGV (SEQ ID NO: 15) |

In certain embodiments, an anti-FXII antibody comprises the heavy chain variable region (VH) and light chain variable region (VL) sequences presented in Table 1. In some embodiments, an anti-FXII antibody comprises the HCDR1, HCDR2, and HCDR3, and/or comprises the VCDR1, VCDR2, and VCDR3 shown in Table 1. Antibody 3F7 as described in WO 2013/014092 A1 is an example of such an antibody.

In some embodiments, the antibody has one or more of the following features: (a) binds human FXII; (b) comprises a heavy chain variable (VH) region which is more than 85% identical to the sequence of SEQ ID NO: 6, such as more than 90%, 95%, 98%, or 99% identical; (c) comprises a light chain variable (VL) region which is more than 85% identical to the sequence of SEQ ID NO: 7, such as more than 90%, 95%, 98%, or 99% identical; (d) comprises heavy chain CDR1 at least 80% identical to the sequence of SEQ ID NO: 8, such as more than 85%, 90%, 95%, 98%, or 99% identical, and/or heavy chain CDR2 at least 60% identical with SEQ ID NO: 9, such as more than 70%, 80%, 85%, 90%, 95%, 98%, or 99% identical, and/or heavy chain CDR3 at least 80% identical to the sequence of SEQ ID NO: 11, such as more than 85%, 90%, 95%, 98%, or 99% identical; (e) comprises light chain CDR1 at least 50% identical to SEQ ID NO: 13, such as more than 60%, 70%, 80%, 85%, 90%, 95%, 98%, or 99% identical, and/or at least 50% identical to light chain CDR2 of SEQ ID NO: 14, such as more than 60%, 70%, 80%, 85%, 90%, 95%, 98%, or 99% identical, and/or at least 50% identical to light chain CDR3, with the sequence A-$X_1$-W-$X_2$-$X_3$-$X_4$-$X_5$-R-$X_6$-$X_7$ (SEQ ID NO: 16), such as more than 60%, 70%, 80%, 85%, 90%, 95%, 98%, or 99% identical; wherein $X_1$ can be A or S, $X_5$ can be L or V, and the other $X_n$'s can be any amino acid; (f) binds human Factor XIIa-beta with a $K_D$ of better than $10^{-8}$M; (g) competes with Infestin-4 for binding to human Factor XIIa-beta; or (h) is a human IgG or functional variant thereof, preferably human IgG4 or a functional variant thereof.

In certain embodiments, the anti-FXII antibody is an IgG antibody that binds human FXII/FXIIa and comprises (a) a VH region comprising heavy chain CDR1 as set forth in SEQ ID NO: 8, heavy chain CDR2 as set forth in SEQ ID NO: 10, and heavy chain CDR3 as set forth in SEQ ID NO: 12; and/or (b) a VL region comprising light chain CDR1 as set forth in SEQ ID NO: 13, light chain CDR2 as set forth in SEQ ID NO: 14, and light chain CDR3 as set forth in SEQ ID NO: 16. A heavy chain CDR2 can comprise the sequence G1$X_1$$X_2$$X_3$$X_4$$X_5$$X_6$TVYADSVKG (SEQ ID NO: 10), wherein $X_1$ is R, N or D, $X_2$ is P, V, I, or M; $X_3$ is S, P, or A; $X_4$ is G, L, V, or T; $X_5$ can be any amino acid, preferably $X_5$ is G, Y, Q, K, R, N, or M; and $X_6$ is T, G, or S. A heavy chain CDR3 can comprise the sequence ALPRSGYL$X_1$$X_2$$X_3$$X_4$YYYYALDV (SEQ ID NO: 12), wherein $X_1$ is I, M or V; $X_2$ is S or K; $X_3$ is P, K, T, or H; and $X_4$ is H, N, G, or Q. A light chain CDR3 can comprise the sequence A$X_1$W$X_2$$X_3$$X_4$$X_5$R$X_6$$X_7$ (SEQ ID NO: 16), wherein $X_1$ is A or S; $X_2$ is D, Y, E, T, W, E, or S; $X_3$ is A, N, I, L, V, P, Q, or E; $X_4$ is S, D, P, E, Q, or R; $X_5$ is L or V; $X_6$ is G, L, or K; and $X_7$ is V, A, D, T, M, or G.

In other embodiments, the anti-FXII antibody is a fragment of an IgG antibody that binds human FXII/FXIIa and comprises (a) a VH region comprising heavy chain CDR1 as set forth in SEQ ID NO: 8, heavy chain CDR2 as set forth in SEQ ID NO: 9, and heavy chain CDR3 as set forth in SEQ ID NO: 11; and/or (b) a VL region comprising light chain CDR1 as set forth in SEQ ID NO: 13, light chain CDR2 as set forth in SEQ ID NO: 14, and light chain CDR3 as set forth in SEQ ID NO: 15.

In various embodiments, the anti-FXII antibody is an affinity matured, chimeric, CDR grafted, or humanized antibody, or a functional antigen binding fragment thereof. In some embodiments, the anti-FXII antibody is chosen from the affinity matured (relative to 3F7) antibodies VR115, VR112, VR24, VR110, and VR119 (SEQ ID NOs for HCDR 1-3 and LCDR1-3 of these antibodies are shown below in Table 2).

TABLE 2

| mAb | HCDR1 | HCDR2 | HCDR3 | LCDR1 | LCDR2 | LCDR3 |
|---|---|---|---|---|---|---|
| 3F7 | 8 | 9 | 11 | 13 | 14 | 15 |
| VR119 | 8 | 10 | 11 | 13 | 14 | 15 |
| VR112 | 8 | 10 | 11 | 13 | 14 | 15 |
| VR115 | 8 | 10 | 11 | 13 | 14 | 15 |
| VR24 | 8 | 9 | 11 | 17 | 14 | 15 |
| VR110 | 8 | 10 | 11 | 13 | 14 | 15 |

As noted above, SEQ ID NO: 10 is a degenerate sequence. VR119 comprises SEQ ID NO: 10 wherein $X_1$ is N, $X_2$ is V, $X_3$ is P; $X_4$ is L, $X_5$ Y; and $X_6$ is G. VR112 comprises SEQ ID NO: 10 wherein $X_1$ is N, $X_2$ is V, $X_3$ is P, $X_4$ is V, $X_5$ is Q, and $X_6$ is G. VR115 comprises SEQ ID NO: 10 wherein $X_1$ is D, $X_2$ is I, $X_3$ is P, $X_4$ is T, $X_5$ is K, and $X_6$ is G. VR110 comprises SEQ ID NO: 10 wherein $X_1$ is D, $X_2$ is M, $X_3$ is P, $X_4$ is T, $X_5$ is K, and $X_6$ is G. VR24 comprises a unique LCDR1: SGSSEMTVHHYVY (SEQ ID NO: 17).

In embodiments involving antibody CDRs, CDR's are defined according to the KABAT numbering system (Kabat et al., Sequences of proteins of immunological interest, 5th ed. U.S. Department of Health and Human services, NIH, Bethesda, MD (1991)).

In some embodiments, the antibody is an anti-FXII monoclonal antibody or antigen-binding fragment thereof that inhibits human FXIIa-alpha, e.g., in an in vitro FXIIa amidolytic activity assay (WO 2013/014092), by more than 40%, more than 50%, or more than 60%, when used at a molar ratio of 1:0.2 of FXIIa-alpha to antibody. In some embodiments, the antibody or antigen binding fragment thereof inhibits human Factor XIIa-alpha by more than 80%, more than 85%, or more than 90%, when used at a molar ratio of 1:0.5 of FXIIa-alpha to antibody. In one embodiment, the antibody achieves complete or nearly complete (e.g., 95%, 96%, 97%, 98%, 99%, or greater) inhibition of human FXIIa-alpha when used at a molar ratio of 1:0.5. In one embodiment, the antibody or antigen binding fragment thereof has an affinity for human FXIIa that is at least approximately comparable to that of antibody 3F7.

D. FXII Inhibitors Linked to HLEPs

Another aspect of the application provides FXII inhibitors linked to fusion partners, such as half-life enhancing polypeptides (HLEPs) or molecules such as PEG. In one embodiment, FXII inhibitors are small proteins. Therefore, rapid renal clearance (as is observed for other small proteins) can be expected (Werle M and Bernkop-Schnurch A, *Amino Acids* 2006; 30:351-367). One way to address a short plasma half-life of a polypeptidic compound is to inject it repeatedly or via continuous infusion. Another approach is to increase the intrinsic plasma half-life of the polypeptide itself. For example, in one embodiment, FXII inhibitors are linked to half-life extending proteins.

A "half-life enhancing polypeptide" is a polypeptide fusion partner that may increase the half-life of the FXII inhibitor in vivo in a patient or in an animal. Examples include albumin and immunoglobulins and their fragments, such as Fc domains, or derivatives, which may be fused to a FXII inhibitor directly or via a cleavable or non-cleavable linker. Ballance et al. (WO 2001/79271) described fusion polypeptides comprising a multitude of different therapeutic polypeptides fused to human serum albumin.

The terms "albumin" and "serum albumin" encompass human albumin (HA) and variants thereof, the full mature form of which is disclosed herein (SEQ ID NO: 19), as well as albumin from other species and variants thereof. As used herein, "albumin" refers to an albumin polypeptide or amino acid sequence, or an albumin variant, having one or more functional activities (e.g. biological activities) of albumin. In certain embodiments, albumin is used to stabilize or prolong the therapeutic activity of a FXII inhibitor. The albumin may be derived from any vertebrate, especially any mammal, for example human, monkey, cow, sheep, or pig. Non-mammalian albumin can also be used and includes, but is not limited to, albumin from chicken and salmon. The albumin portion of the albumin-linked polypeptide may be from a different animal than the therapeutic polypeptide portion. See WO 2008/098720 for examples of albumin fusion proteins, incorporated herein by reference in its entirety.

In one embodiment, an albumin variant is at least 10, 20, 40, 50, 60, or at least 70 amino acids long (or any length in between) or may include 15, 20, 25, 30, 50 or more contiguous amino acids (or any number in between) from a human albumin (HA) sequence (e.g., SEQ ID NO: 19), or may include part or all of specific domains of HA. An albumin variant may include an amino acid substitution, deletion, or addition, either conservative or non-conservative substitution, wherein such changes do not substantially alter the active site, or active domain, which confers the therapeutic activities of the half-life enhancing polypeptides. These variants may share homology of 70%, 75%, 80%, 85%, 90%, 91%, 92%, 93%, 94%, 95%, 96%, 97%, 98% or 99% (or any percentage in between).

In some embodiments, the albumin variant is a fragment and may comprise at least one whole domain of albumin and/or fragments of those domains, for example domains 1 (amino acids 1-194 of SEQ ID NO: 19), 2 (amino acids 195-387 of SEQ ID NO: 19), 3 (amino acids 388-585 of SEQ ID NO 19), 1+2 (1-387 of SEQ ID NO: 19), 2+3 (195-585 of SEQ ID NO: 19) or 1+3 (amino acids 1-194+ amino acids 388-585 of SEQ ID NO: 19). Each domain is itself made up of two homologous subdomains namely residues 1-105, 120-194, 195-291, 316-387, 388-491 and 512-585, of SEQ ID NO: 19, with flexible inter-subdomain linker regions comprising residues Lys106 to Glu119, Glu292 to Val315 and Glu492 to Ala511. Thus, in some embodiments, the albumin variant comprises at least one whole subdomain of albumin.

In certain embodiments, other proteins that are structurally or evolutionarily related to albumin ("albumin family proteins") may be used as HLEPs, including, but not limited to alpha-fetoprotein (WO 2005/024044; Beattie and Dugaiczyk, 20 Gene 415-422, 1982), afamin (Lichenstein et al. 269 (27) J. Biol. Chem. 18149-18154, 1994), and vitamin D binding protein (Cooke and David, 76 J. Clin. Invest. 2420-2424, 1985). The genes encoding these proteins represent a multigene cluster with structural and functional similarities mapping to the same chromosomal region in humans, mice, and rats. The structural similarity of the albumin family members suggests that they can be used as HLEPs. For example, alpha-fetoprotein has been claimed to extend the half-life of an attached therapeutic polypeptide in vivo (WO 2005/024044). Thus, in some embodiments, these proteins, or variants thereof, that may be capable of stabilizing or prolonging therapeutic activity, can be used as HLEPs linked to FXII or FXIIa and may be derived from any vertebrate, especially any mammal, for example human, monkey, cow, sheep, or pig, or non-mammal including but not limited to, hen or salmon. In some embodiments, variants may comprise 10 or more amino acids in length, or may comprise about 15, 20, 25, 30, 50 or more contiguous amino acids of the respective protein sequence from which they are derived, or may include part or all of specific domains of the respective proteins. Albumin family member fusion proteins may include naturally occurring polymorphic variants.

In certain embodiments, mono- or poly- (e.g., 2-4) polyethylene glycol (PEG) moieties may be used as fusion partners and may extend in vivo half-lives. Pegylation may be carried out by any of the pegylation reactions available. Exemplary methods for preparing pegylated protein products can generally include (a) reacting a polypeptide with polyethylene glycol (such as a reactive ester or aldehyde derivative of PEG) under conditions whereby the protein becomes attached to one or more PEG groups; and (b) obtaining the reaction product(s). There are a number of PEG attachment methods. See, for example, EP 0 401 384; Malik et al., Exp. Hematol., 20:1028-1035 (1992); Francis, Focus on Growth Factors, 3(2):4-10 (1992); EP 0 154 316; EP 0 401 384; WO 92/16221; WO 95/34326; U.S. Pat. No. 5,252,714, incorporated herein by reference in their entirety.

In some embodiments, an immunoglobulin (Ig) may be used as an HLEP. The term "immunoglobulin" encompasses functional fragments and variants thereof, such as an Fc region or one or more Ig constant domains. In some embodiments, the Ig comprises an Fc region or portions of the immunoglobulin constant domain(s). The constant region may be that of an IgM, IgG, IgD, IgA, or IgE immunoglobulin. In some embodiments, the therapeutic polypeptide portion is connected to the Ig via the hinge region of the antibody or a peptide linker, which may be cleavable. Several patents and patent applications describe the fusion of therapeutic proteins to immunoglobulin constant regions to extend the therapeutic protein's half-life in vivo (US 2004/0087778, WO 2005/001025, WO 2005/063808, WO 2003/076567, WO 2005/000892, WO 2004/101740, U.S. Pat. No. 6,403,077), incorporated herein by reference. Therefore, in some embodiments, immunoglobulin regions (e.g., Fc domains, Fc fragments of immunoglobulins, and variants thereof) are used as HLEPs. In some embodiments, inhibitors of FXII can be fused to Fc domains or portions of immunoglobulin constant regions as HLEPs. In some embodiments, these fusion proteins are prepared as recombinant molecules expressed in prokaryotic or eukaryotic host cells, such as bacteria, yeast, plant, animal (including insect) or human cell lines or in transgenic animals (WO 2008/098720, incorporated herein by reference).

An example of a SPINK mutant-Fc fusion protein, the SPINK-K2-Fc fusion protein, is described in WO 2008/098720.

E. Linkers

In various embodiments, an intervening peptidic linker may be introduced between a therapeutic polypeptide and a HLEP. In one embodiment, a cleavable linker is introduced, particularly if the HLEP has the potential to interfere with the therapeutic polypeptide's specific activity, e.g. by steric hindrance. In certain embodiments, the linker is cleavable by enzymes involved in coagulation, such as coagulation proteases of the intrinsic, extrinsic, or common coagulation pathway. Coagulation proteases of the intrinsic pathway include proteases in the contact activation pathway, e.g., FXIIa, FXIa, or FIXa. In one embodiment, the linker is cleaved by FXIIa. Proteases of the extrinsic pathway include proteases in the tissue factor pathway, for example, FVIIa. Proteases of the common pathway include proteases involved in the conversion of fibrinogen to fibrin, for example, FXa, FIIa, and FXIIIa.

III. Pharmaceutical Compositions

In any of the various aspects of the invention, the FXII inhibitor may have a purity of greater than 80%, or greater than 95%, 96%, 97%, 98%, or 99%. In one embodiment, the FXII inhibitor may have a pharmaceutically pure state that is greater than 99.9% pure with respect to contaminating macromolecules, such as other proteins and nucleic acids, and may be free of infectious and pyrogenic agents.

In certain embodiments, a pharmaceutical composition can comprise at least one additive such as a filler, bulking agent, buffer, stabilizer, or excipient. Some exemplary pharmaceutical formulation techniques are described, e.g., in the 2005 Physicians' Desk Reference, Thomson Healthcare: Montvale, NJ, 2004; Remington: The Science and Practice of Pharmacy, 20th ed., Gennaro et al., Eds. Lippincott Williams & Wilkins: Philadelphia, PA, 2000; Kibbe et al. Handbook of Pharmaceutical Excipients, 3rd ed., Pharmaceutical Press, 2000. Pharmaceutical additives include, e.g., mannitol, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In certain embodiments, the pharmaceutical compositions may also contain pH buffering reagents and wetting or emulsifying agents. In further embodiments, the compositions may contain preservatives and/or stabilizers. Pharmaceutical compositions may be formulated in lyophilized or stable soluble form. Polypeptides may be lyophilized by a variety of procedures known in the art.

In certain embodiments, a pharmaceutical composition comprising at least one FXII inhibitor is prepared for use in treating a neurotraumatic disorder selected from spinal cord injury and traumatic brain injury. For example, if a powder or lyophilized form of FXII inhibitor (e.g., by freeze drying) is provided and an aqueous pharmaceutical is desired, the powder can be dissolved by mixing with aqueous components of the pharmaceutical formulation and stirred using suitable techniques such as vortexing or gentle agitation. Alternatively, if an aqueous pharmaceutical is desired and the FXII inhibitor is already in aqueous form, the components can be directly combined prior to administration. In certain embodiments, FXII inhibitor is provided in lyophilized form and combined with aqueous pharmaceutical components (e.g., additional active components or inactive components such as fillers, stabilizers, solvents or carriers) prior to administration.

The formulation of pharmaceutical compositions may vary depending on the intended route of administrations and other parameters (see, e.g., Rowe et al., Handbook of Pharmaceutical Excipients, 4th ed., APhA Publications, 2003). In some embodiments, the pharmaceutical composition may be a lyophilized cake or powder. The lyophilized composition may be reconstituted for administration by intravenous injection, for example with Sterile Water for Injection, USP. In other embodiments, the composition may be a sterile, non-pyrogenic solution. In still further embodiments, the composition is delivered in powder form, in a pill or tablet.

Formulations of the FXII inhibitor may be delivered to the patient by any pharmaceutically suitable means of administration. For example, the compositions can be administered systemically, such as parenterally, or intrathecally. Parenteral formulations may be administered intravenously or subcutaneously, either in bolus form or as an infusion, according to known procedures. Preferred liquid carriers, which are well known for parenteral use, include sterile water, saline, aqueous dextrose, sugar solutions, ethanol, glycols, and oils. For systemic use, the therapeutic protein(s) may be formulated for an intravenous line or an arterial line. The formulations may be administered continuously by infusion or by bolus injection.

Tablets and capsules for oral or rectal administration may contain conventional excipients such as binding agents, fillers, lubricants, or wetting agents, etc. Oral or rectal liquid preparations may be in the form of aqueous or oily suspensions, solutions, emulsions, syrups, elixirs or the like, or may be presented as a dry product for reconstitution with water or other suitable vehicle prior to use. Such liquid preparations may contain conventional additives, such as suspending agents, emulsifying agents, non-aqueous vehicles, and preservatives. Some formulations encompass slow release systems, such as a patch.

Also disclosed are kits for the treatment of a neurotraumatic disorder selected from spinal cord injury and traumatic brain injury. In certain embodiments, the kits comprise (a) at least one FXII inhibitor; (b) instructions for use in the treatment of a neurotraumatic disorder selected from spinal cord injury and traumatic brain injury, and optionally (c) at least one further therapeutically active ingredient wherein the further therapeutically active ingredient is not C1 inhibitor.

The components of the kit may be contained in one or different containers such as one or more vials. The at least one FXII inhibitor may be in liquid or solid form (e.g. after lyophilization). If in liquid form, the at least one FXII inhibitor may comprise additives such as stabilizers and/or preservatives such as proline, glycine, or sucrose or other additives.

In certain embodiments, the kit may contain additional compounds such as therapeutically active compounds or drugs that are to be administered before, at the same time, or after administration of the at least one FXII inhibitor, wherein the further therapeutically active ingredient is not C1 inhibitor. Examples of such compounds include vitamins, antibiotics, anti-viral agents, etc. In other embodiments, a steroid, in particular cortisone, can be included with the kit.

In various embodiments, instructions for use of the kit can include directions to use the kit components in the treatment of a neurotraumatic disorder selected from spinal cord injury and traumatic brain injury. The instructions may further contain information regarding how to prepare (e.g., dilute or reconstitute, in the case of freeze-dried protein) the at least one FXII inhibitor. The instructions may further include guidance regarding the dosage and/or frequency of administration.

The Figures show:

FIG. 1 shows reduction of lesion size in rHA-Infestin-4 treated or FXII$^{-/-}$ mice compared to NaCl-treated or wild-type (Bl/6) controls, respectively, 24 h after trauma induction. TTC stainings of brain slices gained from male and female mice were analyzed for their lesion volume. FXII deficiency or inhibition reduces lesion sizes 24 h after trauma induction. (A) Lesion volumes in male wild-type and FXII$^{-/-}$ mice (n=19), (B) in female mice (n=4 for Bl/6 and n=5 for FXII$^{-/-}$) and (C) in rHA-Infestin-4 treated animals and controls (n=14 for rHA-Infestin-4 and n=13 for controls). *P<0.001, P<0.01, unpaired, two-tailed Student's t-test, mean+SEM.

Figure 2:
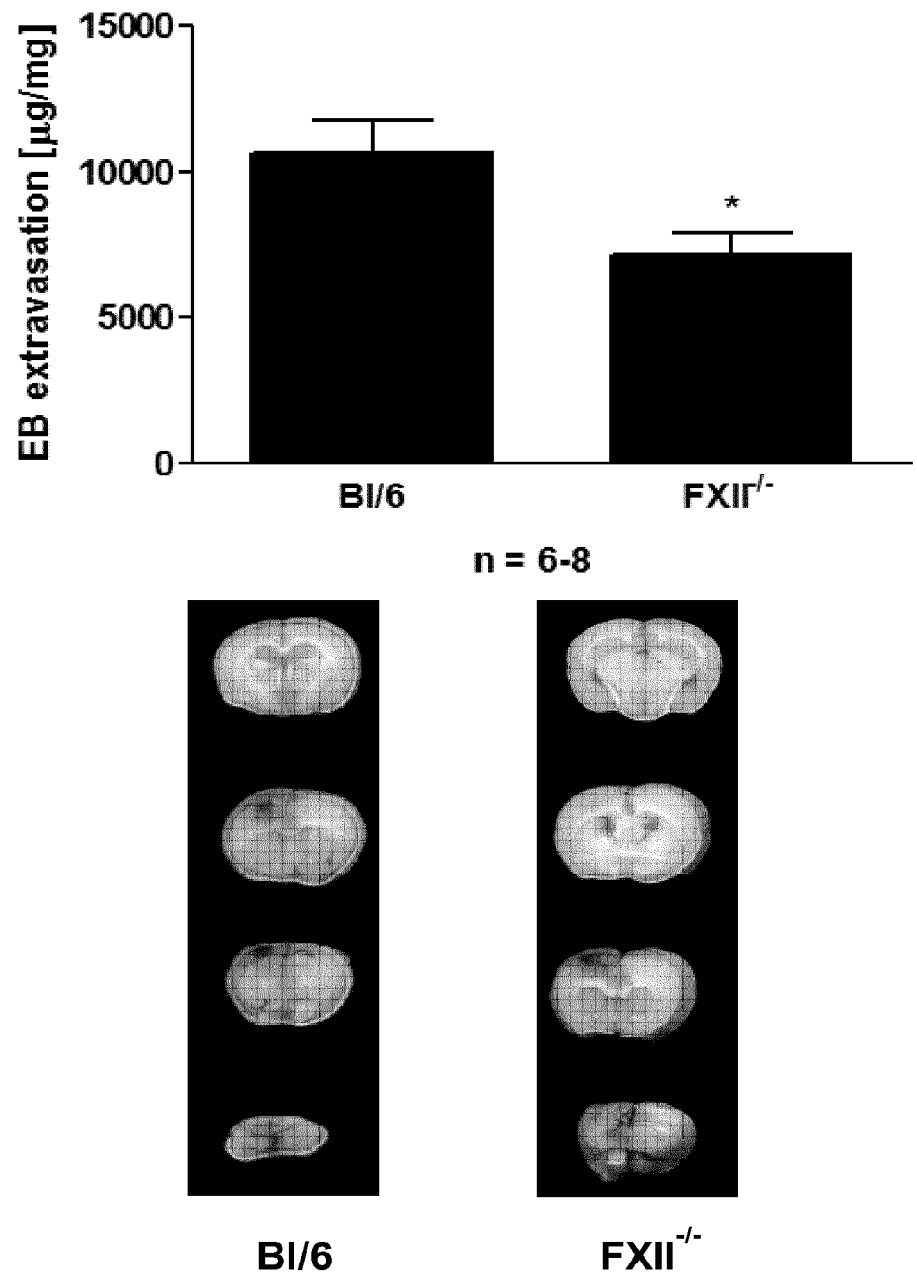
FIG. 2 shows preservation of the blood-brain-barrier (BBB) integrity 24 h after trauma induction in $FXII^{-/-}$ mice compared to WT controls. BBB integrity was analyzed by the extent of Evans Blue extravasation in the lesioned hemisphere determined by photometry and the brain water content as a measure of brain edema in the lesioned hemisphere.
Figure 2:
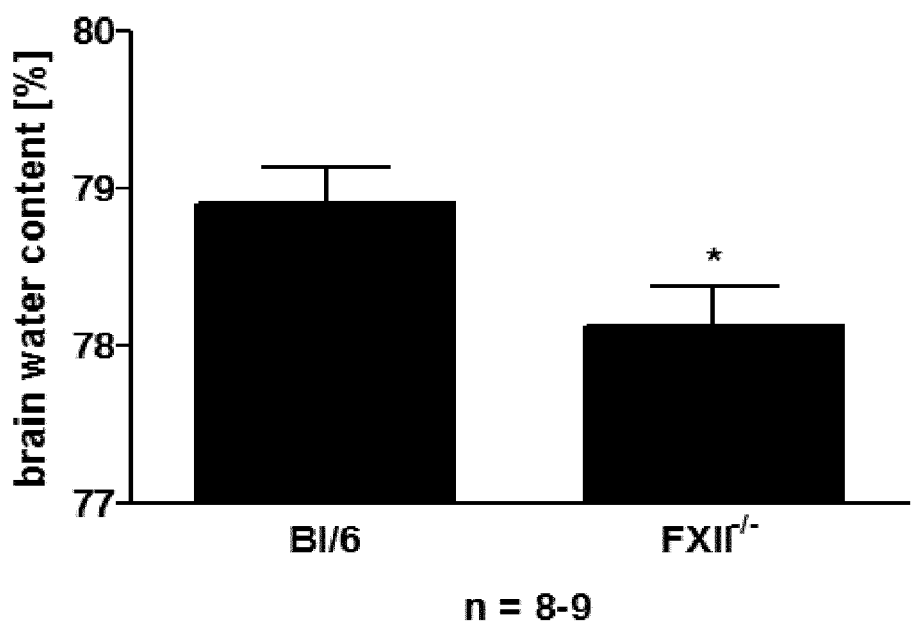

FIG. 2 shows preservation of blood-brain-barrier (BBB) integrity 24 h after trauma induction in FXII$^{-/-}$ mice compared to wild-type controls (Bl/6). (A) Extent of Evans Blue extravasation in the lesioned hemisphere determined by photometry (n=6 for FXII$^{-/-}$ and n=8 for Bl/6). (B) Brain water content as a measure of brain edema in the lesioned hemisphere (n=8 for FXII$^{-/-}$ and n=9 for Bl/6). *P<0.05, unpaired, two-tailed Student's t-test, mean+SEM.

Figure 3:
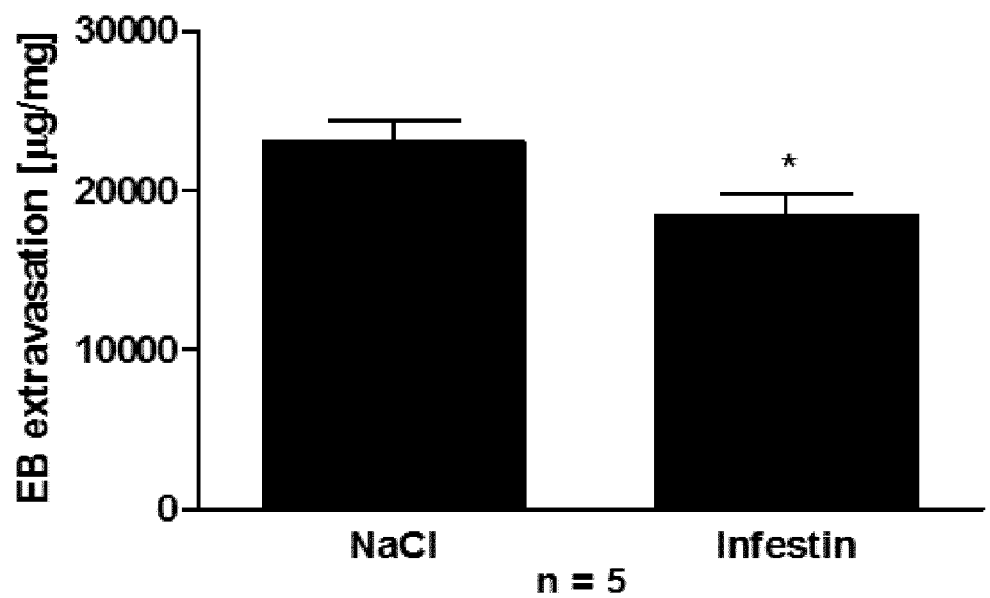
FIG. 3 shows the preservation of the blood-brain-barrier (BBB) integrity 24 h after trauma induction in rHA-Infestin-4 treated mice compared to NaCl-treated controls. BBB integrity was analyzed by the extent of Evans Blue extravasation in the lesioned hemisphere determined by photometry and the relative protein expression of the BBB structural protein Occludin. The brain water content is a measure of brain edema in the lesioned hemisphere.
Figure 3:
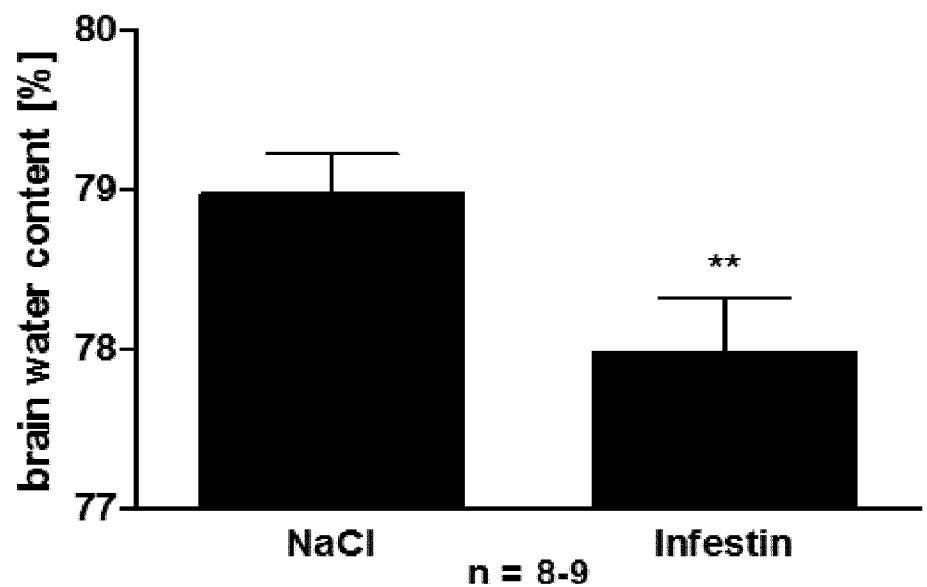
Figure 3:
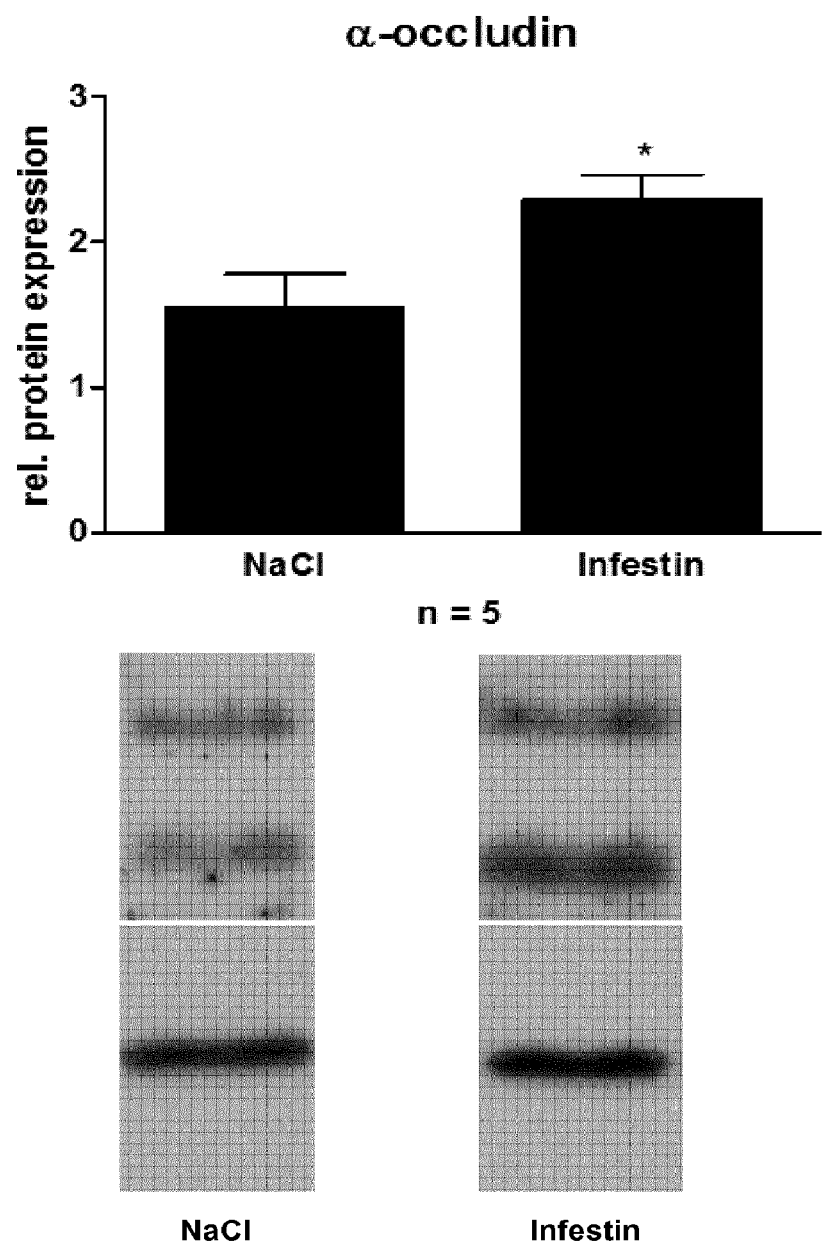

FIG. 3 shows preservation of the blood-brain-barrier (BBB) integrity 24 h after trauma induction in rHA-Infestin-4 treated mice compared to NaCl-treated controls. BBB integrity was analyzed by the (A) extent of Evans Blue (EB) extravasation in the lesioned hemisphere determined by photometry (n=5) and (B) brain water content as a measure of brain edema in the lesioned hemisphere (n=8 for rHA-Infestin-4 and n=9 for controls). (C) Relative protein expression of tight junction protein Occludin (n=5) **P<0.01, *P<0.05, unpaired, two-tailed Student's t-test, mean+SEM.

Figure 4:
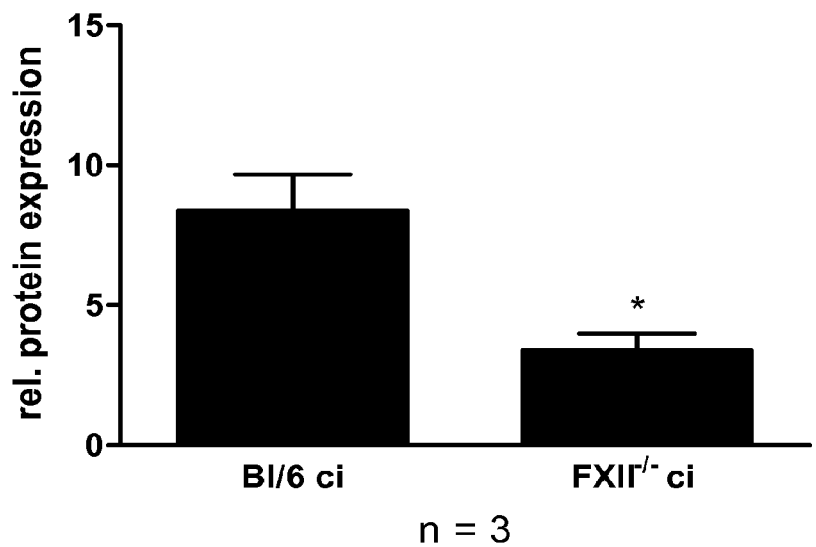
FIG. 4 shows the decrease in thrombus formation and dampened thrombotic processes 24 h after trauma induction. The relative protein expression of Fibrin/Fibrinogen was analyzed via Western blotting and is reduced in $FXII^{-/-}$ mice compared to WT controls. The ratio of occluded vessels to open vessels in the lesioned hemisphere was analyzed histologically via H&E staining of brain tissue and a reduced ratio of occluded to open vessels was found in rHA-Infestin-4 treated mice compared to NaCl-treated controls.
Figure 4:
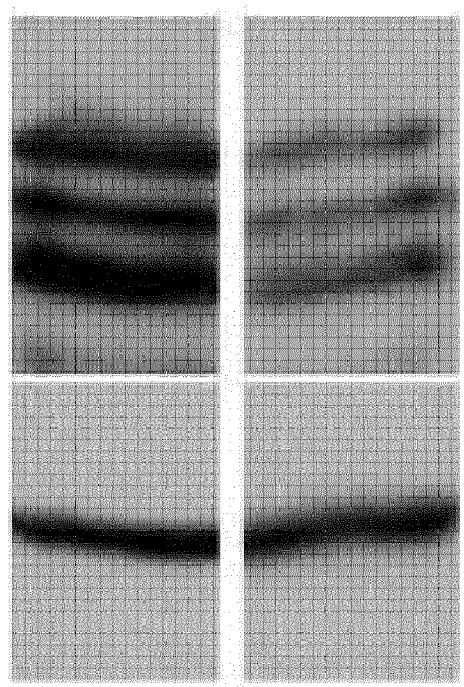
Figure 4:
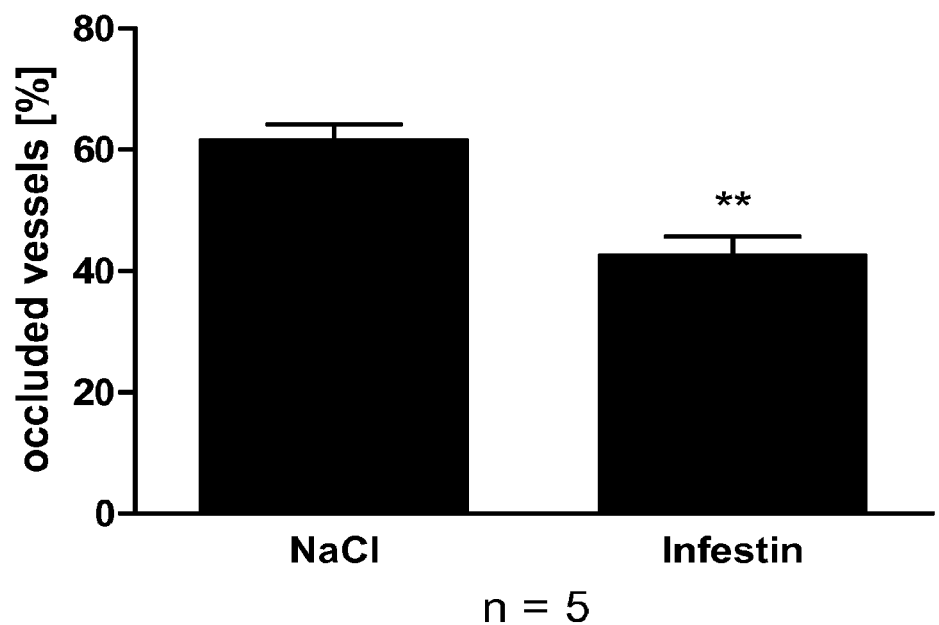
Figure 4:
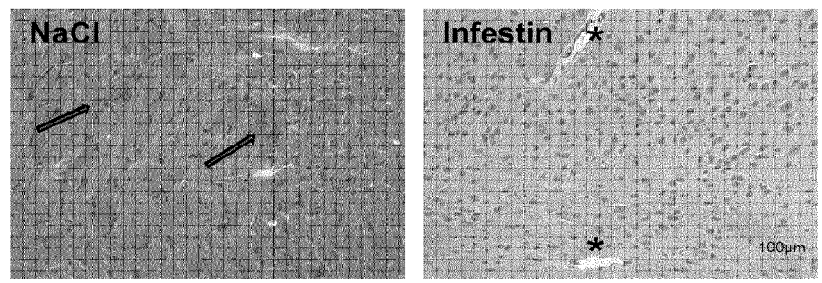

FIG. 4 shows the decrease in thrombus formation and dampened thrombotic processes 24 h after trauma induction. (A) Relative protein expression of Fibrin/Fibrinogen was analyzed via Western blotting and is reduced in FXII$^{-/-}$ mice compared to wild-type controls (Bl/6; n=3). (B) The ratio of occluded vessels to open vessels in the lesioned hemisphere was determined in H&E stained brain slices (n=5, 5 slices per animal). Representative stainings (lower panel) with occluded vessels (arrow) and open vessels (asterisk). An improved ratio was found in rHA-Infestin-4 treated mice compared to NaCl-treated controls. **P<0.01, *P<0.05, unpaired, two-tailed Student's t-test, mean+SEM.

Figure 5:
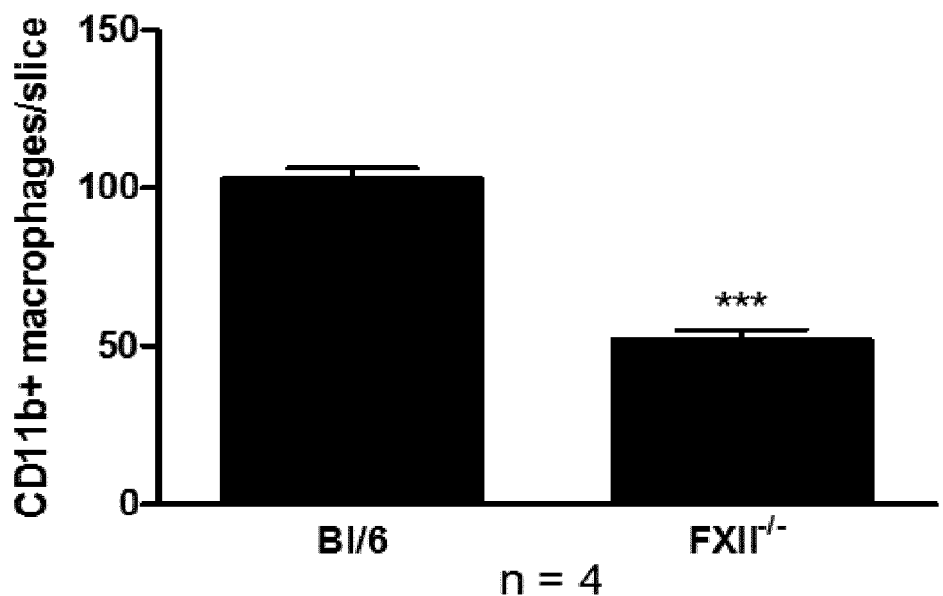
FIG. 5 shows protection from inflammatory processes in $FXII^{-/-}$ mice 24 h after trauma induction. The quantification of macrophage infiltration into lesioned hemisphere was analyzed with immunohistochemical staining; the relative gene expression of proinflammatory cytokines TNFα and Interleukin-1β was measured in $FXII^{-/-}$ mice compared to WT controls and sham-operated mice.
Figure 5:
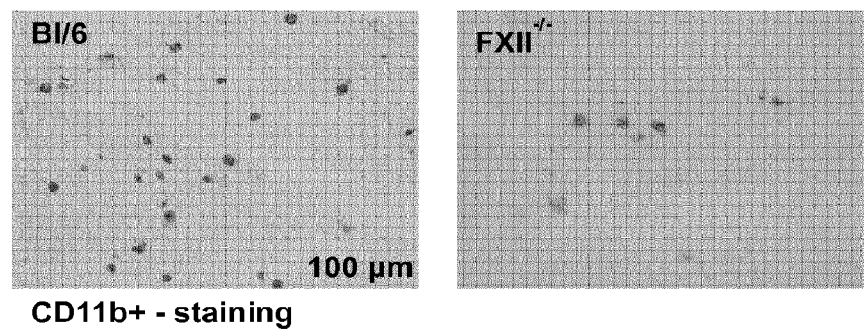
Figure 5:
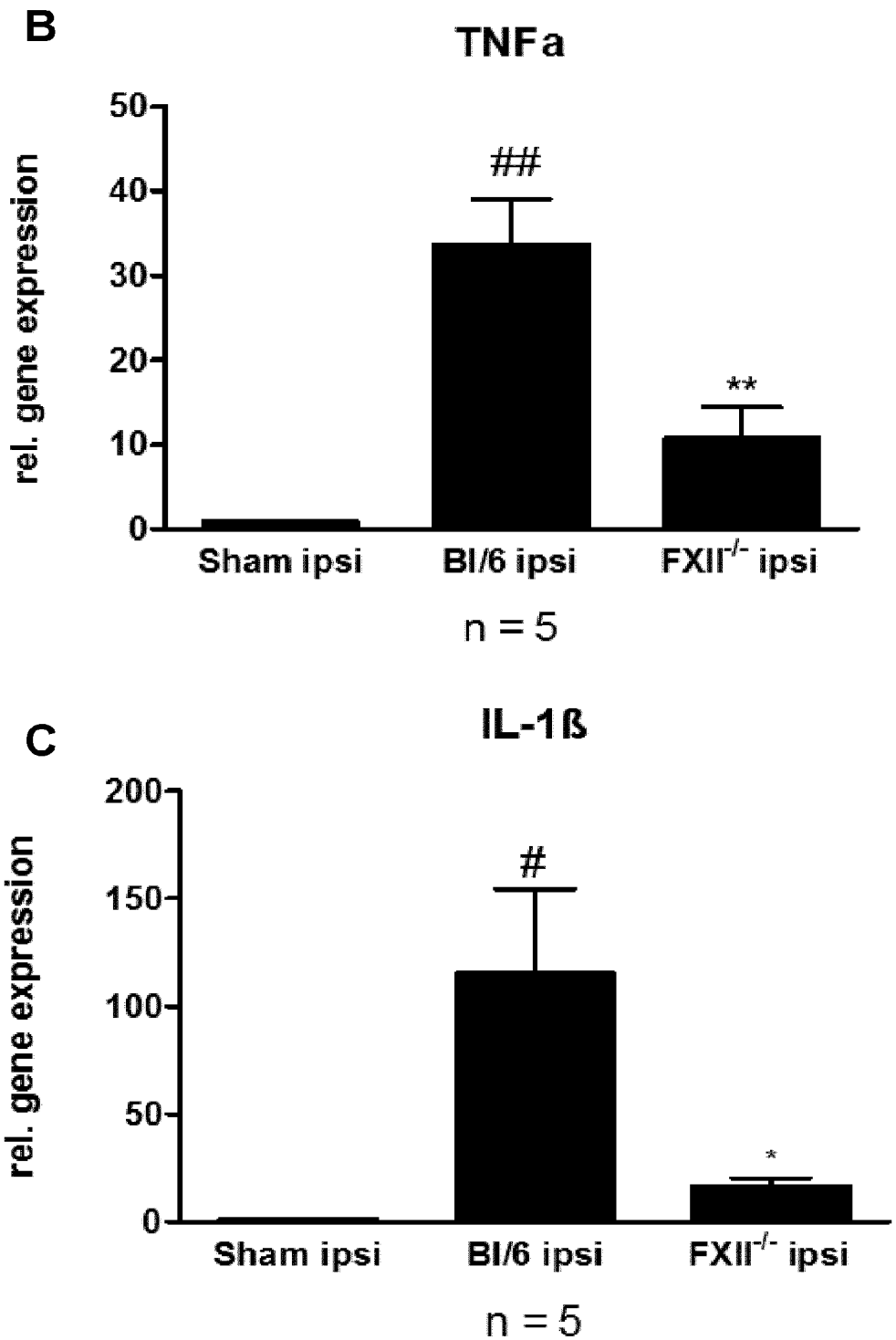

FIG. 5 shows protection from inflammatory processes in FXII$^{-/-}$ mice 24 h after trauma induction. (A) The quantification of macrophage infiltration into lesioned hemisphere was analyzed with immunohistochemical staining against CD11b+ macrophages/microglia at Day 1 and compared to wild-type controls (Bl/6; n=4). Relative gene expression of proinflammatory cytokines TNFα (B) and Interleukin-1β (C) was measured in FXII$^{-/-}$ mice compared to wild-type controls (Bl/6) and sham-operated mice in the ipsilateral cortices (ipsi) after trauma induction (n=5). *P<0.001, P<0.01, *P<0.05, compared with Bl/6, ##P<0.01, #P<0.05 compared with sham operated animals, unpaired, two-tailed Student's t-test (A), 1-way ANOVA followed by Bonferroni post-hoc test, mean+SEM.

Figure 6:
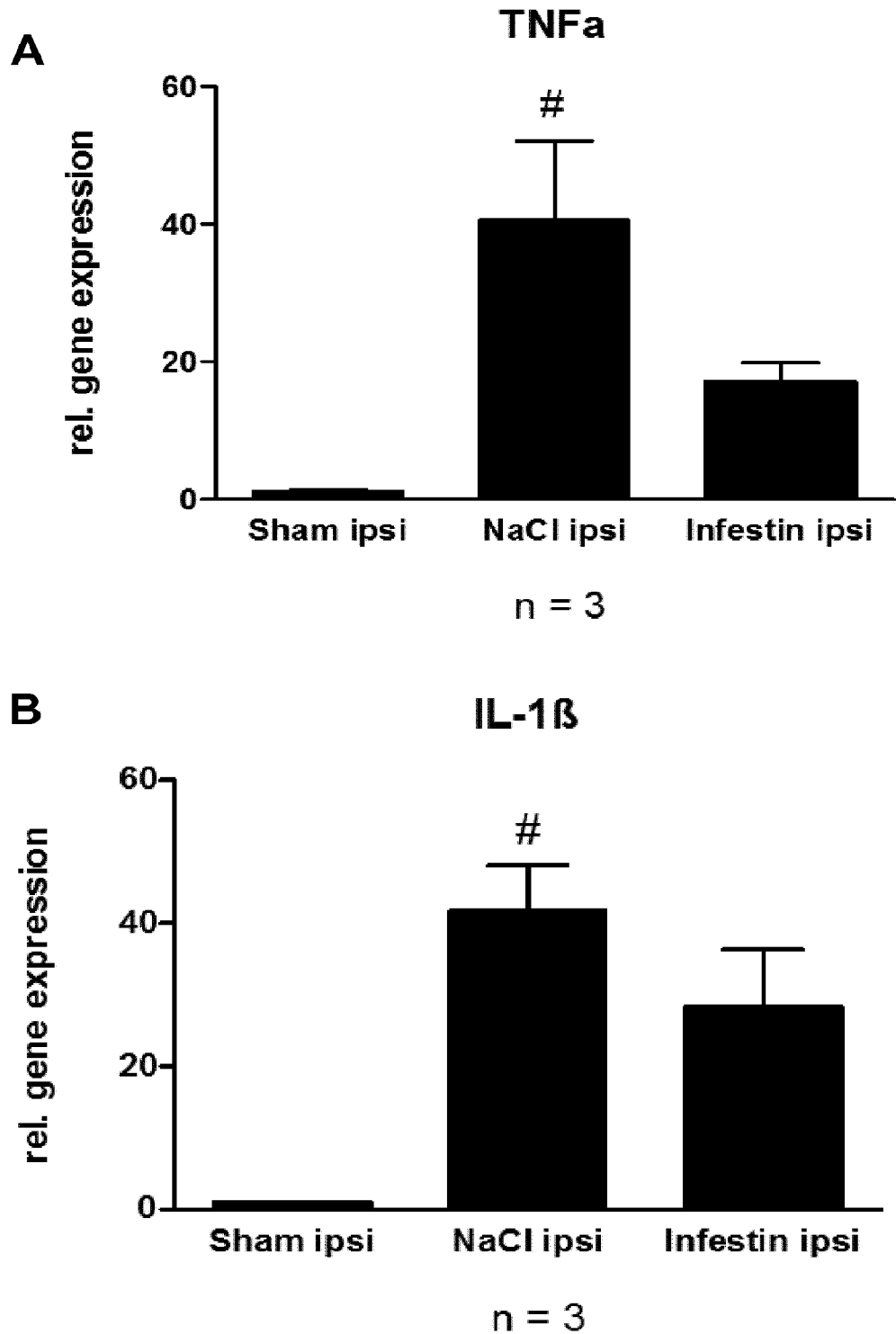
FIG. 6 shows that inflammatory processes are dampened in rHA-Infestin-4 treated animals 24 h after trauma induction. The relative gene expression of proinflammatory cytokines TNFα and Interleukin-1β as measured in rHA-Infestin-4 treated compared to NaCl-treated and sham-operated mice.

FIG. 6 shows proinflammatory cytokines in rHA-Infestin-4 treated compared to NaCl-treated and sham-operated mice. Inflammatory processes are dampened in rHA-Infestin-4 treated animals 24 h after trauma induction. Relative gene expression for proinflammatory cytokines TNFα (A) and Interleukin-1β (B) in the ipsilateral cortices (ipsi; n=3) are shown. #P<0.05 compared with sham operated animals, 1-way ANOVA followed by Bonferroni post-hoc test, mean+SEM.

Figure 7:
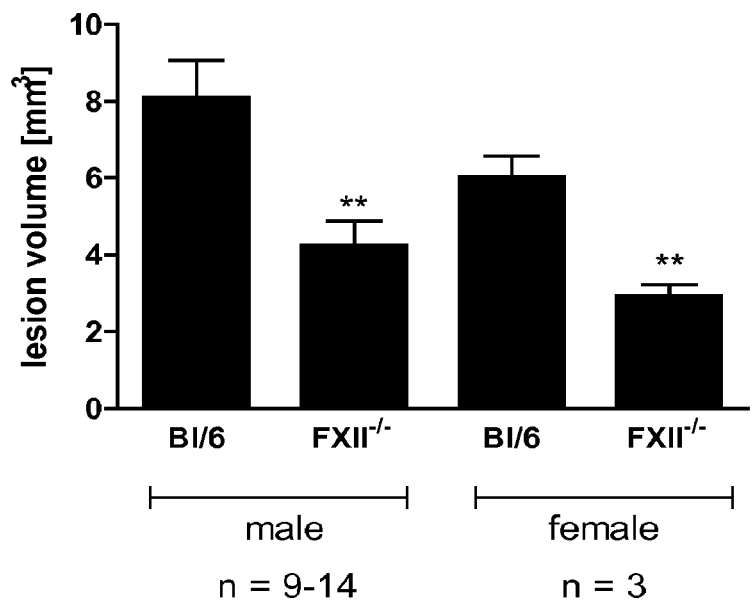
FIG. 7 shows reduction in lesion size in $FXII^{-/-}$ mice compared to WT controls 3 d after trauma induction. Lesion volumes were measured in TTC-stained brain slices and show protection from tissue damage for both male and female $FXII^{-/-}$ mice.

FIG. 7 shows reduction in lesion size in FXII$^{-/-}$ mice compared to wild-type controls (Bl/6) 3 d after trauma induction. FXII-deficient mice are protected from tissue damage at Day 3. Lesion volumes were measured in TTC-stained brain slices in male (n=9 for FXII$^{-/-}$ and n=14 for Bl/6) and female mice (n=3). **P<0.01, unpaired, two-tailed Student's t-test, mean+SEM.

Figure 8:
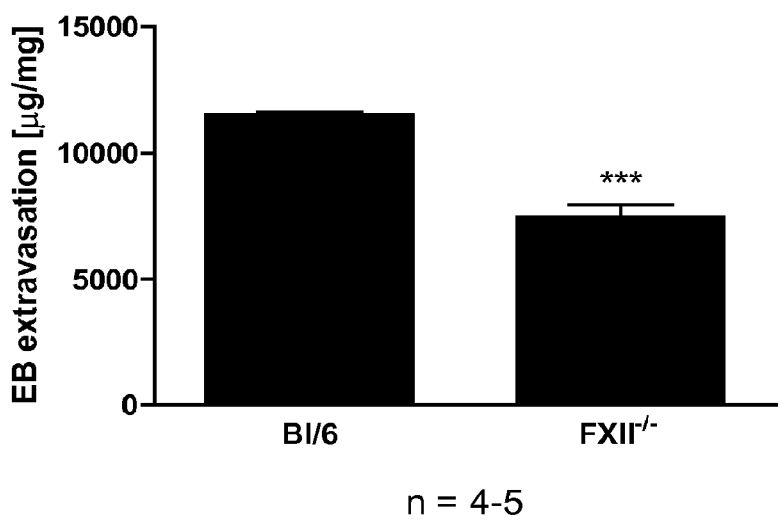
FIG. 8 shows reduction of the blood-brain-barrier (BBB) damage 3 d after trauma induction in $FXII^{-/-}$ mice compared to WT controls. BBB integrity was analyzed by the extent of Evans Blue extravasation in the lesioned hemisphere determined by photometry.

FIG. 8 shows reduction of the blood-brain-barrier (BBB) damage 3 d after trauma induction in FXII$^{-/-}$ mice compared to wild-type controls (Bl/6). BBB integrity is preserved in FXII$^{-/-}$ mice at Day 3 after trauma induction. Extent of Evans Blue extravasation in the lesioned hemisphere was determined by photometry (n=4 for Bl/6 and n=5 for FX$^{-/-}$). ***P<0.001, unpaired, two-tailed Student's t-test, mean+SEM.

Figure 9:
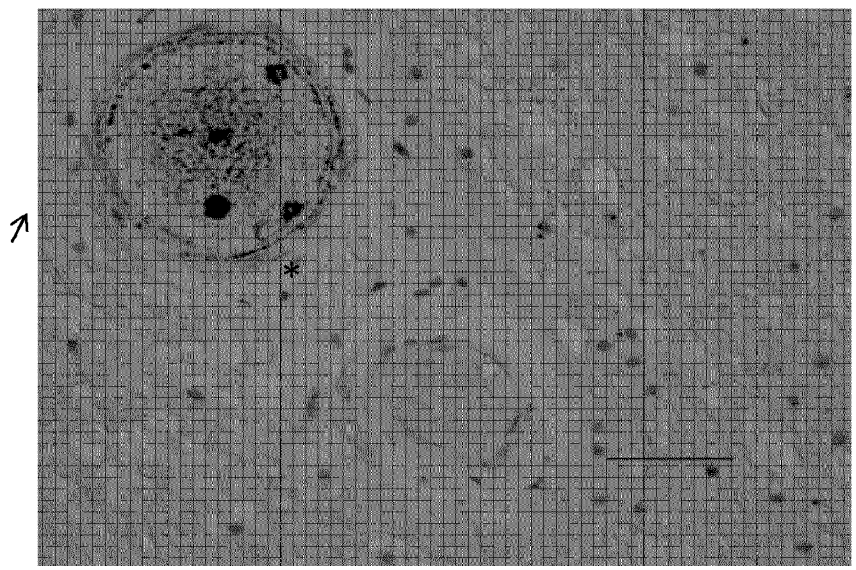
FIG. 9 shows intracerebral platelet accumulation and thrombosis as pathologic features of traumatic brain injury (after weight drop injury and cryolesion).
Figure 9:
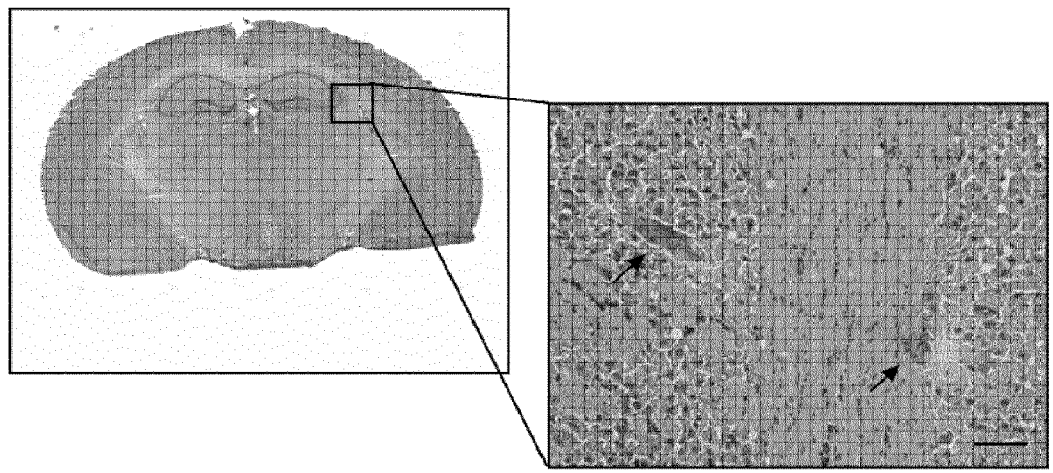
Figure 9:
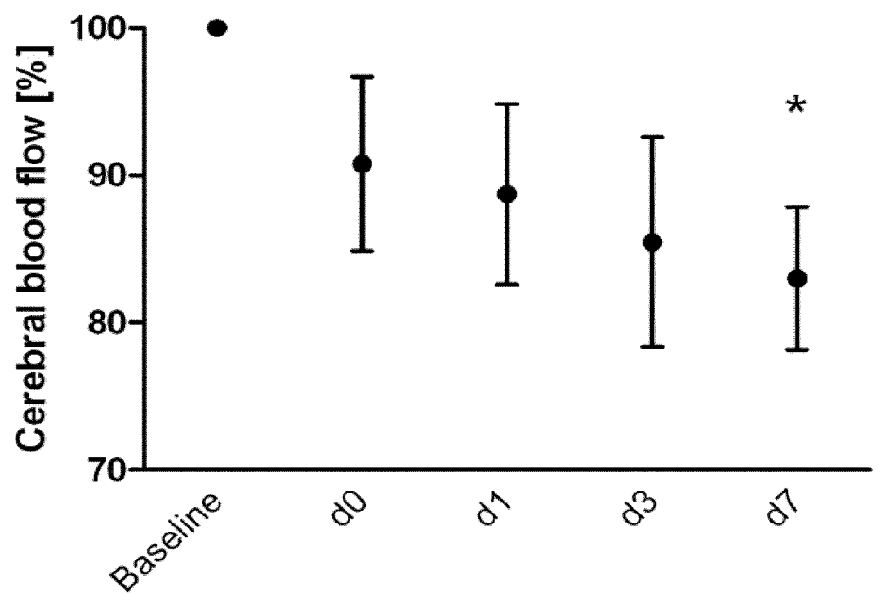
Figure 9:
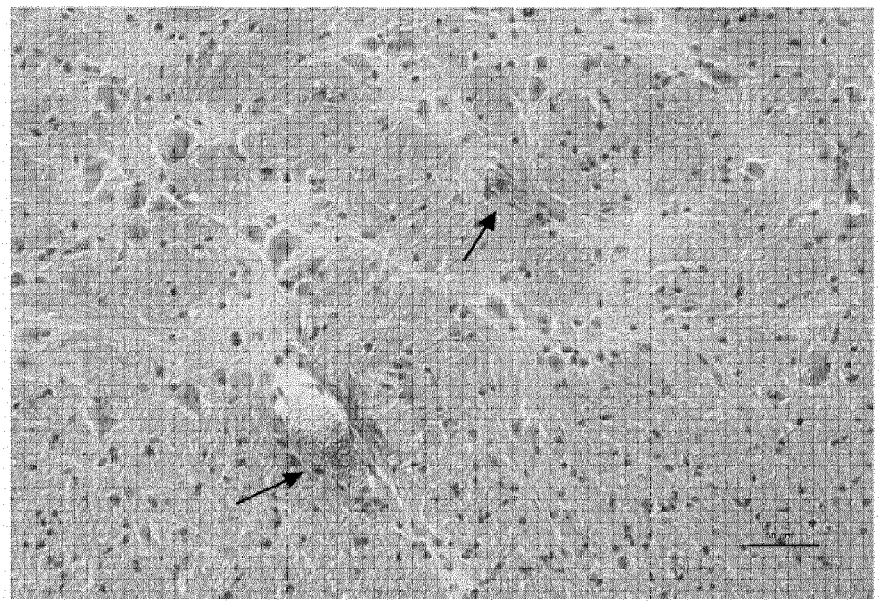

FIG. 9 shows intracerebral platelet accumulation and thrombosis are pathological features of traumatic brain injury. (A) Representative immunohistological staining for the platelet marker glycoprotein Ib (GPIb) of human traumatized brain tissue shows marked intravascular platelet deposition (arrow; non-occluded vessel is indicated by an asterisk; scale bar represents 100 μm). (B) Representative hematoxylin and eosin staining from a mouse brain section of the lesioned hemisphere on day 7 after weight drop injury shows occluded vessels (arrows; scale bar represents 100 μm). (C) The cerebral blood flow over the right parietal cortex (impact area) decreases significantly within 7 days. (E) Representative hematoxylin and eosin staining from a mouse brain section of the lesioned hemisphere on day 1 after cryolesion shows occluded vessels (arrow; scale bar represents 100 μm).

Figure 10:
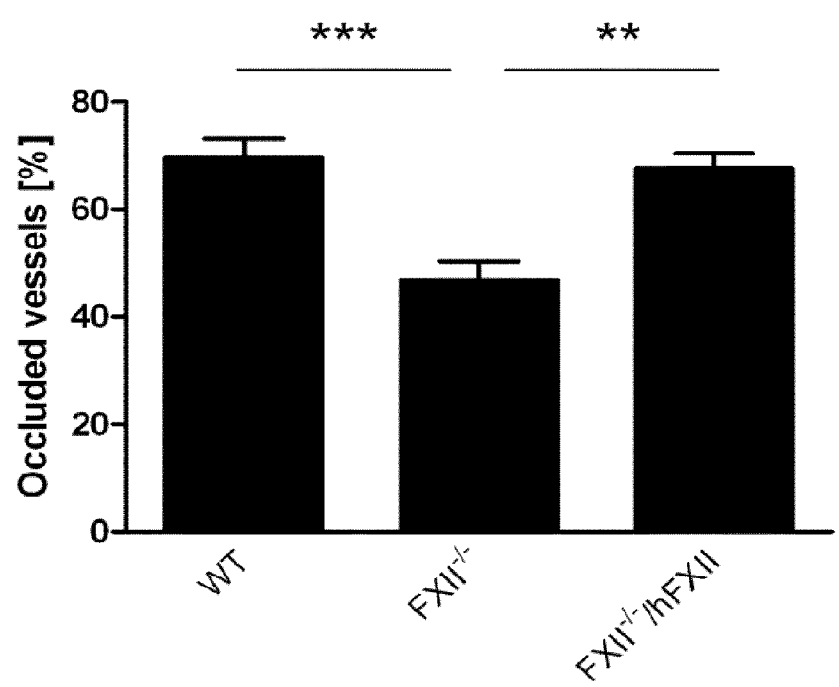
FIG. 10 shows diminishment of intracerebral platelet accumulation on day 7 after weight drop injury in $FXII^{-/-}$ mice.
Figure 10:
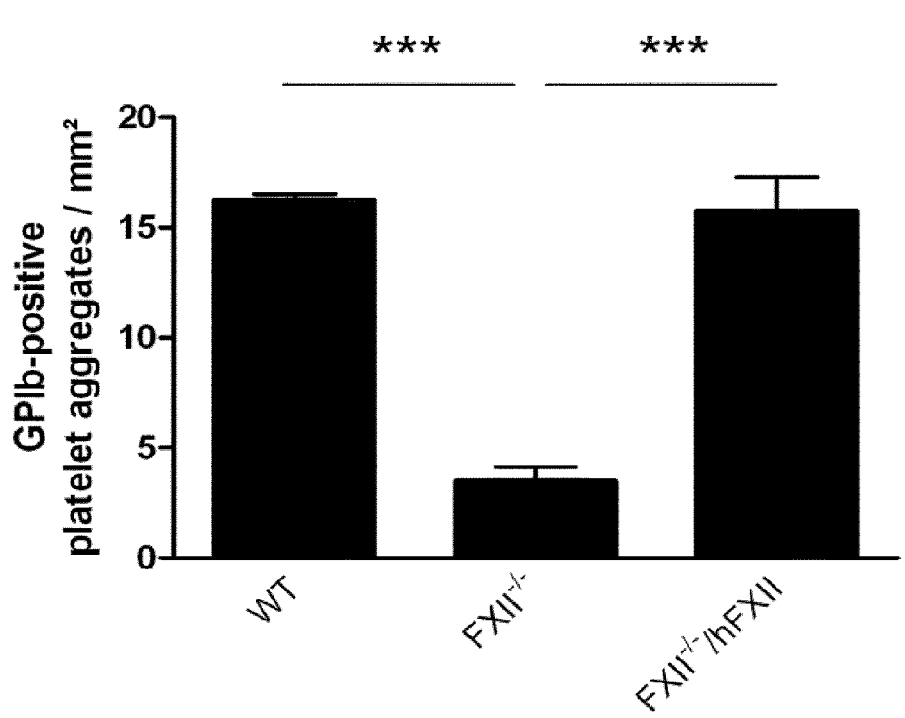
Figure 10:
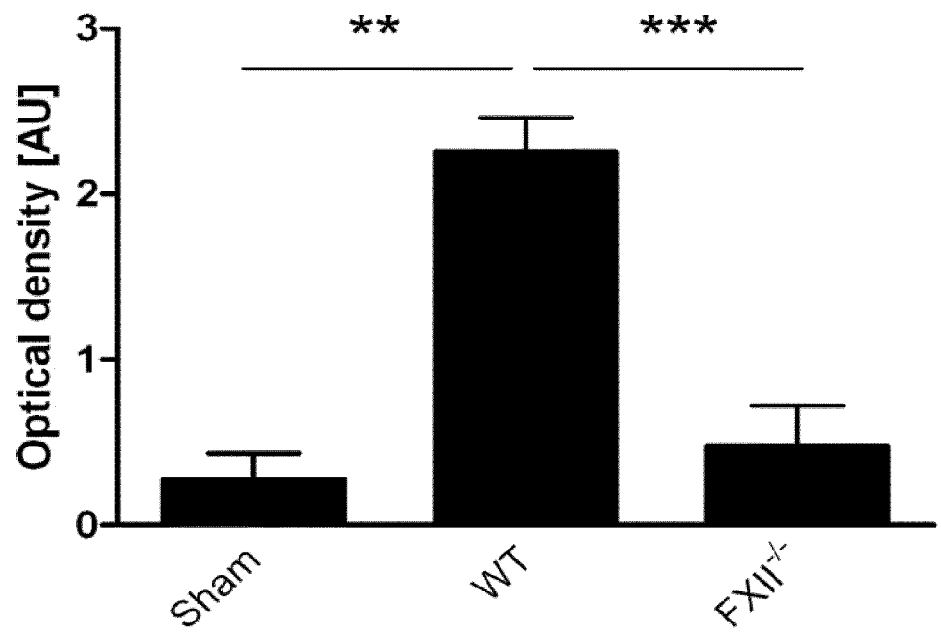
Figure 10:
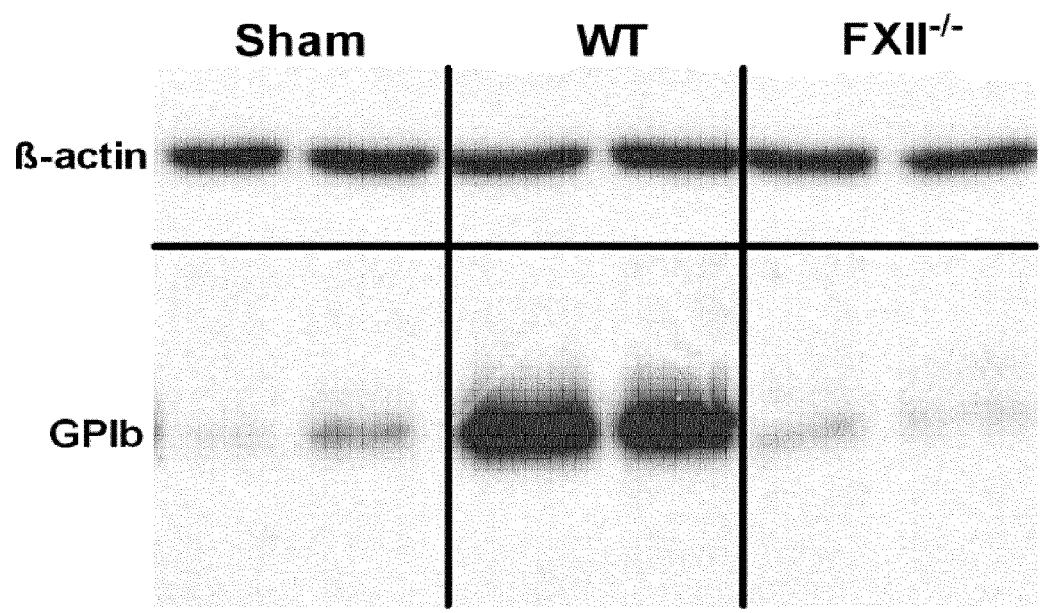

FIG. 10 shows intracerebral platelet accumulation on day 7 after weight drop injury is diminished in factor XII-deficient (FXII$^{-/-}$) mice. (A) Calculation of the thrombosis index from brain sections stained with hematoxylin and eosin shows that occluded vessels were decreased in FXII$^{-/-}$ mice when compared with wild-type (WT) mice and FXII$^{-/-}$ mice reconstituted with human FXII (FXII$^{-/-}$/hFXII) (n=5 per group, *P<0.001, P<0.01). (B) Analysis of immunfluorescence stainings using glycoprotein Ib (GPIb) and CD31 antibodies reveals marked reduction in intravascular platelet depositions on day 7 after injury induction in FXII$^{-/-}$ mice when compared with WT mice and FXII$^{-/-}$/hFXII mice (n=4 per group, *P<0.001). (C) Western Blot analysis using a GPIb antibody confirms that platelets accumulate to a smaller extent in FXII$^{-/-}$ mice when compared to WT controls or sham-operated mice. Bands were quantified by densitometry in relation to ß-actin control. Lower panel shows two representative blots of each group (n=5 per group, *P<0.001, **P<0.01; AU=arbitrary units).

Figure 11:
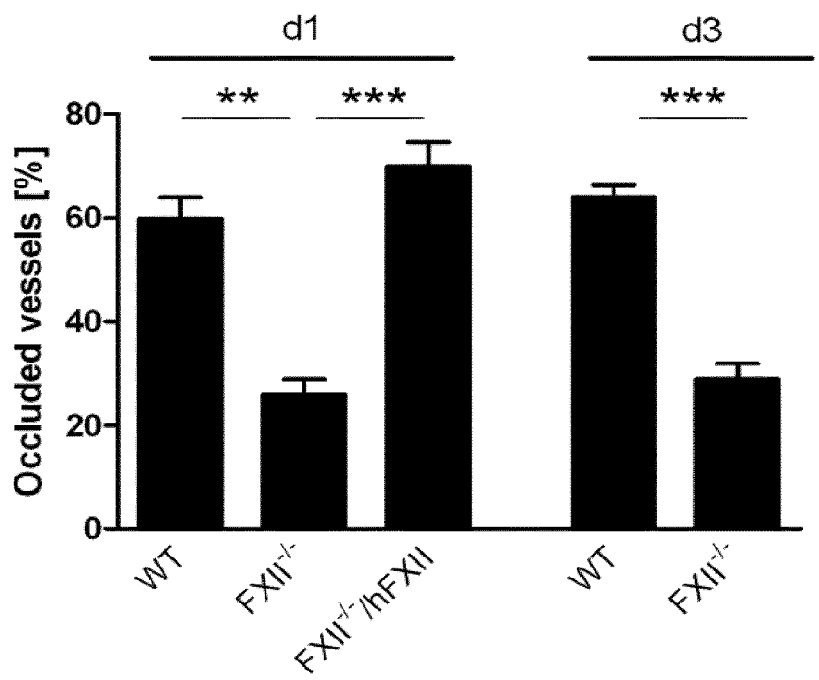
FIG. 11 shows diminishment of intracerebral platelet accumulation on day 1 and day 3 after cryolesion $FXII^{-/-}$ mice.
Figure 11:
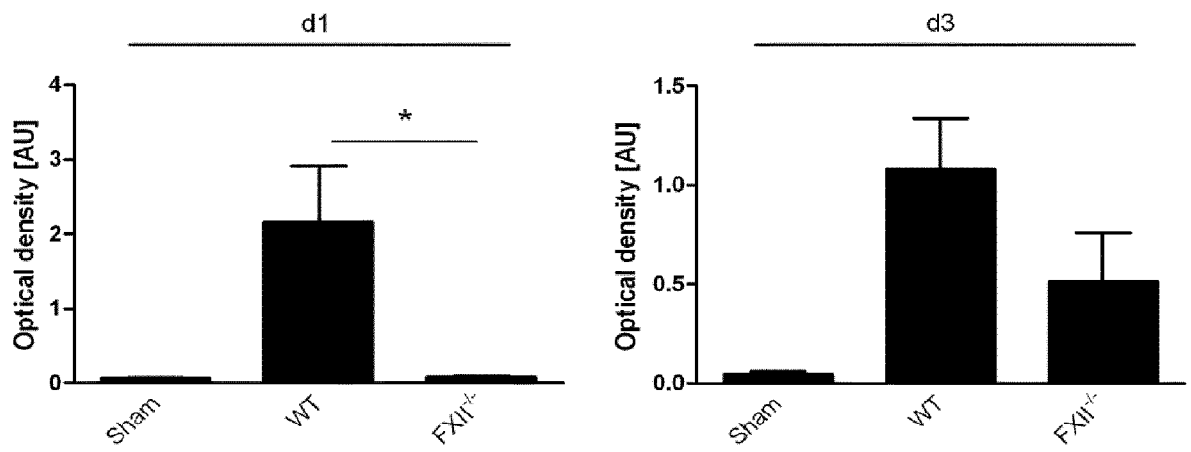
Figure 11:
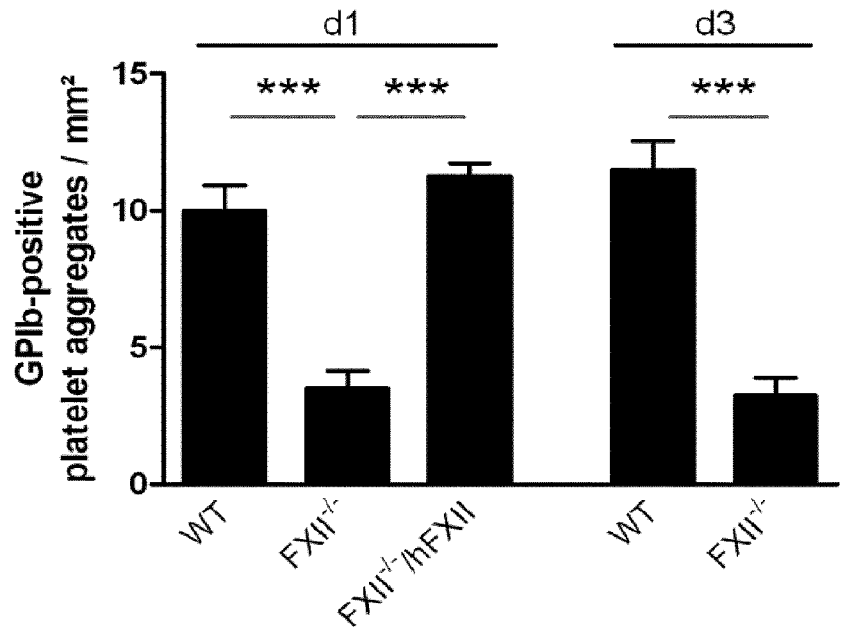

FIG. 11 shows intracerebral platelet accumulation on day 1 (d1) and day 3 (d3) after cryolesion is diminished in factor XII-deficient (FX$^{-/-}$) mice. (A) Calculation of the thrombosis index from brain sections stained with hematoxylin and eosin shows that occluded vessels are decreased in FXII$^{-/-}$ mice when compared with wild-type (WT) mice and FXII$^{-/-}$ mice reconstituted with human FXII (FXII$^{-/-}$/hFXII) (n=5 per group, *P<0.001,  P<0.01). (B) Western Blot analysis using a glycoprotein Ib (GPIb) antibody confirms that platelets accumulate to a smaller extent in FXII$^{-/-}$ mice when compared to VVT controls or sham-operated mice (Sham). Bands were quantified by densitometry in relation to ß-actin control (n=5 per group, *P<0.05). (C) Analysis of immunofluorescence stainings using GPIb and CD31 antibodies reveals marked reduction in intravascular platelet depositions in FXII$^{-/-}$ mice when compared with WT mice and FXXX$^{-/-}$/hFXII mice.

Figure 12:
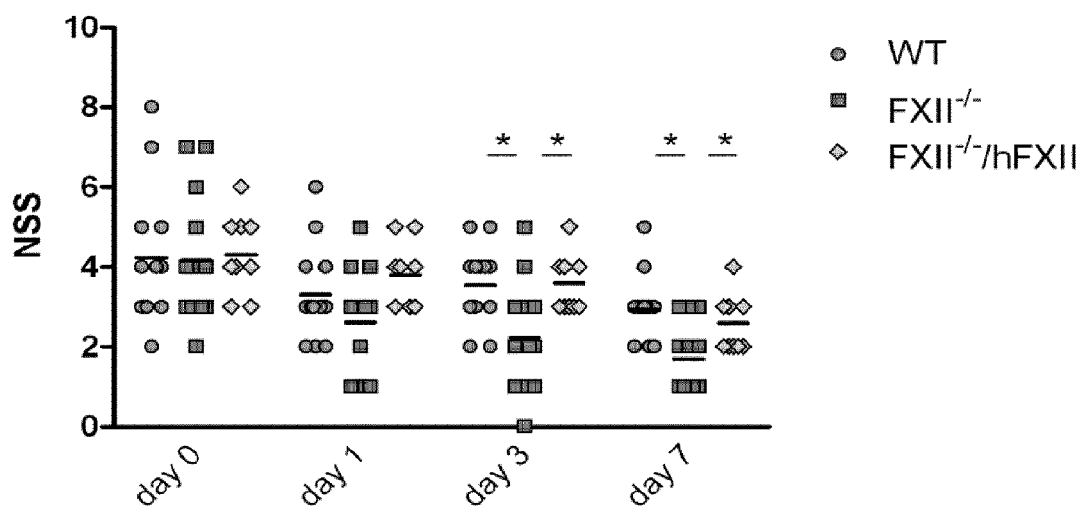
FIG. 12 shows improvement of FXII-deficiency in the outcome after weight drop injury by $FXII^{-/-}$ mice developing a significantly lower neurological severity score than wild-type mice and $FXII^{-/-}$ mice reconstituted with human FXII on day 3 and on day 7 after diffuse brain trauma.

FIG. 12 shows Factor XII (FXII)-deficiency improves outcome after weight drop injury. FXII-deficient (FXII$^{-/-}$) mice develop a significantly lower neurological severity score (NSS) than wild-type (WT) mice and FXII$^{-/-}$ mice reconstituted with human FXII (FXII$^{-/-}$/hFXII) on day 3 and on day 7 after diffuse brain trauma. One hour (day 0) and 1 day after trauma, animals displayed similar neurological deficits (n=10-13 per group, *P<0.05).

Figure 13:
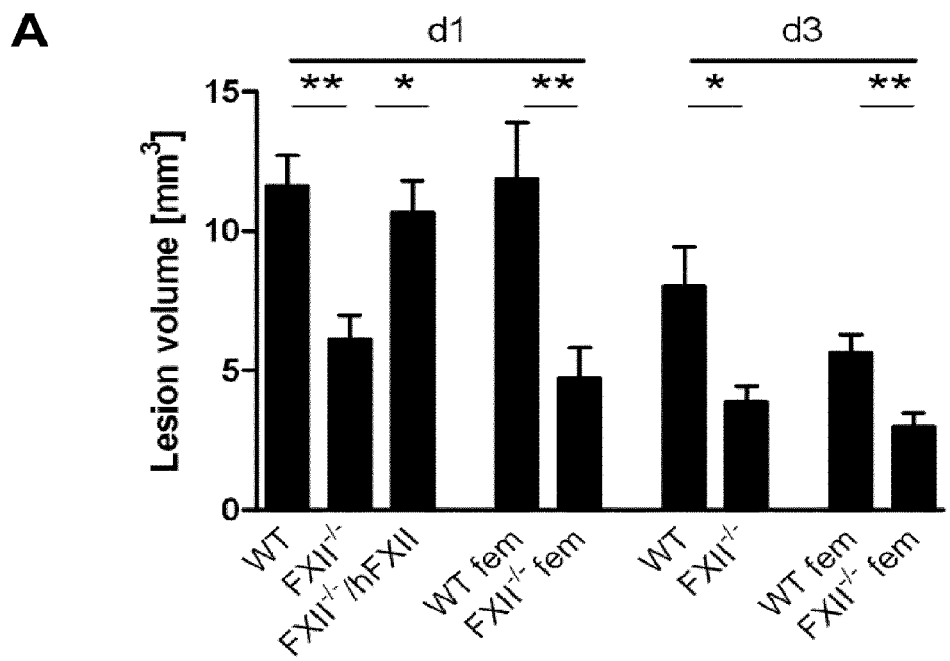
FIG. 13 shows improvement of FXII-deficiency in the outcome after cryolesion by $FXII^{-/-}$ mice showing significantly reduced lesion volumes compared to WT mice and showing a significantly diminished number of apoptotic neurons in $FXII^{-/-}$ mice when compared to WT controls.
Figure 13:
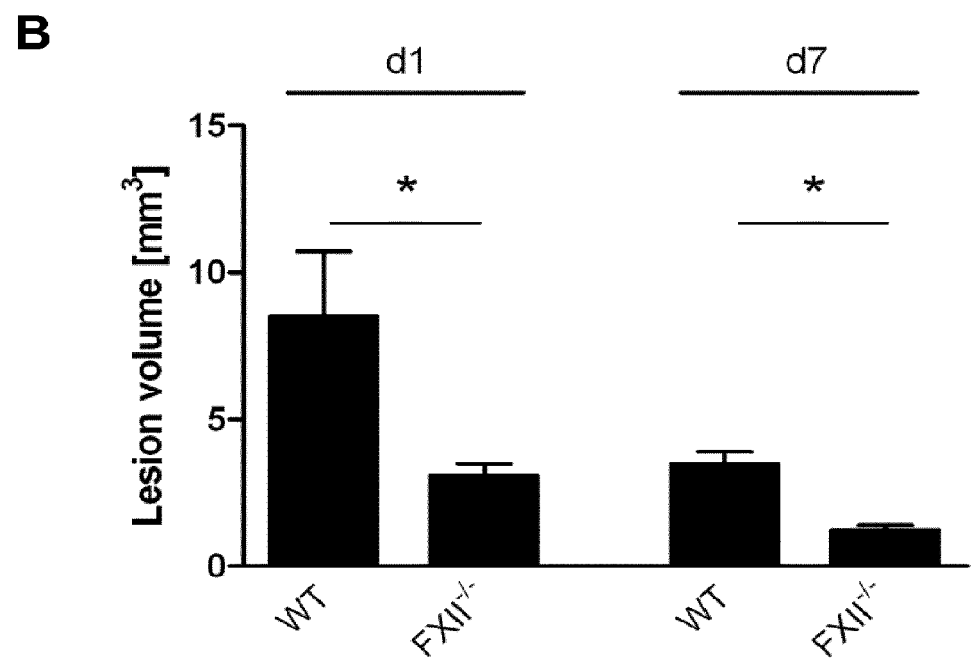
Figure 13:
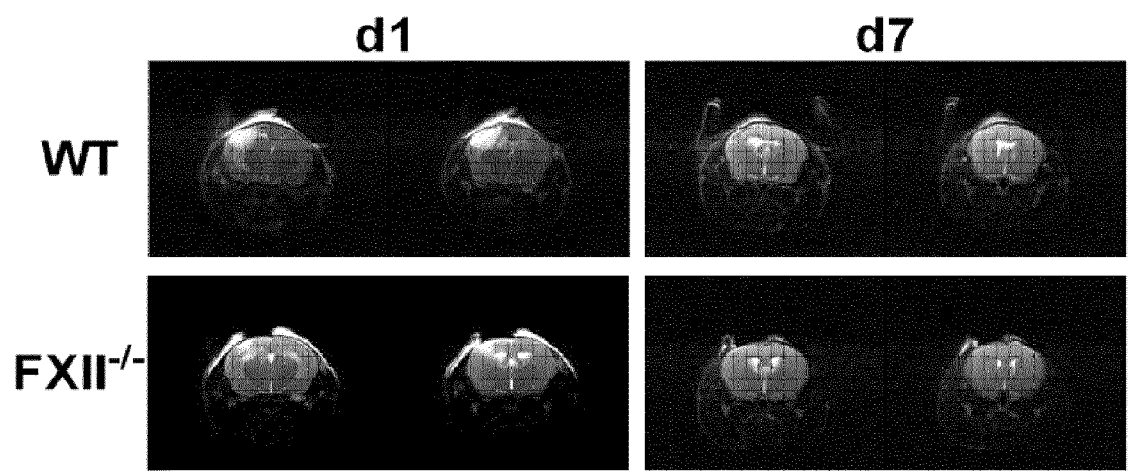
Figure 13:
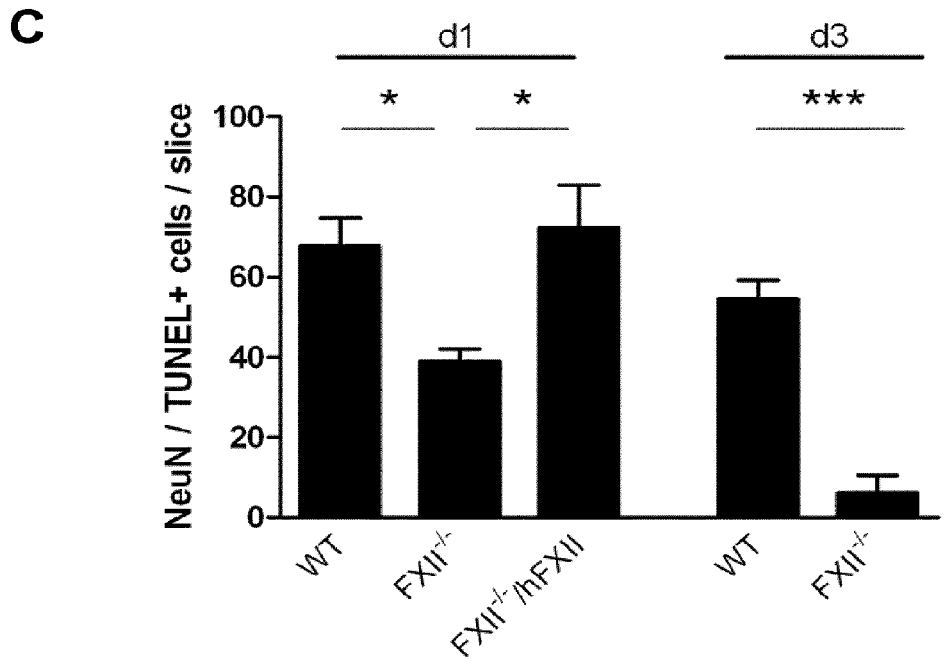

FIG. 13 shows Factor XII (FXII)-deficiency improves outcome after cryolesion. (A) Lesion volumetry after 2,3,5-triphenyltetrazolium chloride (TTC) staining of brain sections from male wild-type (WT) mice, FXII-deficient (FXII$^{-/-}$) mice, FXII$^{-/-}$ mice reconstituted with human FXII (FX$^{+/-}$+hFXII), female wild-type (WT fem) mice and female FXII$^{-/-}$ (FXII$^{-/-}$ fem) mice was performed on day 1 (d1) and day 3 (d3) after focal brain trauma. Male and female FXII$^{-/-}$ mice show significantly reduced lesion volumes when compared to WT mice. The beneficial effect of FXII-deficiency can be reverted by application of human FXII (hFXII) (n=7 per group, **P<0.01, *P<0.05). (B) Serial coronal T2-weighted gradient echo MR images show hyperintense lesions on d1 and day 7 (d7) after trauma induction in WT mice and FXII$^{-/-}$ mice. Hypointense areas indicating intracerebral hemorrhage are absent in both groups. Lower panel shows two representative brain slices per group and time-point. MRI-based lesion volumetry (upper panel) confirms the development of smaller lesions in FXII$^{-/-}$ mice (n=8-9 per group, *P<0.05). (C) Neuronal apoptosis is diminished in FXII$^{-/-}$ mice. Panel shows the number of TUNEL-positive neurons per brain slice in the injured hemisphere on d1 and on d3. The number of apoptotic neurons is significantly diminished in FXII$^{-/-}$ mice when compared to WT controls (n=4 per group, ***P<0.001, *P<0.05, scale bar represents 50 μm).

Figure 14:
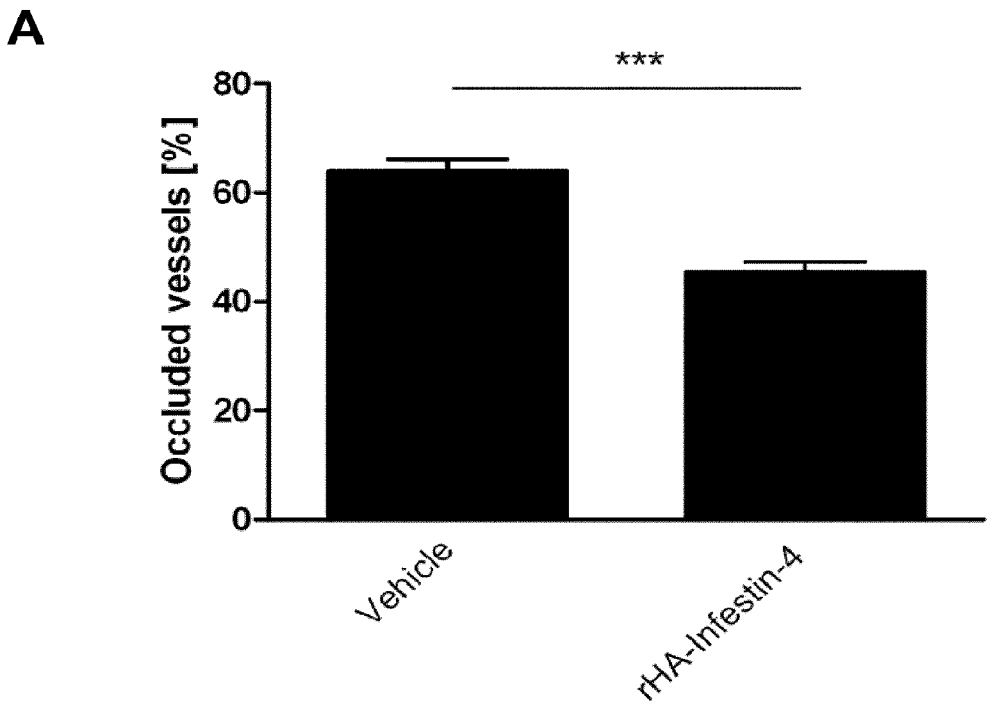
FIG. 14 shows diminishment of intracerebral platelet accumulation and improvement of the outcome after weight drop brain trauma by pharmacological inhibition of FXII with rHA-Infestin-4.
Figure 14:
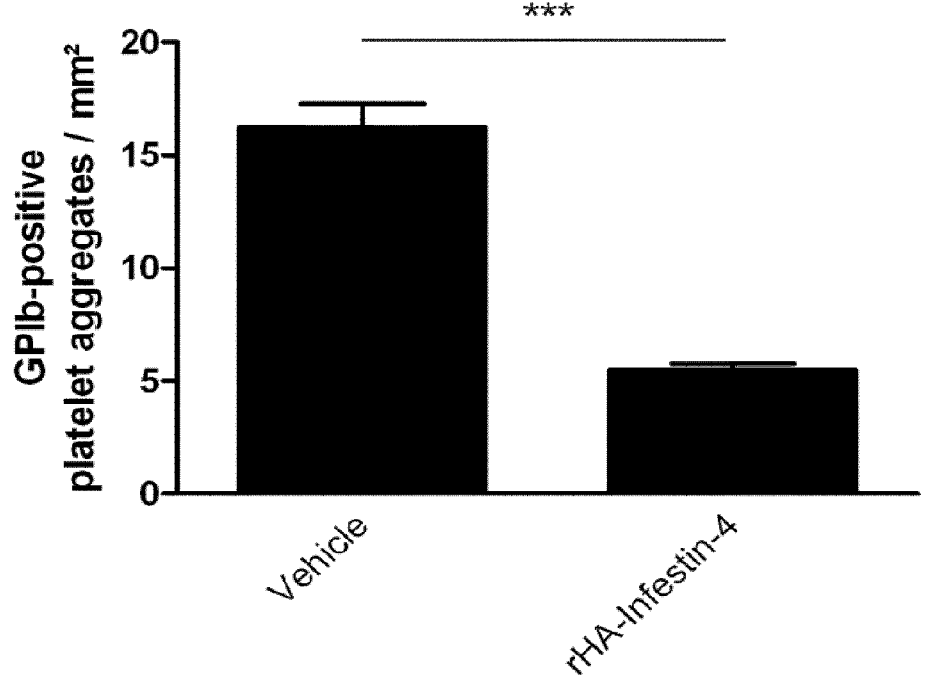
Figure 14:
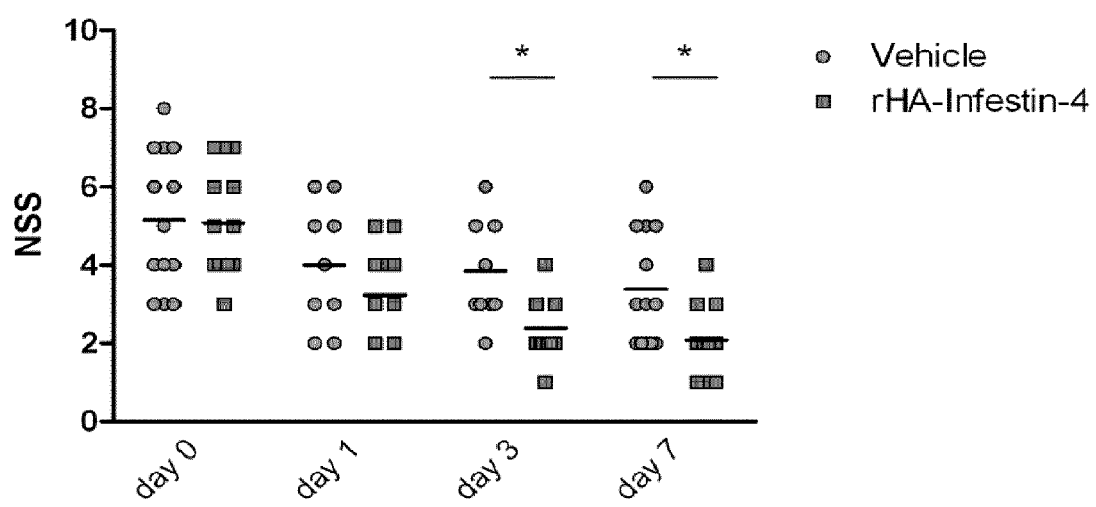

FIG. 14 shows pharmacological inhibition of factor XII (FXII) with rHA-Infestin-4 diminishes intracerebral platelet accumulation and improves outcome after weight drop brain trauma. (A) Occluded vessels are more abundant in vehicle-treated mice and when compared to mice treated with rHA-Infestin-4. This finding is confirmed by calculating the thrombosis index from brain sections stained with hematoxylin and eosin on day 7 showing a highly significant decrease of occluded vessels in mice treated with rHA-Infestin-4 (n=5 per group, *P<0.001). (B) Analysis of immunofluorescence stainings using glycoprotein Ib (GPIb) and CD31 antibodies reveals marked reduction in intravascular platelet depositions on day 7 after injury induction when mice were treated with rHA-Infestin-4 (n=4 per group, *P<0.001). (C) Mice treated with rHA-Infestin-4 develop a significantly lower neurological severity score (NSS) than vehicle-treated (Vehicle) mice on day 3 and on day 7 after brain trauma. One hour (day 0) and 1 day after brain trauma, animals displayed similar neurological deficits (n=13 per group, *P<0.05).

Figure 15:
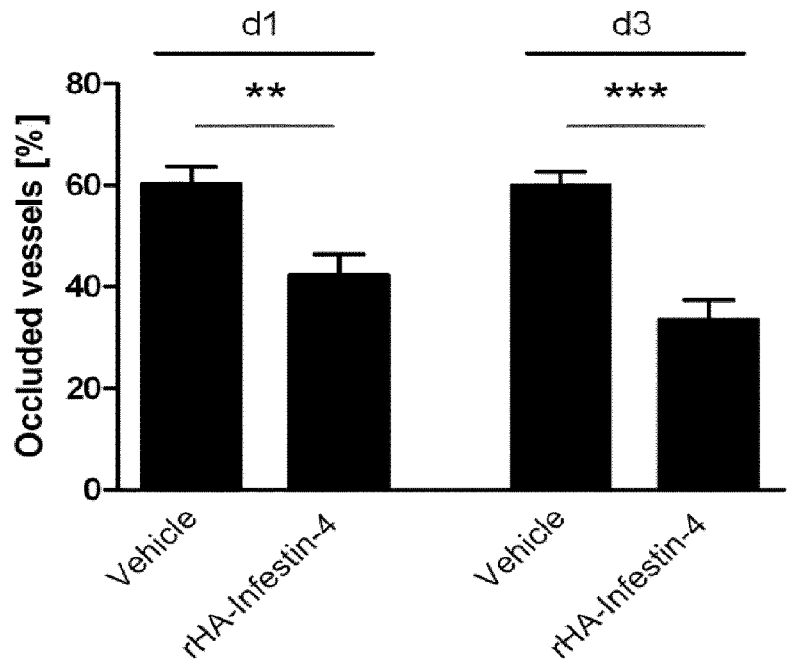
FIG. 15 shows diminishment of intracerebral platelet accumulation and protection from focal brain trauma by pharmacological inhibition of FXII with rHA-Infestin-4.
Figure 15:
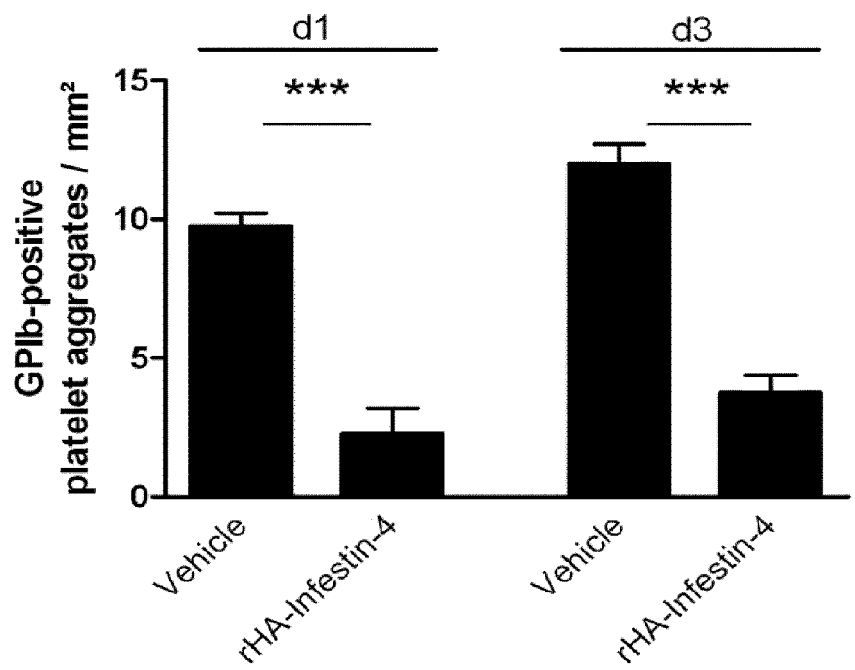
Figure 15:
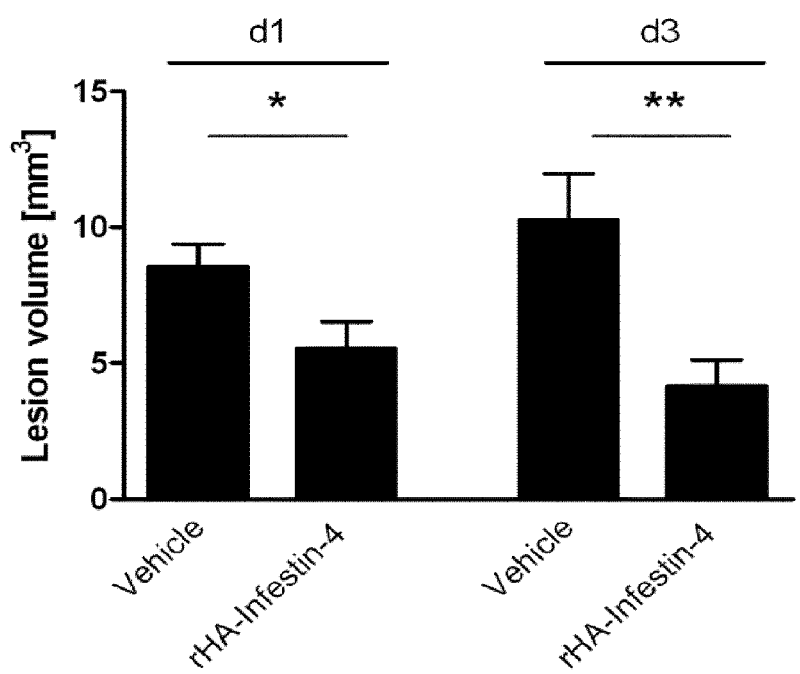
Figure 15:
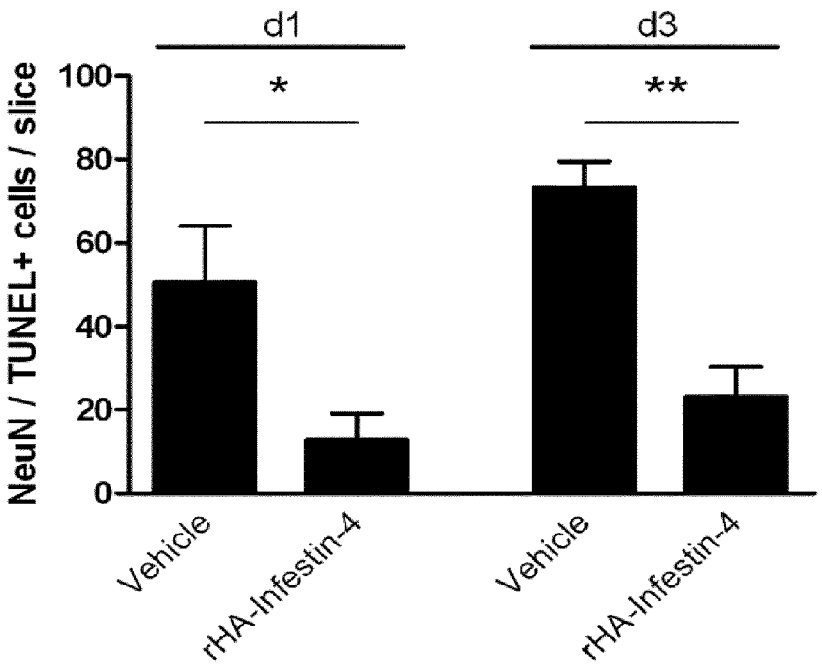

FIG. 15 shows pharmacological inhibition of factor XII with rHA-Infestin-4 diminishes intracerebral platelet accumulation and provides protection from focal brain trauma. (A) Occluded vessels are more abundant in vehicle-treated animals when compared to rHA-Infestin-4-treated mice as determined by calculating the thrombosis index on day 1 (d1) and on day 3 (d3) after injury induction showing a highly significant increase of occluded vessels in vehicle-treated animals (n=4 per group, *P<0.001, P<0.01, scale bar represents 100 μm). (B) Analysis of immunofluorescence stainings using glycoprotein Ib (GPIb) and CD31 antibodies reveals marked reduction in intravascular platelet aggregation on d1 and d3 after injury induction when mice were treated with rHA-Infestin-4 (n=4 per group, *P<0.001). (C) Lesion volumetry after 2,3,5-triphenyltetrazolium chloride (TTC) staining of brain sections of vehicle-treated mice and mice treated with rHA-Infestin-4 was performed on d1 and d3 after focal brain trauma. Mice treated with rHA-Infestin-4 are substantially protected from brain trauma (n=7 per group, P<0.01, *P<0.05). (D) The number of TUNEL-positive neurons per brain slice was assessed after immunolabeling for the neuronal marker NeuN and subjection to TUNEL assay to detect apoptosis. The number of apoptotic neurons is significantly diminished in rHA-Infestin-4-treated mice when compared to vehicle-treated controls on d1 and d3 (n=4 per group, **P<0.01, *P<0.05).

Figure 16:
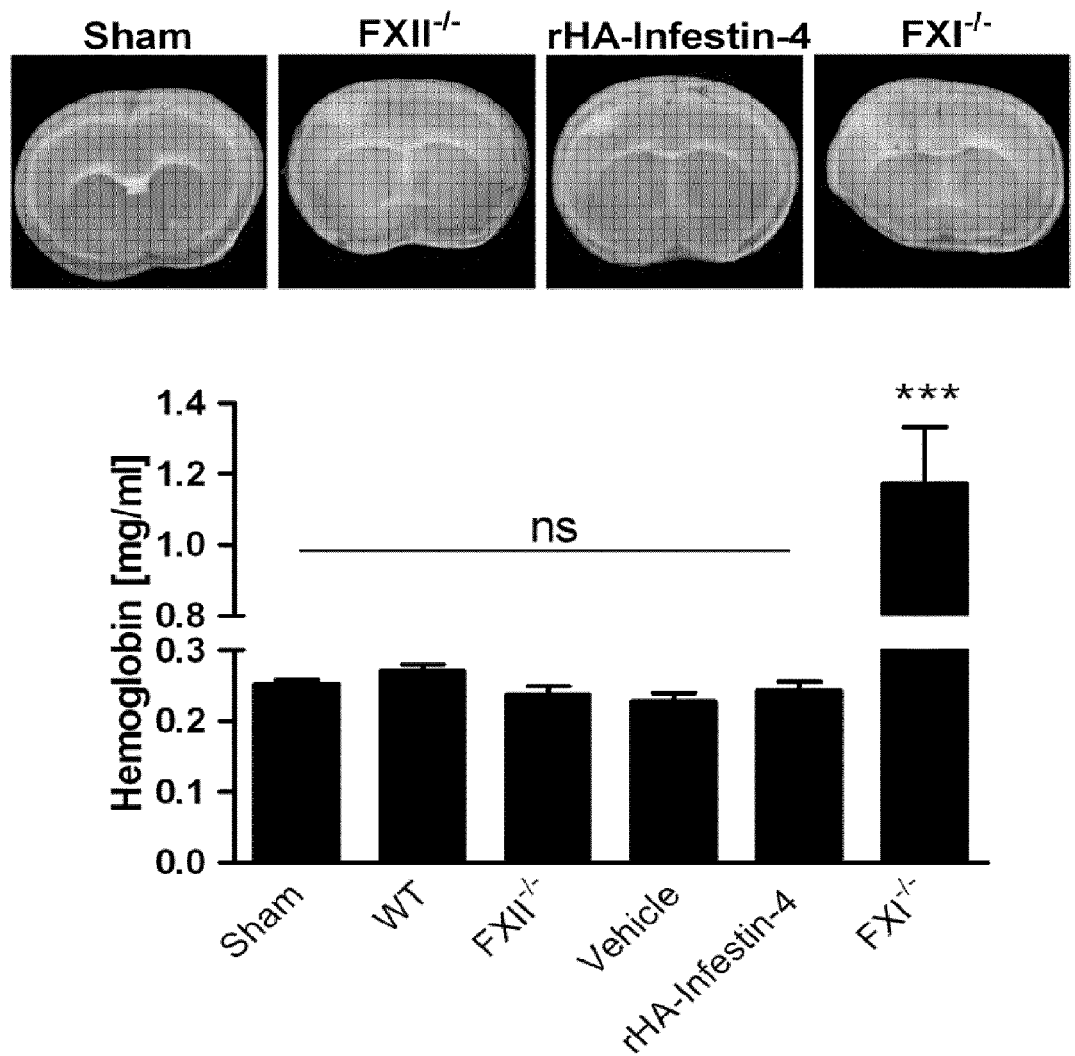
FIG. 16 shows genetic deficiency and pharmacological inhibition of FXII does not lead to hemorrhages after cryolesion.

FIG. 16 shows genetic deficiency and pharmacological inhibition of factor XII does not lead to hemorrhages after cryolesion. Upper panel shows representative brain slices stained with 2,3,5-triphenyltetrazolium chloride (TTC) of sham-operated mice, FXII-deficient mice, mice treated with rHA-Infestin-4 and mice deficient for FXI. Lower panel shows the amount of hemoglobin in the lesioned hemispheres of sham-operated mice (Sham), wild-type (WT) mice, FXII-deficient (FXII$^{-/-}$) mice, vehicle-treated (Vehicle) mice, mice treated with rHA-Infestin-4 and FXI-deficient (FXI$^{-/-}$) mice one day after trauma induction. Hemoglobin concentrations in the groups with FXII-inhibition remain at the level of sham-operated animals, FXI$^{-/-}$ mice show highly significantly increased amounts of hemoglobin (n=4-5 per group, ns=not significant, ***P<0.001).

Figure 17:
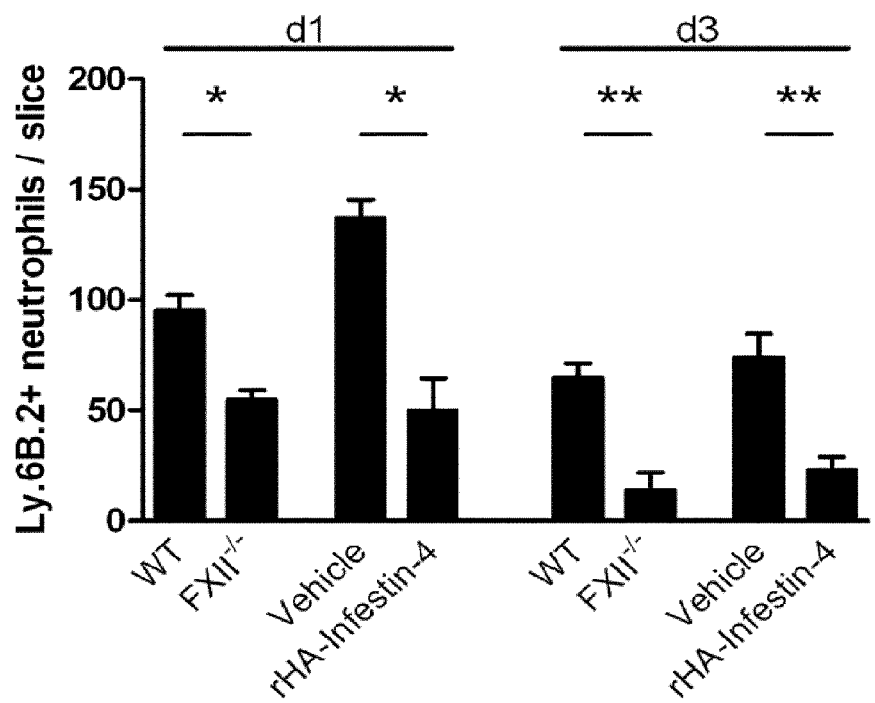
FIG. 17 shows reduction of immune cell infiltration 24 hours and 3 days after injury induction.

FIG. 17 shows reduction of immune cell infiltration 24 hours and 3 days after injury induction. The amount of Ly.6B.2-positive neutrophils was determined immunohistochemically in FXII$^{-/-}$-mice and rHA-Infestin-4-treated mice in comparison with WT or NaCl-treated controls, respectively.

The examples illustrate the invention. The example is intended to illustrate and in no way limit the present disclosure. Other embodiments of the disclosed compositions and methods will be apparent to those skilled in the art from consideration of the specification and practice of the compositions and methods disclosed herein.

EXAMPLE 1

Methods 6-week old C57Bl/6 wild-type mice (Bl/6) and FXII-deficient mice (FXII$^{-/-}$) were subjected to experimental focal TBI using a cortical cryogenic lesion model. For pharmacological inhibition of activated FXII, wild-type mice were treated with rHA-Infestin-4 (200 mg/kg i.v.) 1 h after trauma induction. Lesion size was determined by volumetry from brain slices stained with 2,3,5-triphenyltetrazolium chloride (TTC). To assess blood-brain-barrier (BBB) damage, intracerebral Evans Blue (EB) extravasation was measured by photometry and the wet-to-dry weight ratio was calculated for measurement of brain water content (=edema). Western Blot (WB) analysis and immunohistochemical (IHC) stainings were performed to assess protein expression of tight junction proteins and fibrin/fibrinogen. The local inflammatory response after TBI was analyzed by PCR and histology.

Results 24 h after trauma induction, a significant reduction in lesion size could be observed in FXII$^{-/-}$ mice as well as in rHA-Infestin-4-treated wild-type mice when compared with controls. Less thrombus formation within the brain vasculature as well as preserved BBB integrity could be identified as underlying mechanisms. Moreover, FXII inhibition dampened the local inflammatory response after TBI. Furthermore, reduction in lesion size and preservation of BBB integrity could be observed in FXII$^{-/-}$ mice 3 days after trauma induction when compared with controls.

Conclusion

Blocking of FXII protects from TBI by reducing 'thrombo-inflammation'. Therefore, inhibition of FXII is a promising strategy to combat TBI and other neurological, preferably neurotraumatic disorders.

EXAMPLE 2

Material and Methods

Animals

A total of 124 (110 male and 14 female) C57Bl/6N (wild-type) mice, 55 (41 male and 14 female) FXII-deficient (FXII$^{-/-}$) mice (Pauer et al., 2004, *Thromb Haemost* 92:503-508), and 5 male FXI-deficient (FXI$^{-/-}$) mice (Gailani et al., 1997, *Blood Coagul Fibrinolysis* 8:134-144) were used in this study. Mice were housed in groups of five to nine with free access to food and water and a 12-hour light/12-hour dark cycle. In this study, all experiments were approved by institutional and regulatory authorities and were conducted in accordance with the EU Directive 2010/63/EU and the ARRIVE criteria (Kilkenny et al., 2012, *Osteoarthritis Cartilage* 20:256-260).

Cortical Cryolesion Model

Cortical cryolesion was induced as described previously (Albert-Weissenberger et al., 2014, *Frontiers in cellular neuroscience* 8:269). Briefly, 6 week old mice were anesthetized with intraperitoneal injections of ketamine (0.1 mg/g) and xylazine (0.005 mg/g). After restraining the mouse head in a stereotactic frame (TSE systems) surgery was performed on the right parietal cortex after exposing the skull through a scalp incision. A copper cylinder with a tip diameter of 2.5 mm was filled with liquid nitrogen (−196° C.) and placed on the right parietal cortex (coordinates from the bregma: 1.5 mm caudal, 1.5 mm lateral) for 90 s. Sham-operated animals underwent the same surgical procedure without cooling of the copper cylinder.

Weight Drop Model

Experimental closed head injury was performed as previously described (Albert-Weissenberger et al., 2012, *J Cereb Blood Flow Metab* 32:1747-1756; Albert-Weissenberger et al., 2012, *Exp Transl Stroke Med* 4:1). Briefly, after the induction of isoflurane anesthesia, spontaneously breathing 10 to 16 week old mice were placed in a stereotactic frame and the skull was exposed by a midline longitudinal scalp incision. After the identification of the impact area a weight with a silicone-covered blunt tip was dropped with a final impact of 0.01 J. Sham-operation included anesthesia and exposure of the skull but without weight drop injury. The neurobehavioral status of mice was assessed by the neurological severity score (NSS), a composite score including tasks on motor function, alertness and physiological behavior with lower scores indicating less deficits. Mice were evaluated 1 hour, 1 day, 3 days, and 7 days after weight drop injury. Personnel who performed functional assays were blinded to the experimental groups.

Pharmacological Treatment

One hour after induction of focal cryolesion or diffuse weight drop injury, wild-type mice received a single intravenous injection of the specific FXII-inhibitor rHA-Infestin-4 (CSL Behring, Marburg, Germany) at a dose of 200 mg/kg body weight. Control animals received equal volumes of 0.9% sodium chloride (vehicle). Intravenous injection of 2 μg/g body weight human FXII (hFXII) (Sekisui Diagnostics, ADG412H) 1 h after injury induction and continually every 72 h resulted in reconstitution of FXII$^{-/-}$ mice.

Determination of Lesion Size after Cortical Cryolesion

Twenty-four hours or 3 days after cryolesion, mice were sacrificed; the brains were quickly removed and cut in five 1 mm thick coronal sections using a mouse brain slice matrix (Harvard Apparatus). The slices were stained for 20 min at 37° C. with 2% 2,3,5-triphenyltetrazolium chloride (TTC; Sigma-Aldrich) in PBS to visualize the lesion. Lesion volumes were calculated by volumetry (ImageJ software, National Institutes of Health, USA) in a blinded fashion.

Magnetic Resonance Imaging

MRI was performed repeatedly 1 day and 7 days after cryolesion on a 3 Tesla unit (Vision; Siemens) under anesthesia with ketamine (0.1 mg/g) and xylazine (0.005 mg/g). The protocol included a coronal T2-weighted sequence (slice thickness 2 mm), and a blood-sensitive coronal T2-weighted gradient echo CISS sequence (Constructed Interference in Steady State; slice thickness 1 mm). Lesion volumes were calculated by planimetry of the hyperintense area on high-resolution CISS images. CISS images were additionally examined for possible intracerebral bleeding.

Laser Doppler Flowmetry

Laser Doppler flowmetry (Moor Instruments) was used to monitor regional cerebral blood flow over the right parietal cortex (impact area). Cerebral blood flow was measured serially at baseline (before injury induction), 1 hour, 3 and 7 days after injury induction.

Histology and Immunohistochemistry

Cryo-embedded mouse brains were cut into 10-μm-thick or 15-μm-thick slices (cortical cryolesion model and weight drop model, respectively) using a cryostat (Leica). For assessment of the thrombosis index hematoxylin and eosin staining was performed according to standard procedures. Stainings were examined in a blinded fashion and the number of occluded ($N_{occ}$) and non-occluded ($N_{open}$) blood vessels within the lesioned hemispheres was counted in every tenth brain slice under a 20-fold magnification. The thrombosis index was calculated using the following equation: ($N_{occ}/(N_{open}+N_{occ}))\times 100$. To assess platelet aggregates within the vessels in the human brain, paraffin-embedded sections were stained against glycoprotein Ib (GPIb; abcam, ab102647) according the manufacturer's protocol and then counter-stained with hematoxylin to visualize all nuclei. For immunofluorescence stainings, the following primary antibodies were applied: anti-GPIb (1:100, kind gift from Prof. Nieswandt, Rudolf-Virchow-Zentrum, Würzburg), anti-CD31 (Bio-Rad Laboratories, MCA2388GA, 1:100), anti-NeuN (Millipore, MAB377, 1:1000). As secondary antibodies, Cy2 anti-rat (Dianova, 122-225-167, 1:100), Cy3 anti-rat (Dianova, 712-165-150, 1:100) and DyLight 488 anti-mouse (abcam, ab96871, 1:100) were used. Neuronal apoptosis was assessed using a TUNEL (terminal deoxynucleotidyl transferase dUTP nick-end labeling) in situ Cell Death Detection Kit (Roche, Basel, Switzerland) according to the manufacturers instructions. Numbers of apoptotic neurons were determined from three fields at a 40-fold magnification from the lesioned hemisphere of two brain slices under a Nikon microscope Eclipse 50i equipped with the DS-U3 DS camera control unit and the NIS-Elements software (Nikon, Düsseldorf, Germany). To assess platelet aggregates two brain slices per animal were quantified. For quantitative analysis we used sections from near-identical brain regions for better comparison between groups.

Western Blot Analysis

Immunoreactivity for GPIb (anti-GPIb, 1:500, kind gift from Prof. Nieswandt, Rudolf-Virchow-Zentrum, Würzburg) in lesioned cortices was detected by Western Blot analysis as previously described (Langhauser et al., 2012, *Blood*, 120(19):4082-92). Densitometric analysis of GPIb was performed in a blinded way using the ImageJ software (National Institutes of health, USA) with ß-Actin (Dianova, A5441, 1:500000) as loading control to normalize the levels of GPIb detected.

Quantification of Intracerebral Hemorrhage

Hemoglobin concentration in brain parenchyma that correlates to the extent of hemorrhage was determined spectrophotometrically (Choudhri et al., 1997, *Stroke* 28:2296-2302). Twenty-four hours after trauma animals were sacrificed and the brains were removed. The lesioned hemispheres were sonified for 60 s in 1.5 ml ice-cooled water and afterwards centrifuged at 4° C. for 30 min. One ml of Drabkin's solution was added to 250 µl of the supernatant and incubated at room temperature for 15 min. The absorbance was measured at 540 nm (MultiskanEX, Thermo Scientific, Waltham, MA).

Experimental Design

Numbers of animals necessary to detect a standardized effect size on lesion volumes ≥0.2 on day 1 after cortical cryolesion or NSS ≥0.2 on day 1 after weight drop injury, respectively, were determined via a priori sample size calculation with the following assumptions: $\alpha=0.05$, $\beta=0.2$, mean, and standard deviation (G*Power 3.0.10). Mice have been randomly assigned to treatment groups (block randomization after cryolesion and to achieve balanced groups stratified randomization after weight drop injury). To avoid bias, experiments have been performed and analyzed in a blinded fashion.

Statistics

All results were expressed as mean±SEM except for the NSS scales which are depicted as scatter plots including median with the 25% percentile and the 75% percentile given in brackets in the text. For statistical analysis Prism-Graph 5.0 software package (GraphPad Software) was used. Data were tested for Gaussian distribution with the Kolmogorov Smirnov test and in case of measuring the effects of two factors simultaneously analyzed by two-way ANOVA with post hoc Bonferroni correction for multivariate analyses or in case of non-parametric data (NSS) Kruskal Wallis test with post hoc Dunns correction. In case of measuring the effect of one factor, one-way ANOVA with post hoc Bonferroni correction was applied. If only two groups were compared, unpaired, two-tailed Student's t test was performed. P values <0.05 were considered statistically significant.

Results

Microvascular Thrombosis is a Common Pathological Feature in Traumatic Brain Injury Firstly, we analyzed a human brain sample obtained after a fatal case of TBI, showing that platelets accumulate in the microvessels of the traumatized brain (FIG. 9A). Consequently, we closely mimicked human TBI in mice using a weight drop model resulting in a predominantly diffuse brain trauma. Hematoxylin and eosin stainings of injured brain tissue from wild-type mice showed numerous occlusions of vessel lumina (FIG. 9B). Accordingly, we found intravascular accumulation of platelets. Interestingly, the cerebral blood flow at the impact area slightly decreased over time with a significantly reduced cerebral blood flow on day 7 after weight drop injury (FIG. 9C). When focal brain trauma was induced by cortical cryolesion numerous occluded vessels and intravascular accumulations of GPIb-positive platelets were found in cortical brain tissue on day 1 and 3 after injury induction (FIG. 1D). These results strongly support the hypothesis that microvascular thrombosis is a common pathological feature in TBI.

Factor XII Contributes to Microvascular Thrombosis in Traumatic Brain Injruy

To assess the impact of FXII on intracerebral thrombus formation after TBI, we first analyzed contusioned brain tissue of FXII-deficient mice in comparison with wild-type mice or FXII-deficient mice that were reconstituted with intravenous injections of hFXII (FXII$^{-/-}$/hFXII). On day 7 after weight drop injury, histological analysis of hematoxylin and eosin-stained brain sections demonstrated fewer occluded cerebral microvessels in FXII$^{-/-}$ mice when compared with wild-type or FXII$^{-/-}$/hFXII mice (FIG. 10A). We consistently detected less intravascular GPIb-positive platelet accumulations in brains of FXII-deficient mice (FIG. 10B). Furthermore, Western Blot analyses confirmed that the amount of platelets was significantly diminished in brain tissue of FXII-deficient mice (FIG. 10C). Similar to weight drop injury, fewer thrombus-occluded brain vessels (FIG. 11A), less platelet accumulations in the brain vasculature (FIG. 11C), and a decreased amount of platelets in the brain tissue (FIG. 11B) was detected one and three days after focal cryolesion in FXII$^{-/-}$ mice when compared with wild-type mice.

In summary, we observed that the injury-induced microvascular thrombosis and brain damage could be reproduced in FXII-deficient mice that were reconstituted by the administration of hFXII. This proves for the first time that activation of the intrinsic coagulation pathway by FXII plays a role in posttraumatic cerebral thrombus formation. Consequently, we conclude that FXII contributes to microvascular thrombosis independently of the nature of TBI.

Factor XII Deficiency Results in a Better Outcome after Traumatic Brain Injury

To evaluate the pathological significance of reduced intracerebral thrombosis in FXII-deficient mice, we next determined the impact of FXII-deficiency on functional outcome after weight drop injury. Trauma severity at early stages (1 h and 1 day after injury induction) was comparable in all groups, 3 days after weight drop injury FXII$^{-/-}$ mice had recovered significantly better than wild-type or FXII$^{-/-}$/hhFXII mice (median NSS [25th percentile, 75th percentile]: 4.0 [3.0, 4.0] in wild-type mice and 3.5 [3.0, 4.0] in FXII$^{-/-}$/hFXII mice vs 2.0 [1.0, 3.0] in FXII$^{-/-}$ mice, P<0.05, respectively; FIG. 12). Importantly, the better neurological outcome in FXII$^{-/-}$ mice was persistent until day 7 (median NSS [25th percentile, 75th percentile]: 3.0 [2.0, 3.0] in wild-type mice and 2.5 [2.0, 3.0] in FXII$^{-/-}$/hFXII mice vs 1.0 [1.0, 2.5.0] in FXII$^{-/-}$ mice, P<0.05, respectively; FIG. 12).

We next evaluated the impact of FXII-deficiency on cortical lesion volume and neurodegeneration on day 1 and 3 after cryolesion. In male mice, FXII-deficiency resulted in significantly reduced lesion volumes on day 1 and 3 as assessed by TTC-staining of brain sections (FIG. 13A). As gender has a significant impact on the clinical outcome following TBI (Wright et al., 2014), we subjected female mice to cryolesion. FXII-deficiency in female mice also resulted in significantly smaller brain lesions on day 1 and 3 when compared with wild-type mice (FIG. 13A). These observations were corroborated by studies using brain MRI showing that FXII-deficiency resulted in sustained reduction in lesion size after focal brain injury (FIG. 13B). Reduction in lesion volume was accompanied with significantly diminished neuronal apoptosis in mice deficient for FXII on day 1 after cryolesion when compared with control mice (FIG. 13C). An even more pronounced difference in the amount of apoptotic cells was observed on day 3 after cryolesion (FIG. 13C).

Pharmaceutical Inhibition of Factor XII Results in Reduced Microvascular Thrombosis and a Better Outcome after Traumatic Brain Injury To test the efficacy of pharmacological FXII inhibition for treatment of pathological thrombosis in TBI, we administered the selective inhibitor of activated FXII, rHA-Infestin-4, 200 mg/kg body weight intravenously and monitored microvascular thrombosis, functional outcome and lesion volumes in mice subjected to weight drop injury or cryolesion. Detailed analysis of hematoxylin and eosin-stained brain sections and immunohistochemistry visualizing platelets and endothelium showed that fewer thrombi occluded cerebral microvessels in rHA-Infestin-4-treated mice when compared with vehicle-treated mice in both TBI models (FIGS. 14A, 14B, 15A, and 15B).

The diminished thrombus formation in rHA-Infestin-4-treated mice was associated with better neurological outcome. While after weight drop injury the initial severity of neurological deficits (1 h and day 1) was comparable between the treatment groups (P>0.05), 3 and 7 days after trauma rHA-Infestin-4-treated mice had recovered significantly better than vehicle-treated mice (day 3: median NSS [25th percentile, 75th percentile]: 2.0 [2.0, 3.0] in rHA-Infestin-4-treated mice vs 3.0 [3.0, 3.0] in vehicle-treated mice, P<0.05; day 7: median NSS [25th percentile, 75th percentile]: 2.0 [1.5, 2.5] in rHA-Infestin-4-treated mice vs 3.0 [2.0, 5.0] in vehicle-treated mice, P<0.05; FIG. 14C). After cryolesion, lesion volume and neurodegeneration on day 1 and 3 was reduced in rHA-Infestin-4-treated mice when compared with vehicle-treated mice. For both readouts the protective effect of rHA-Infestin-4 was even more pronounced on day 3 than on day 1 after cryolesion (FIGS. 7C and 7D).

Similar to FXII-deficiency, acute treatment of mice with rHA-Infestin-4 prevents from pathological thrombus formation in the cerebral microcirculation in both TBI models. The decrease in thrombus formation is associated with a better neurological outcome preserved at later stages after brain trauma (day 3, day 7), less brain damage, and less neurodegeneration after weight drop injury and cryolesion injury, respectively. As a single administration of rHA-Infestin-4 after brain trauma seems sufficient for protection against injury deterioration. In summary, pharmacological inhibition of FXII results in reduced microvascular thrombosis and a better outcome after experimental TBI.

FXII Deficiency or Inhibition Does Not Increase the Risk of Intracerebral Bleedings To prove the safety of FXII inhibition after brain trauma with regard to abnormal cerebral bleedings, we determined the extent of hemorrhage in the lesioned brain hemispheres of FXII$^{-/-}$ mice, rHA-Infestin-4-treated mice, and their respective controls. After cryolesion, neither FXII-deficient mice nor mice treated with rHA-Infestin-4, showed increased levels of hemorrhages (FIG. 16). To validate this result, we also determined the extent of hemorrhage in FXI$^{-/-}$ mice as FXI-deficiency is associated with increased post-traumatic bleedings in humans (Rosenthal et al., 1955, *Blood* 10:120-131). In these mice we observed increased hemorrhages in the lesioned brain hemispheres that can also be seen macroscopically (FIG. 16). Moreover, MRI scans of FXII-deficient mice and wild-type controls showed no signs of bleeding either.

---

The invention claimed is:

1. A method of treating a neurotraumatic disorder in a human or animal subject, comprising administering to a subject in need thereof a direct inhibitor of FXII in an amount sufficient to treat microvascular thrombosis in the neurotraumatic disorder, wherein the neurotraumatic disorder resulted from a traumatic injury of the brain of the subject, wherein the inhibitor of FXII is an anti-FXII antibody comprising:
   (a) a heavy chain variable region comprising a heavy chain complementarity determining region 1 (HCDR1) sequence of SEQ ID NO: 8, a heavy chain complementarity determining region 2 (HCDR2) sequence of SEQ ID NO: 10, and a heavy chain complementarity determining region 3 (HCDR3) sequence of SEQ ID NO: 11; and
   (b) a light chain variable region comprising a light chain complementarity determining region 1 (LCDR1) sequence of SEQ ID NO: 13, a light chain complementarity determining region 2 (LCDR2) sequence of SEQ ID NO: 14, and a light chain complementarity determining region 3 (LCDR3) sequence of SEQ ID NO: 15, wherein SEQ ID NO: 10 has the sequence $GIX_1X_2X_3X_4X_5X_6TVYADSVKG$, and $X_1$ is D, $X_2$ is I, $X_3$ is P, $X_4$ is T, $X_5$ is K, and $X_6$ is G.

2. The method of claim 1, wherein the anti-FXII antibody is an IgG antibody.

3. The method of claim 1, wherein the FXII inhibitor is linked to a fusion partner comprising PEG or a half-life enhancing polypeptide selected from albumin, afamin, alpha-fetoprotein, vitamin D binding protein, human albumin, an immunoglobulin, and an Fc of an IgG.

4. The method of claim 3, wherein the half-life enhancing polypeptide is linked to the FXII inhibitor via a linker.

5. The method of claim 3, wherein the FXII inhibitor is a fusion protein comprising human albumin joined to a FXII inhibitor via a linker peptide.

6. The method of claim 1, wherein the FXII inhibitor is administered intravenously, subcutaneously, or intrathecally.

7. The method of claim 1, wherein the FXII inhibitor is administered (i) in a single dose as an injection or an infusion, (ii) in multiple doses, each as an injection or an infusion, or (iii) as a continuous infusion or application.

8. The method of claim 1, wherein the FXII inhibitor is administered at a concentration ranging from about 0.01 mg/kg body weight to about 1000 mg/kg body weight.

9. The method of claim 1, wherein the FXII inhibitor is administered after the traumatic injury.

10. The method of claim 9, wherein the FXII inhibitor is first administered immediately after the traumatic injury or up to 24 hours after the traumatic injury.

11. The method of claim 1, wherein the FXII inhibitor is administered once, twice, three times, four times, or five times.

12. The method of claim 1, wherein the FXII inhibitor is administered at a concentration ranging from about 1 mg/kg body weight to about 500 mg/kg body weight.

13. The method of claim 9, wherein the FXII inhibitor is first administered up to 12 hours after the traumatic injury.

14. The method of claim 9, wherein the FXII inhibitor is first administered up to 6 hours after the traumatic injury.

15. The method of claim 1, wherein the heavy chain variable region comprises an amino acid sequence having at least 95% sequence identity to SEQ ID NO: 6 and the light chain variable region comprises an amino acid sequence having at least 95% sequence identity to SEQ ID NO: 7.

16. The method of claim 1, wherein the heavy chain variable region comprises an amino acid sequence having at least 95% sequence identity to the heavy chain variable region of VR115 and the light chain variable region comprises an amino acid sequence having at least 95% sequence identity to the light chain variable region of VR115.

17. The method of claim 1, wherein the heavy chain variable region comprises an amino acid sequence having at least 98% sequence identity to the heavy chain variable region of VR115 and the light chain variable region comprises an amino acid sequence having at least 98% sequence identity to the light chain variable region of VR115.

18. The method of claim 1, wherein the antibody comprises the variable domains of VR115.

* * * * *

SEQUENCE LISTING

```
<160> NUMBER OF SEQ ID NOS: 20

<210> SEQ ID NO 1
<211> LENGTH: 48
<212> TYPE: PRT
<213> ORGANISM: Triatoma infestans

<400> SEQUENCE: 1

Glu Val Arg Asn Pro Cys Ala Cys Phe Arg Asn Tyr Val Pro Val Cys
1               5                   10                  15

Gly Ser Asp Gly Lys Thr Tyr Gly Asn Pro Cys Met Leu Asn Cys Ala
            20                  25                  30

Ala Gln Thr Lys Val Pro Gly Leu Lys Leu Val His Glu Gly Arg Cys
        35                  40                  45

<210> SEQ ID NO 2
```

```
<211> LENGTH: 56
<212> TYPE: PRT
<213> ORGANISM: Homo sapiens

<400> SEQUENCE: 2

Asp Ser Leu Gly Arg Glu Ala Lys Cys Tyr Asn Glu Leu Asn Gly Cys
1               5                   10                  15

Thr Lys Ile Tyr Asp Pro Val Cys Gly Thr Asp Gly Asn Thr Tyr Pro
            20                  25                  30

Asn Glu Cys Val Leu Cys Phe Glu Asn Arg Lys Arg Gln Thr Ser Ile
        35                  40                  45

Leu Ile Gln Lys Ser Gly Pro Cys
    50                  55

<210> SEQ ID NO 3
<211> LENGTH: 53
<212> TYPE: PRT
<213> ORGANISM: Homo sapiens

<400> SEQUENCE: 3

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Pro Asn Glu Cys
            20                  25                  30

Val Leu Cys Phe Glu Asn Arg Lys Arg Gln Thr Ser Ile Leu Ile Gln
        35                  40                  45

Lys Ser Gly Pro Cys
    50

<210> SEQ ID NO 4
<211> LENGTH: 53
<212> TYPE: PRT
<213> ORGANISM: Homo sapiens

<400> SEQUENCE: 4

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
            20                  25                  30

Met Leu Cys Ala Glu Asn Arg Lys Arg Gln Thr Ser Ile Leu Ile Gln
        35                  40                  45

Lys Glu Gly Pro Cys
    50

<210> SEQ ID NO 5
<211> LENGTH: 54
<212> TYPE: PRT
<213> ORGANISM: Homo sapiens

<400> SEQUENCE: 5

Asp Ser Leu Gly Arg Glu Val Arg Asn Pro Cys Ala Cys Phe Arg Asn
1               5                   10                  15

Tyr Val Pro Val Cys Gly Thr Asp Gly Asn Thr Tyr Gly Asn Glu Cys
            20                  25                  30

Met Leu Asn Cys Ala Glu Asn Arg Lys Arg Gln Thr Ser Ile Leu Ile
        35                  40                  45

Gln Lys Glu Gly Pro Cys
    50
```

```
<210> SEQ ID NO 6
<211> LENGTH: 129
<212> TYPE: PRT
<213> ORGANISM: Homo sapiens

<400> SEQUENCE: 6
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Lys Tyr
            20                  25                  30

Ile Met Gln Trp Val Arg Gln Ala Pro Gly Lys Gly Leu Glu Trp Val
        35                  40                  45

Ser Gly Ile Arg Pro Ser Gly Thr Thr Val Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Leu Pro Arg Ser Gly Tyr Leu Ile Ser Pro His Tyr Tyr
            100                 105                 110

Tyr Tyr Ala Leu Asp Val Trp Gly Gln Gly Thr Thr Val Thr Val Ser
        115                 120                 125

Ser

```
<210> SEQ ID NO 7
<211> LENGTH: 110
<212> TYPE: PRT
<213> ORGANISM: Homo sapiens

<400> SEQUENCE: 7
```

Gln Ser Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Arg Asn
            20                  25                  30

Tyr Val Tyr Trp Tyr Gln Gln Val Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Val Ile Ser Gly Leu Arg
65                  70                  75                  80

Ser Glu Asp Glu Ala Asp Tyr Tyr Cys Ala Ala Trp Asp Ala Ser Leu
                85                  90                  95

Arg Gly Val Phe Gly Gly Gly Thr Lys Leu Thr Val Leu Gly
            100                 105                 110

```
<210> SEQ ID NO 8
<211> LENGTH: 5
<212> TYPE: PRT
<213> ORGANISM: Homo sapiens

<400> SEQUENCE: 8
```

Lys Tyr Ile Met Gln
1               5

```
<210> SEQ ID NO 9
<211> LENGTH: 17
<212> TYPE: PRT
<213> ORGANISM: Homo sapiens
```

-continued

```
<400> SEQUENCE: 9

Gly Ile Arg Pro Ser Gly Gly Thr Thr Val Tyr Ala Asp Ser Val Lys
1               5                   10                  15

Gly

<210> SEQ ID NO 10
<211> LENGTH: 17
<212> TYPE: PRT
<213> ORGANISM: Artificial
<220> FEATURE:
<223> OTHER INFORMATION: Heavy chain CDR2 showing variations
<220> FEATURE:
<221> NAME/KEY: variant
<222> LOCATION: (3)..(3)
<223> OTHER INFORMATION: Xaa is selected from Arg, Asn, and Asp
<220> FEATURE:
<221> NAME/KEY: variant
<222> LOCATION: (4)..(4)
<223> OTHER INFORMATION: Xaa is selcted from Pro, Val, Ile and Met
<220> FEATURE:
<221> NAME/KEY: variant
<222> LOCATION: (5)..(5)
<223> OTHER INFORMATION: Xaa is selected from Ser, Pro and Ala
<220> FEATURE:
<221> NAME/KEY: variant
<222> LOCATION: (6)..(6)
<223> OTHER INFORMATION: Xaa is selected from Gly, Leu, Val and Thr
<220> FEATURE:
<221> NAME/KEY: variant
<222> LOCATION: (7)..(7)
<223> OTHER INFORMATION: Xaa is selected from Gly, Tyr, Gln, Lys, Arg,
      Asn and Met
<220> FEATURE:
<221> NAME/KEY: variant
<222> LOCATION: (8)..(8)
<223> OTHER INFORMATION: Xaa is selected from Thr, Gly and Ser

<400> SEQUENCE: 10

Gly Ile Xaa Xaa Xaa Xaa Xaa Xaa Thr Val Tyr Ala Asp Ser Val Lys
1               5                   10                  15

Gly

<210> SEQ ID NO 11
<211> LENGTH: 20
<212> TYPE: PRT
<213> ORGANISM: Homo sapiens

<400> SEQUENCE: 11

Ala Leu Pro Arg Ser Gly Tyr Leu Ile Ser Pro His Tyr Tyr Tyr Tyr
1               5                   10                  15

Ala Leu Asp Val
            20

<210> SEQ ID NO 12
<211> LENGTH: 20
<212> TYPE: PRT
<213> ORGANISM: Artificial
<220> FEATURE:
<223> OTHER INFORMATION: Heavy chain CDR3 showing variations
<220> FEATURE:
<221> NAME/KEY: variant
<222> LOCATION: (9)..(9)
<223> OTHER INFORMATION: Xaa is selected from Ile, Met and Val
<220> FEATURE:
<221> NAME/KEY: variant
<222> LOCATION: (10)..(10)
<223> OTHER INFORMATION: Xaa is selcted from Ser and Lys
<220> FEATURE:
<221> NAME/KEY: variant
<222> LOCATION: (11)..(11)
```

```
<223> OTHER INFORMATION: Xaa is selected from Pro, Lys, Thr and His
<220> FEATURE:
<221> NAME/KEY: variant
<222> LOCATION: (12)..(12)
<223> OTHER INFORMATION: Xaa is selected from His, Asn, Gly and Gln

<400> SEQUENCE: 12

Ala Leu Pro Arg Ser Gly Tyr Leu Xaa Xaa Xaa Xaa Tyr Tyr Tyr Tyr
1               5                   10                  15

Ala Leu Asp Val
            20

<210> SEQ ID NO 13
<211> LENGTH: 13
<212> TYPE: PRT
<213> ORGANISM: Homo sapiens

<400> SEQUENCE: 13

Ser Gly Ser Ser Ser Asn Ile Gly Arg Asn Tyr Val Tyr
1               5                   10

<210> SEQ ID NO 14
<211> LENGTH: 7
<212> TYPE: PRT
<213> ORGANISM: Homo Sapiens

<400> SEQUENCE: 14

Ser Asn Asn Gln Arg Pro Ser
1               5

<210> SEQ ID NO 15
<211> LENGTH: 10
<212> TYPE: PRT
<213> ORGANISM: Homo sapiens

<400> SEQUENCE: 15

Ala Ala Trp Asp Ala Ser Leu Arg Gly Val
1               5                   10

<210> SEQ ID NO 16
<211> LENGTH: 10
<212> TYPE: PRT
<213> ORGANISM: Artificial
<220> FEATURE:
<223> OTHER INFORMATION: Light chain CDR3 showing variations
<220> FEATURE:
<221> NAME/KEY: variant
<222> LOCATION: (2)..(2)
<223> OTHER INFORMATION: Xaa is selected from Ala and Ser
<220> FEATURE:
<221> NAME/KEY: variant
<222> LOCATION: (4)..(6)
<223> OTHER INFORMATION: Xaa can be any amino acid
<220> FEATURE:
<221> NAME/KEY: variant
<222> LOCATION: (7)..(7)
<223> OTHER INFORMATION: Xaa is selected from Leu and Val
<220> FEATURE:
<221> NAME/KEY: variant
<222> LOCATION: (9)..(10)
<223> OTHER INFORMATION: Xaa can be any amino acid

<400> SEQUENCE: 16

Ala Xaa Trp Xaa Xaa Xaa Xaa Arg Xaa Xaa
1               5                   10

<210> SEQ ID NO 17
<211> LENGTH: 13
```

-continued

```
<212> TYPE: PRT
<213> ORGANISM: Homo sapiens

<400> SEQUENCE: 17

Ser Gly Ser Ser Glu Met Thr Val His His Tyr Val Tyr
1               5                   10

<210> SEQ ID NO 18
<211> LENGTH: 12
<212> TYPE: PRT
<213> ORGANISM: Triatoma infestans

<400> SEQUENCE: 18

Val Arg Asn Pro Cys Ala Cys Phe Arg Asn Tyr Val
1               5                   10

<210> SEQ ID NO 19
<211> LENGTH: 12
<212> TYPE: PRT
<213> ORGANISM: Triatoma infestans

<400> SEQUENCE: 19

Asp Ser Leu Gly Arg Glu Val Arg Asn Pro Cys Ala
1               5                   10

<210> SEQ ID NO 20
<211> LENGTH: 585
<212> TYPE: PRT
<213> ORGANISM: Homo sapiens

<400> SEQUENCE: 20

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220
```

```
Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
            245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Lys Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585
```